US010889627B2

(12) United States Patent
Zimmer et al.

(10) Patent No.: US 10,889,627 B2
(45) Date of Patent: Jan. 12, 2021

(54) PRO-DRUG PEPTIDE WITH IMPROVED PHARMACEUTICAL PROPERTIES

(71) Applicant: UREKA SARL, Mulhouse (FR)

(72) Inventors: Robert H. Zimmer, Mulhouse (FR); Gilles Guichard, Gradignan (FR); Juliette Fremaux, Pessac (FR); Claire Venin, Talence (FR); Sebastien Goudreau, Bordeaux (FR)

(73) Assignee: UREKA SARL, Mulhouse (FR)

( * ) Notice: Subject to any disclaimer, the term of this patent is extended or adjusted under 35 U.S.C. 154(b) by 0 days.

(21) Appl. No.: 16/023,901

(22) Filed: Jun. 29, 2018

(65) Prior Publication Data
US 2019/0002519 A1    Jan. 3, 2019

Related U.S. Application Data

(60) Provisional application No. 62/526,678, filed on Jun. 29, 2017.

(51) Int. Cl.
| | | |
|---|---|---|
| *A61K 38/00* | (2006.01) | |
| *C07K 14/605* | (2006.01) | |
| *A61K 47/54* | (2017.01) | |
| *A61K 47/64* | (2017.01) | |
| *A61P 3/08* | (2006.01) | |
| *A61K 38/26* | (2006.01) | |

(52) U.S. Cl.
CPC .......... *C07K 14/605* (2013.01); *A61K 47/542* (2017.08); *A61K 47/64* (2017.08); *A61K 47/645* (2017.08); *A61P 3/08* (2018.01); *A61K 38/00* (2013.01); *A61K 38/26* (2013.01)

(58) Field of Classification Search
None
See application file for complete search history.

(56) References Cited

U.S. PATENT DOCUMENTS

| 5,424,286 A | 6/1995 | Eng | |
|---|---|---|---|
| 2011/0065649 A1* | 3/2011 | Courty | A61K 38/02 514/18.7 |
| 2011/0117599 A1 | 5/2011 | Santer | |
| 2012/0329708 A1 | 12/2012 | Dimarchi | |
| 2017/0283479 A1* | 10/2017 | Dimarchi | A61K 47/543 |

FOREIGN PATENT DOCUMENTS

| WO | WO 2006/086769 | 8/2006 |
|---|---|---|
| WO | WO 2009/023270 | 2/2009 |
| WO | WO 2010/080578 | 7/2010 |
| WO | WO 2013/102209 | 7/2013 |
| WO | WO 2013/130684 | 9/2013 |

OTHER PUBLICATIONS

Adelhorst, K., Hedegaard, B. B., Knudsen, L. B. & Kirk, O. Structure-activity studies of glucagon-like peptide-1. J. Biol. Chem. 269, 6275-6278 (1994).
Armstrong, M. J. et al. Liraglutide safety and efficacy in patients with non-alcoholic steatohepatitis (LEAN): a multicentre, double-blind, randomised, placebo-controlled phase 2 study. Lancet 387, 679-690, doi:10.1016/S0140-6736(15)00803-X (2016).
Bain, S. C. et al. Cardiovascular safety of oral semaglutide in patients with type 2 diabetes: Rationale, design and patient baseline characteristics for the PIONEER 6 trial. Diabetes Obes. Metab. (2018) doi:10.1111/dom.13553.
Becker, A., et al., "Purification of Human Big Endothelin-1 Derived through Cleavage with Collagenase and Dipeptidylpeptidase IV from Fusion Protein Expressed in *Escherichia Coli*", Protein Expression and Purification, vol. 5, No. 1, (1994), Feb. 1, 1994, pp. 50-56.
Buse, J. B. et al. Metabolic effects of two years of exenatide treatment on diabetes, obesity, and hepatic biomarkers in patients with type 2 diabetes: an interim analysis of data from the open-label, uncontrolled extension of three double-blind, placebo-controlled trials. Clin Ther 29, 139-153, doi:10.1016/j.clinthera.2007.01.015 (2007).
Campbell, J. E. & Drucker, D. J. Pharmacology, Physiology, and Mechanisms of Incretin Hormone Action. Cell Metab. 17, 819-837 (2013).
Cheang, J. Y. & Moyle, P. M. Glucagon-Like Peptide-1 (GLP-1)-Based Therapeutics: Current Status and Future Opportunities beyond Type 2 Diabetes. ChemMedChem (2018), 13, 662-671 doi:10.1002/cmdc.201700781.
Chicchi, et al., "Alterations in receptor activation and divalent cation activation of agonist binding by deletion of intracellular domains of the glucagon receptor", J. Biol. Chem., 272: pp. 7765 (1997).
Cusi, K. Nonalcoholic fatty liver disease in type 2 diabetes mellitus. Curr Opin Endocrinol Diabetes Obes 16, 141-149, doi:10.1097/Med.0b013e3283293015 (2009).
Cuthbertson, D. J. et al. Improved glycaemia correlates with liver fat reduction in obese, type 2 diabetes, patients given glucagon-like peptide-1 (GLP-1) receptor agonists. PLoS One 7, e50117, doi:10.1371/journal.pone.0050117 (2012).
Degn, K. B. et al. One week's treatment with the long-acting glucagon-like peptide 1 derivative liraglutide (NN2211) markedly improves 24-h glycemia and alpha- and beta-cell function and reduces endogenous glucose release in patients with type 2 diabetes. Diabetes 53, 1187-1194 (2004).

(Continued)

*Primary Examiner* — Jeanette M Lieb
(74) *Attorney, Agent, or Firm* — Bryan D. Zerhusen, Esq.; Nicholas R. Herrel, Esq.; Cantor Colburn LLP

(57) ABSTRACT

The present disclosure relates to a pro-drug peptide, or a salt thereof, having improvement for at least one biological property relative to a parent peptide or peptidomimetic, wherein the biological property is selected from the group consisting of therapeutic index, stability, solubility, toxicity, adsorption, and pre-systemic metabolism. The pro-drug peptide comprising the following structure: Z-pep, wherein: pep is the parent peptide or peptidomimetic; Z is a sequence of n amino acids, Z is cleaved in vivo releasing pep; n≥2 amino acids. The present disclosure also relates to methods of making and using the pro-drug peptide of the present disclosure. For example, the present disclosure describes a pro-drug peptide that may be used to prevent, treat, or ameliorate at least one symptom of hypoglycemia or a hypoglycemia-related disease or disorder.

29 Claims, 44 Drawing Sheets

Specification includes a Sequence Listing.

(56) References Cited

OTHER PUBLICATIONS

Denton, E. V. et al. A β-Peptide Agonist of the GLP-1 Receptor, a Class B GPCR. Org. Lett. 15, 5318-5321 (2013).
Ding, X., Saxena, N. K., Lin, S., Gupta, N. A. & Anania, F. A. Exendin-4, a glucagon-like protein-1 (GLP-1) receptor agonist, reverses hepatic steatosis in ob/ob mice. Hepatology 43, 173-181, doi:10.1002/hep.21006 (2006).
Drucker, D. J. The biology of incretin hormones. Cell Metab 3, 153-165, doi:10.1016/j.cmet.2006.01.004 (2006).
Drucker, D. The Cardiovascular Biology of Glucagon-like Peptide-1. Cell Metab. 24, 15-30 (2016).
Drucker, D.J., Mechanisms of Action and Therapeutic Application of Glucagon-like Peptide-1, Cell Metabolism Review, 27, Apr. 13, 2018, 741-756.
Fagone, P. et al. Emerging therapeutic targets for the treatment of hepatic fibrosis. Drug Discov Today 21, 369-375, doi:10.1016/j.drudis.2015.10.015 (2016).
Fosgerau, K. & Hoffmann, T. Peptide therapeutics: current status and future directions. Drug Discov. Today 20, 122-128 (2015).
Gallwitz, B. et al. Structure/Activity Characterization of Glucagon-Like Peptide-1. FEBS J. 225, 1151-1156 (1994).
Gao, H. et al. The Glucagon-Like Peptide-1 Analogue Liraglutide Inhibits Oxidative Stress and Inflammatory Response in the Liver of Rats with Diet-Induced Non-alcoholic Fatty Liver Disease. Biol Pharm Bull 38, 694-702, doi:10.1248/bpb.b14-00505 (2015).
Gram, H., et al., "Novel Approach for High Level Production of a Recombinant Human Parathyroid Hormone Fragment in *Escherichia Coli*", Biotechnology, vol. 12, No. 10, (1994), Oct. 1, 1994, pp. 1017-1023.
Hager, M. V., Johnson, L. M., Wootten, D., Sexton, P. M. & Gellman, S. H. β-Arrestin-Biased Agonists of the GLP-1 Receptor from β-Amino Acid Residue Incorporation into GLP-1 Analogues. J. Am. Chem. Soc. 138, 14970-14979 (2016).
Hanna, A., Connelly, K. A., Josse, R. G. & McIntyre, R. S. The non-glycemic effects of incretin therapies on cardiovascular outcomes, cognitive function and bone health. Expert Rev. Endocrinol. Metab. 10, 101-114 (2015).
Henninot, A., Collins, J. C. & Nuss, J. M. The Current State of Peptide Drug Discovery: Back to the Future? J. Med. Chem. 2018, 61, 1382-1414 doi:10.1021/acs.jmedchem.7b00318.
Hupe-Sodmann, K. et al. Characterisation of the processing by human neutral endopeptidase 24.11 of GLP-1(7-36) amide and comparison of the substrate specificity of the enzyme for other glucagon-like peptides. Regul. Pept. 58, 149-156 (1995).
Jazayeri, A. et al. Crystal structure of the GLP-1 receptor bound to a peptide agonist. Nature 546, 254-258 (2017).
Jessen, L. et al. Suppression of Food Intake by Glucagon-Like Peptide-1 Receptor Agonists: Relative Potencies and Role of Dipeptidyl Peptidase-4. Endocrinology 153, 5735-5745 (2012).
Johnson, L. M. et al. A Potent α/β-Peptide Analogue of GLP-1 with Prolonged Action in Vivo. J. Am. Chem. Soc. 136, 12848-12851 (2014).
Jouihan, H. et al. Superior reductions in hepatic steatosis and fibrosis with co-administration of a glucagon-like peptide-1 receptor agonist and obeticholic acid in mice. Mol Metab 6, 1360-1370, doi:10.1016/j.molmet.2017.09.001 (2017).
Kaspar, A. A. & Reichert, J. M. Future directions for peptide therapeutics development. Drug Discov. Today 18, 807-817 (2013).
Kreymann, B., Williams, G., Ghatei, M. A. & Bloom, S. R. Glucagon-like peptide-1 7-36: a physiological incretin in man. Lancet 2, 1300-1304 (1987).
Lau, J. et al. Discovery of the Once-Weekly Glucagon-Like Peptide-1 (GLP-1) Analogue Semaglutide. J. Med. Chem. 58, 7370-7380 (2015).
Leech, C. A. et al. Molecular physiology of glucagon-like peptide-1 insulin secretagogue action in pancreatic beta cells. Prog Biophys Mol Biol 107, 236-247, doi:10.1016/j.pbiomolbio.2011.07.005 (2011).

Madsbad, S. et al. An overview of once-weekly glucagon-like peptide-1 receptor agonists-available efficacy and safety data and perspectives for the future. Diabetes Obes Metab 13, 394-407, doi:10.1111/j.1463-1326.2011.01357.x (2011).
Madsbad, S. Review of head-to-head comparisons of glucagon-like peptide-1 receptor agonists. Diabetes Obes. Metab. 18, 317-332 (2016).
Madsbad, S. The role of glucagon-like peptide-1 impairment in obesity and potential therapeutic implications. Diabetes Obes. Metab. 16, 9-21 (2014).
Mcbrayer, D. N. & Tal-Gan, Y. Recent Advances in GLP-1 Receptor Agonists for Use in Diabetes Mellitus. Drug Dev Res 78, 292-299, doi:10.1002/ddr.21404 (2017).
Miranda, L. P. et al. Design and Synthesis of Conformationally Constrained Glucagon-Like Peptide-1 Derivatives with Increased Plasma Stability and Prolonged in Vivo Activity. J. Med. Chem. 51, 2758-2765 (2008).
Murage, E. N., Gao, G., Bisello, A. & Ahn, J.-M. Development of Potent Glucagon-like Peptide-1 Agonists with High Enzyme Stability via Introduction of Multiple Lactam Bridges. J. Med. Chem. 53, 6412-6420 (2010).
Nakade, Y., Tsukamoto, K., Iwa, M., Pappas, T. N. & Takahashi, T. Glucagon like peptide-1 accelerates colonic transit via central CRF and peripheral vagal pathways in conscious rats. Auton Neurosci 131, 50-56, doi:10.1016/j.autneu.2006.06.007 (2007).
Nauck, M. A. et al. Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial. Diabetes Obes Metab 9, 194-205, doi:10.1111/j.1463-1326.2006.00704.x (2007).
Nauck, M. A. et al. Five weeks of treatment with the GLP-1 analogue liraglutide improves glycaemic control and lowers body weight in subjects with type 2 diabetes. Exp Clin Endocrinol Diabetes 114, 417-423, doi:10.1055/s-2006-924230 (2006).
Oseini, A. M. & Sanyal, A. J. Therapies in non-alcoholic steatohepatitis (NASH). Liver Int 37 Suppl 1, 97-103, doi:10.1111/liv.13302 (2017).
Potts, J. E. et al. The Effect of Glucagon-Like Peptide 1 Receptor Agonists on Weight Loss in Type 2 Diabetes: A Systematic Review and Mixed Treatment Comparison Meta-Analysis. PLOS ONE 10, e0126769 (2015).
Remington's Pharmaceutical Sciences, 1980, vol. 16, Mack Publishing Company, Easton, Pa., pp. 61 and 424.
Rose, K., et al., "Insulin proteinase liberates from glucagon a fragment known to have enhanced activity against Ca2++AMg2+-dependent ATPase", (1988) Biochemical Journal, vol. 256, pp. 847-851.
Runge, et al., "Different domains of the glucagon and glucagon-like peptide-1 receptors provide the critical determinants of ligand selectivity", Brit. J. Pharmacol., 138: pp. 787-794 (2003).
Runge, S., Thøgersen, H., Madsen, K., Lau, J. & Rudolph, R. Crystal Structure of the Ligand-bound Glucagon-like Peptide-1 Receptor Extracellular Domain. J. Biol. Chem. 283, 11340-11347 (2008).
Sathyanarayana, P. et al. Effects of combined exenatide and pioglitazone therapy on hepatic fat content in type 2 diabetes. Obesity (Silver Spring) 19, 2310-2315, doi:10.1038/oby.2011.152 (2011).
Sharma, S., Mells, J. E., Fu, P. P., Saxena, N. K. & Anania, F. A. GLP-1 analogs reduce hepatocyte steatosis and improve survival by enhancing the unfolded protein response and promoting macroautophagy. PLoS One 6, e25269, doi:10.1371/journal.pone.0025269 (2011).
Siegel et al. Comparison of the effect of native glucagon-like peptide 1 and dipeptidyl peptidase IV-resistant analogues on insulin release from rat pancreatic islets. Eur. J. Clin. Invest. 29, 610-614 (1999).
Siegel, E. G. et al. Biological activity of GLP-1-analogues with N-terminal modifications. Regul. Pept. 79, 93-102 (1999).
Tang-Christensen, M. & Cowley, M. A. GLP-1 analogs: satiety without malaise? Am J Physiol Regul Integr Comp Physiol 293, R981-982, doi:10.1152/ajpregu.00449.2007 (2007).
Townsend, S. A. & Newsome, P. N. Review article: new treatments in non-alcoholic fatty liver disease. Aliment Pharmacol Ther 46, 494-507, doi:10.1111/apt.14210 (2017).

(56) References Cited

OTHER PUBLICATIONS

Trevaskis, J. L. et al. Glucagon-like peptide-1 receptor agonism improves metabolic, biochemical, and histopathological indices of nonalcoholic steatohepatitis in mice. Am J Physiol Gastrointest Liver Physiol 302, G762-772, doi:10.1152/ajpgi.00476.2011 (2012).
Tushuizen, M. E. et al. Incretin mimetics as a novel therapeutic option for hepatic steatosis. Liver Int 26, 1015-1017, doi:10.1111/j.1478-3231.2006.01315.x (2006).
Underwood, C. R. et al. Crystal Structure of Glucagon-like Peptide-1 in Complex with the Extracellular Domain of the Glucagon-like Peptide-1 Receptor. J. Biol. Chem. 285, 723-730 (2010).
Valeur, E. et al. New Modalities for Challenging Targets in Drug Discovery. Angew. Chem. Int. Ed. 56, 10294-10323 (2017).
Vilsboll, T., Christensen, M., Junker, A. E., Knop, F. K. & Gluud, L. L. Effects of glucagon-like peptide-1 receptor agonists on weight loss: systematic review and meta-analyses of randomised controlled trials. BMJ 344, d7771, doi:10.1136/bmj.d7771 (2012).
Wang, J., Yadav, V., Smart, A. L., Tajiri, S. & Basit, A. W. Toward Oral Delivery of Biopharmaceuticals: An Assessment of the Gastrointestinal Stability of 17 Peptide Drugs. Mol. Pharm. 12, 966-973 (2015).
Wang, X. C., Gusdon, A. M., Liu, H. & Qu, S. Effects of glucagon-like peptide-1 receptor agonists on non-alcoholic fatty liver disease and inflammation. World J Gastroenterol 20, 14821-14830, doi:10.3748/wjg.v20.i40.14821 (2014).
Xiao, Q. et al. Biological Activities of Glucagon-Like Peptide-1 Analogues in Vitro and in Vivo. Biochemistry 40, 2860-2869 (2001).
Yang, X., et al., "Long-acting GLP-1 analogue in V-shaped conformation by terminal polylysine modifications", Molecular Pharmaceutics., vol. 11, No. 11, (2014), Nov. 3, 2014, pp. 4092-4099.
Zhang, Y. et al. Cryo-EM structure of the activated GLP-1 receptor in complex with a G protein. Nature 546, 248-253 (2017).
International Preliminary Report on Patentability for PCT/IB2018/000838, dated Dec. 31, 2019.
International Search Report and Written Opinion for PCT/IB2018/000838, dated Jan. 8, 2019.
Miller, et al., The Class B G-Protein-Coupled GLP-1 receptor: an important target for the treatment of type-2 diabetes mellitus, International Journal of Obesity Supplements, vol. 4:S9-S13 (Year Jul. 2014).

\* cited by examiner

FIG. 1

Peptide/SEQ ID NO:

| Peptide/SEQ ID NO: | Sequence |
|---|---|
| 10/1 (Glucagon) | H S Q G T F T S D Y S K Y L D S R R A Q D F V Q W L M N T |
| 11/14 | H S Q G T F T S D Y S K Y L D S R R A Q D F V Q W L M N T |
| 12/15 | K P H S Q G T F T S D Y S K Y L D S R R A Q D F V Q W L L N T |
| 13/16 | K P K P H S Q G T F T S D Y S K Y L D S R R A Q D F V Q W L L N T |
| 14/17 | K P K P K P H S Q G T F T S D Y S K Y L D S R R A Q D F V Q W L M N T |
| 15/18 | K P H S Q G T F T S D Y S K Y L D S R R A Q D F V Q W L L N T |
| 16/19 | K P K P H S Q G T F T S D Y S K Y L D S R R A Q D F V Q W L M N T |
| 17/20 | K P K P K P H S Q G T F T S D Y S K Y L D S R R A Q D F V Q W L L N T |
| 18/21 | E P H S Q G T F T S D Y S K Y L D S R R A Q D F V Q W L L N T |
| 19/22 | K K K K K P H S Q G T F T S D Y S K Y L D S R R A Q D F V Q W L L N T |
| 20/23 | K K K K K P H S Q G T F T S D Y S K Y L D S R R A Q D F V Q W L M N T |
| 21/24 | K K K K K P H S Q G T F T S D Y S K Y L D S R R A Q D F V Q W L M N T |
| 22/25 | BAdo BAdo K P H S Q G T F T S D Y S K Y L D S R R A Q D F V Q W L L N T |
| 23/26 | BAdo BAdo K P H S Q G T F T S D Y S K Y L D S R R A Q D F V Q W L L N T |
| 24/27 | K P K P P K* P H S Q G T F T S D Y S K Y L D S R R A Q D F V Q W L M N T |
| 25/28 | K P K P P K* P H S Q G T F T S D Y S K Y L D S R R A Q D F V Q W L M N T |

PRO-DRUG PEPTIDE WITH IMPROVED PHARMACEUTICAL PROPERTIES

CROSS-REFERENCE TO RELATED APPLICATIONS

The present disclosure claims priority to U.S. Provisional Patent Application No. 62/526,678, filed 29 Jun. 2017, entitled "PRO-DRUG PEPTIDE WITH IMPROVED PHARMACEUTICAL PROPERTIES", which is hereby incorporated by reference in its entirety for all purposes.

INCORPORATION BY REFERENCE

An electronic version of the Sequence Listing file name: 1513195_131US2_Sequence_Listing_26JUN2018_ST25.txt, size: 13.0 KB containing SEQ ID NOs: 1-31 is filed herewith, and is hereby incorporated by reference in its entirety.

BACKGROUND

1. Field of the Discovery

The present disclosure relates to pro-drug peptides, making the same, and using the same for treating diseases. In particular, the present disclosure relates to a pro-drug peptide that includes a parent peptide or peptidomimetic and a pro-drug portion that includes at least two amino acids that are cleaved in vivo, releasing the parent peptide or peptidomimetic.

2. Background Information

Pro-drugs are compounds that are metabolized by the subject after administration to form a pharmaceutically active compound or drug. The general object of a prodrug is to mask undesirable properties. For example, irritation or pain after local administration, chemical instability, low target selectively, low solubility in water or lipid membranes, toxicity, pre-systemic metabolism, among others. As such, pro-drug modifications are designed to optimize, inter alia, adsorption, distribution, metabolism, excretion, and/or unwanted toxicity of a parent compound or drug. As a result, prodrugs are used, inter alia, to optimize therapeutic index, decrease toxicity, improve adsorption, decrease pre-systemic metabolism, improve solubility and improve chemical stability.

Pro-drugs can be classified into two general categories: Type 1 and Type II pro-drugs. Type I pro-drugs (e.g., anti-viral nucleoside analogs) are pro-drugs that are bioactivated intracellularly with Type IA being metabolized at the cellular targets of their therapeutic action and Type IB being converted by metabolic tissues (e.g., the liver). Type II pro-drugs (e.g., salicin) are bioactivated extracellularly with Type IIA being converted in the gastrointestinal fluid, Type IIB being converted in extracellular fluid compartments (e.g., circulatory system), and Type IIC being converted near or inside therapeutic targets/cells.

Glucagon is a 29 amino acid peptide hormone that is produced by pancreatic alpha-cells in response to low blood glucose levels, thereby stimulating glycogenolysis (i.e., the breakdown of glycogen [n] to glucose-6-phosphate and glycogen [n−1]) and gluconeogenesis (i.e., the synthesis of glucose from non-carbohydrate carbon substrates), and inhibiting glycogenesis (i.e., the synthesis of glycogen from sugar). As a result, there is a rapid increase in blood glucose.

Because of insulins low therapeutic index, insulin-dependent diabetes is a well-known risk factor for severe hypoglycaemia, where blood glucose levels can fall below 50 mg/dl. The standard treatment for hypoglycaemia (such as severe insulin-induced hypoglycaemia) is acute subcutaneous administration of glucagon. Because of glucagon's poor chemical stability, however, glucagon is supplied in a lyophilized powder that is prepared immediately prior to administration. Furthermore, because of glucagon's poor aqueous solubility at physiological pH, the solution for administration is prepared with dilute aqueous hydrochloric acid. Also because of glycogen's chemical instability, the dilute hydrochloric acid prepared glucagon must be used immediately.

Thus, there exists a need for a method of making therapeutics with enhanced chemical stability, aqueous solubility, therapeutic index, and adsorption, as well as decreased toxicity and pre-systemic metabolism. For example, there exists a need for a pro-drug of glucagon that has enhanced chemical stability and aqueous solubility at physiological pH, relative to the parent peptide glucagon, for use as a therapeutic intervention, e.g., hypoglycaemia.

SUMMARY

The present description provides therapeutic compositions and methods of making and using the same that are based on the surprising and unexpected discovery that chemically modified peptides as described herein have improvement for at least one biological property (such as, a biological property whose improvement enhances its therapeutic effect) relative to a parent peptide or peptidomimetic (i.e., the unmodified peptide). The modified peptides or peptidomimetic as described herein include a pro-drug portion that is cleaved in vivo, after administration, to release the parent peptide or peptidomimetic. The described peptides and compositions comprising effective amounts of the same are effective for treating, preventing and/or ameliorating the symptoms of diseases and disorders that are treated, prevented, or ameliorated by the release of the parent peptide or peptidomimetic (for example, the release of glucagon or an analog thereof to treat a hypoclycemia related disease or disorder). Accordingly, in certain additional aspects, the disclosure provides methods of making and using the described peptides and compositions comprising the same for the treatment, prevention and/or amelioration of the symptoms a hypoglycemia relates disease or disorder.

Thus, in an aspect, the present disclosure provides a pro-drug peptide or a salt thereof (e.g., a pharmaceutical salt thereof) having improvement for at least one biological property relative to a parent peptide or peptidomimetic, wherein the biological property is selected from the group consisting of therapeutic index, stability, solubility, toxicity, adsorption, and pre-systemic metabolism, the pro-drug peptide comprising the following structure:

$$Z_n\text{-pep},$$

wherein: pep is the parent peptide or peptidomimetic; Z is a pro-drug portion, e.g., an amino acid sequence of n amino acids, wherein Z is cleaved in vivo releasing pep; and n is an integer $\geq 2$ amino acids.

In some embodiments, the Z has the following structure: $(\text{Glu-Pro})_m$ or $(\text{Lys-Pro})_X$, wherein X is an integer $\geq 1$.

In certain embodiments, at least the first Lys of Z is functionalized with a soluble compound or moiety.

In particular embodiments, at least two Lys of Z are functionalized with a soluble compound or moiety.

In other embodiments, the Z comprises two amino acids, and the first amino acid is functionalized with a soluble compound or moiety.

In additional embodiments, the soluble compound is hydrophilic or soluble in aqueous solution.

In further embodiments, the Z is selected from the group consisting of EP, KP, EPEP, KPKP, EPEPEP, and KPKPKP.

In certain other embodiments, the first amino acid of Z is functionalized with a soluble compound or moiety comprising: 12-aminododecanoic acid (Ado), Ado-Ado-(Lys)$_m$, 8-amino-3,6-dioxaoctanoic acid (8Ado), 8Ado-8Ado-(Lys)$_m$, (Lys)$_m$, or (Pro-Lys)$_m$, wherein m is an integer from 0-10.

In some embodiments, at least two Lys of Z are functionalized with a soluble compound or moiety comprising: Ado, Ado-Ado-(Lys)$_m$, 8Ado, 8Ado-8Ado-(Lys)$_m$, (Lys)$_m$, or (Pro-Lys)$_m$, wherein m is an integer from 0-10.

In particular embodiments, the c-terminus of the peptide is amine modified or amidated.

In another embodiment, the parent peptide or peptidomimetic has an amino acid sequence that is at least 85% identical to a sequence selected from the group consisting of SEQ ID NO: 1 (HSQGTFTSDYSKYLDSR-RAQDFVQWLMNT) and SEQ ID NO: 2 (HSQGTFTSDYSKYLDSRRAQDFVQWLLNT).

According to another aspect, a pharmaceutical composition is provided that comprises an effective amount of at least one pro-drug of the present disclosure, and a pharmaceutically acceptable excipient or carrier. In certain additional aspects, the description provides therapeutic compositions comprising an effective amount of at least one pro-drug peptide of the present disclosure, and an effective amount of at least one additional bioactive agent. In certain embodiments, the composition further comprises an excipient or carrier as described herein.

According to yet another aspect, the present disclosure provides a method of treating or preventing hypoglycemia or a hypoglycemia related disorder or disease. The method comprises: administering an effective amount of the pro-drug peptide of the present disclosure or the pharmaceutical composition of the present disclosure, wherein the pro-drug peptide is effective at treating or preventing hypoglycemia or the hypoglycemia related disorder or disease.

According to a further aspect, the present disclosure provides a method of preparing a pro-drug peptide or salt thereof (e.g., a pharmaceutical salt thereof) having improved biological property or properties (e.g., at least one biological property selected from the group consisting of therapeutic index, stability, solubility, toxicity, adsorption, and pre-systemic metabolism) relative to a parent peptide or peptidomimetic. The method comprises: adding a pro-drug portion to the parent peptide or peptidomimetic (e.g., synthesizing the pro-drug portion and the peptide or peptidomimetic as a contiguous sequence by any method known or that becomes known to those skilled in the art), wherein the pro-drug portion comprises ≥2 amino acids that are cleaved in vivo releasing the peptide or peptidomimetic.

In particular embodiments, the pro-drug portion is located at the amino-terminus of the parent peptide or peptidomimetic. In other embodiments, the pro-drug portion is located at the carboxyl-terminus of the parent peptide or peptidomimetic.

In some embodiments, the pro-drug portion has the following structure: (Glu-Pro)$_m$ or (Lys-Pro)$_X$, wherein X is an integer ≥1.

In certain embodiments, at least the first Lys of the pro-drug portion is functionalized with a soluble compound.

In additional embodiments, at least two Lys of the pro-drug portion are functionalized with a soluble compound.

In particular embodiments, the pro-drug portion comprises two amino acids, and the first amino acid is functionalized with a soluble compound.

In other embodiment, the soluble compound is aqueously soluble.

In an embodiment, the pro-drug portion is selected from the group consisting of EP, KP, EPEP, KPKP, EPEPEP, and KPKPKP.

In yet other embodiments, the first amino acid of the pro-drug portion is functionalized with a soluble compound or moiety comprising: 12-aminododecanoic acid (Ado), Ado-Ado-(Lys)$_m$, 8-amino-3,6-dioxaoctanoic acid (8Ado), 8Ado-8Ado-(Lys)$_m$, (Lys)$_m$, or (Pro-Lys)$_m$, wherein m is an integer from 0-10.

In some embodiments, at least two Lys of the pro-drug portion is functionalized with a soluble compound or moiety comprising: Ado, Ado-Ado-(Lys)$_m$, 8Ado, 8Ado-8Ado-(Lys)$_m$, (Lys)$_m$, or (Pro-Lys)$_m$, wherein m is an integer from 0-10.

In yet other embodiments the parent peptide or peptidomimetic has an amino acid sequence that is at least 85% identical to a sequence selected from the group consisting of SEQ ID NO: 1 (HSQGTFTSDYSKYLDSR-RAQDFVQWLMNT) and SEQ ID NO: 2 (HSQGTFTSDYSKYLDSRRAQDFVQWLLNT).

In other embodiments, the method further comprises amidating the c-terminus of the peptide.

In another embodiment, the method further comprises modifying the c-terminus of the protein with an amine.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

Figure 1:
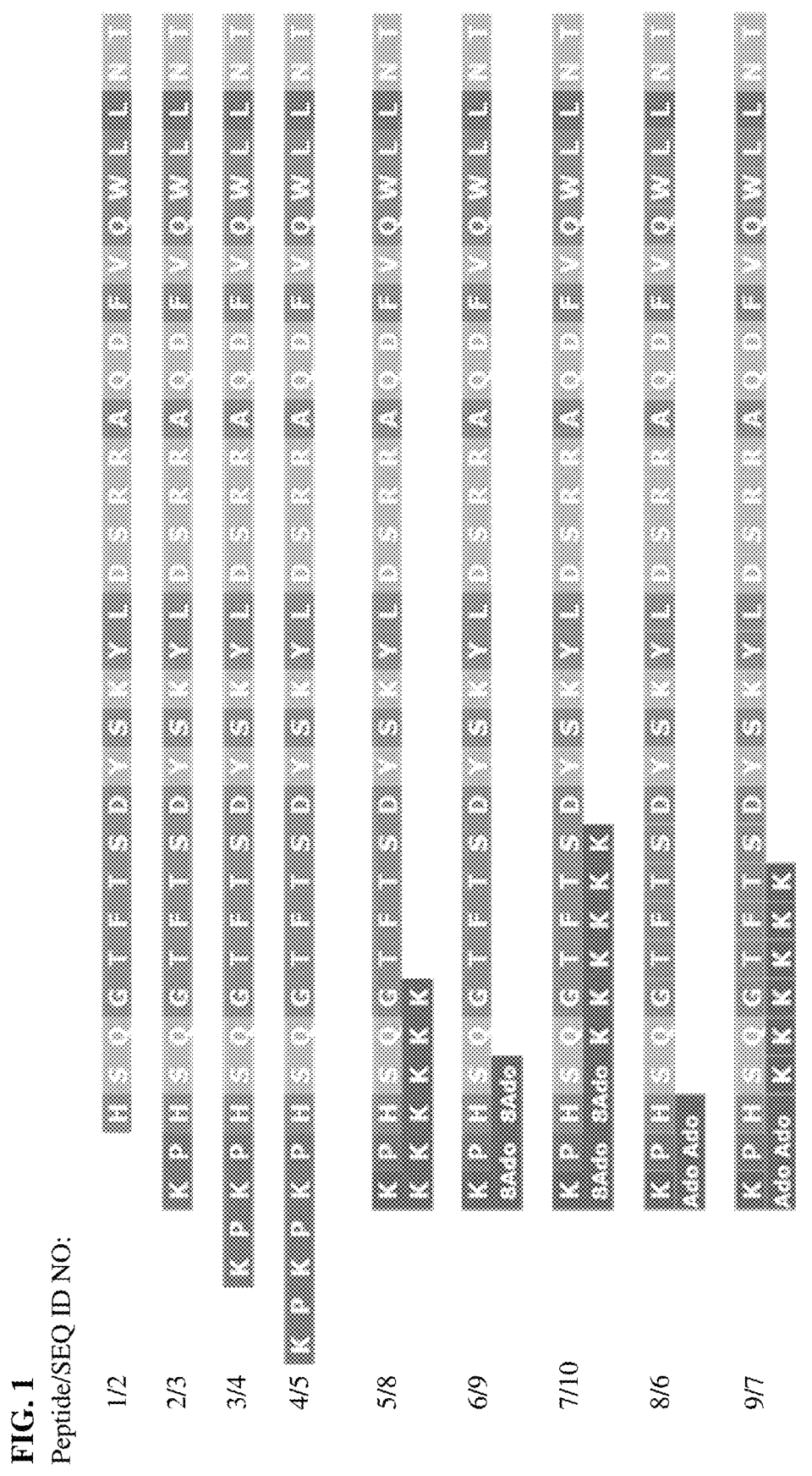

FIG. 1. Illustrates and aligns peptides 1-9, which includes a parent peptide and several exemplary pro-drugs including the same.

FIG. 11A and FIG. 11B. (A) Illustrates and aligns of peptides 10-25, which includes the parent peptide and several exemplary pro-drugs including the same. (B) Illustrates the chemical structure of the modified lysines illustrated in FIG. 11A, wherein when K* is the N-terminus one skilled in the art appreciates that a hydrogen is bound to the nitrogen on the left side of the chemical structure.

DETAILED DESCRIPTION

Figure 2:
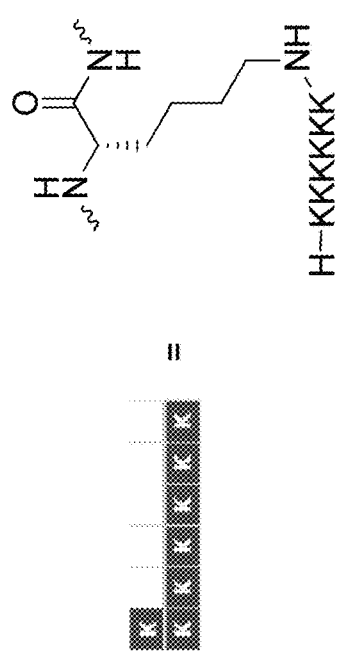
FIG. 2. Illustrates an exemplary functionalization of a Lys with Lys-Lys-Lys-Lys-Lys-Lys, wherein when the Lys is at the N-terminus one skilled in the art appreciates that a hydrogen is bound to the nitrogen on the left side of the chemical structure.
Figure 3:
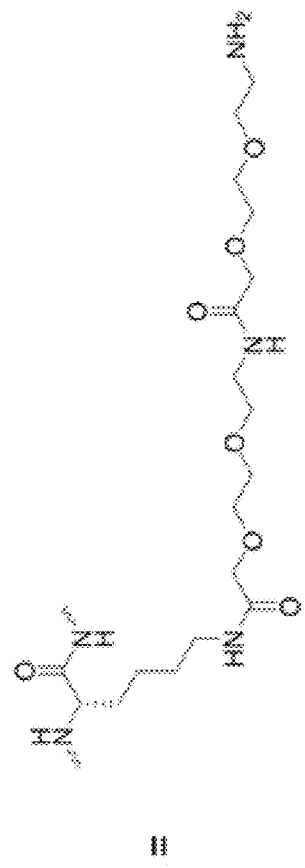
FIG. 3. Illustrates an exemplary functionalization of a Lys with 8Ado-8Ado, wherein when K* is the N-terminus one skilled in the art appreciates that a hydrogen is bound to the nitrogen on the left side of the chemical structure.
Figure 4:
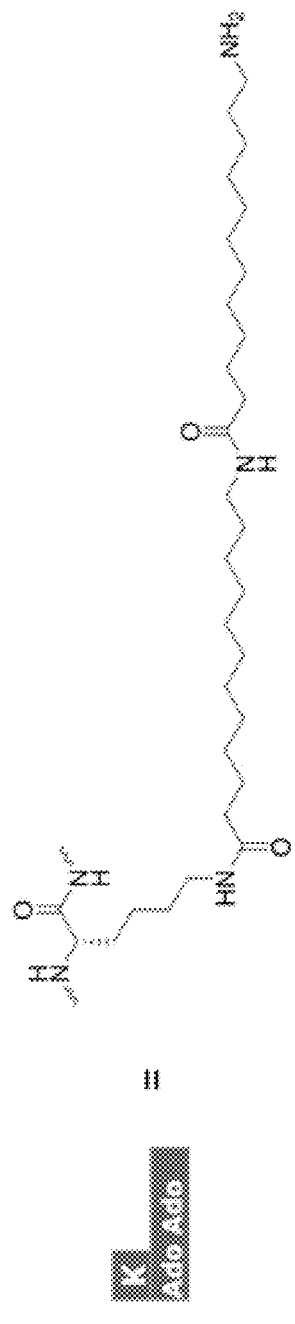
FIG. 4. Illustrates an exemplary functionalization of a Lys with Ado-Ado, wherein when K* is the N-terminus one skilled in the art appreciates that a hydrogen is bound to the nitrogen on the left side of the chemical structure.
Figure 5:
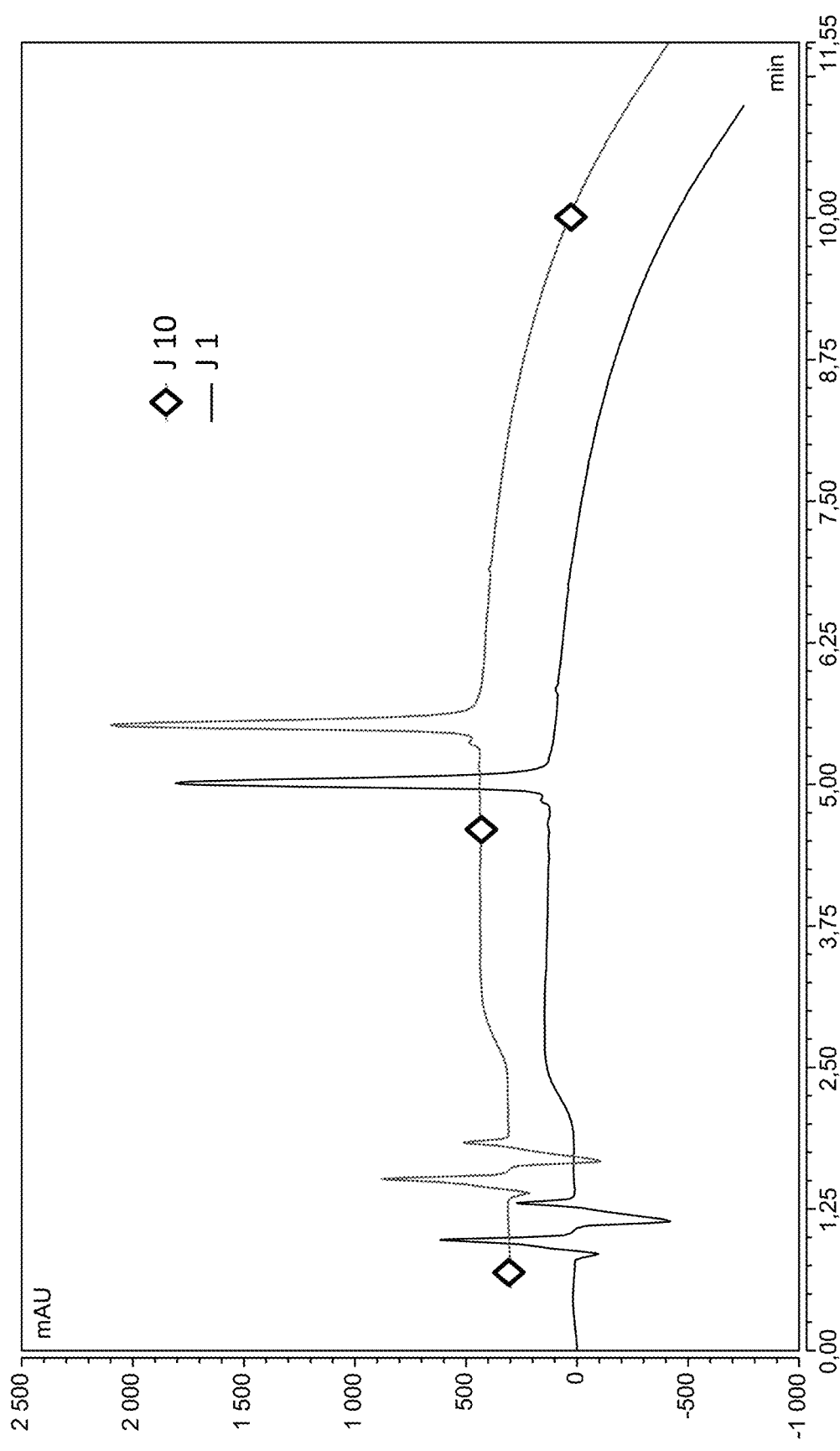
FIG. 5. Stability of peptide 3 (1 mg/mL) in PBS (phosphate buffered saline) at room temperature over 10 days.
Figure 6:
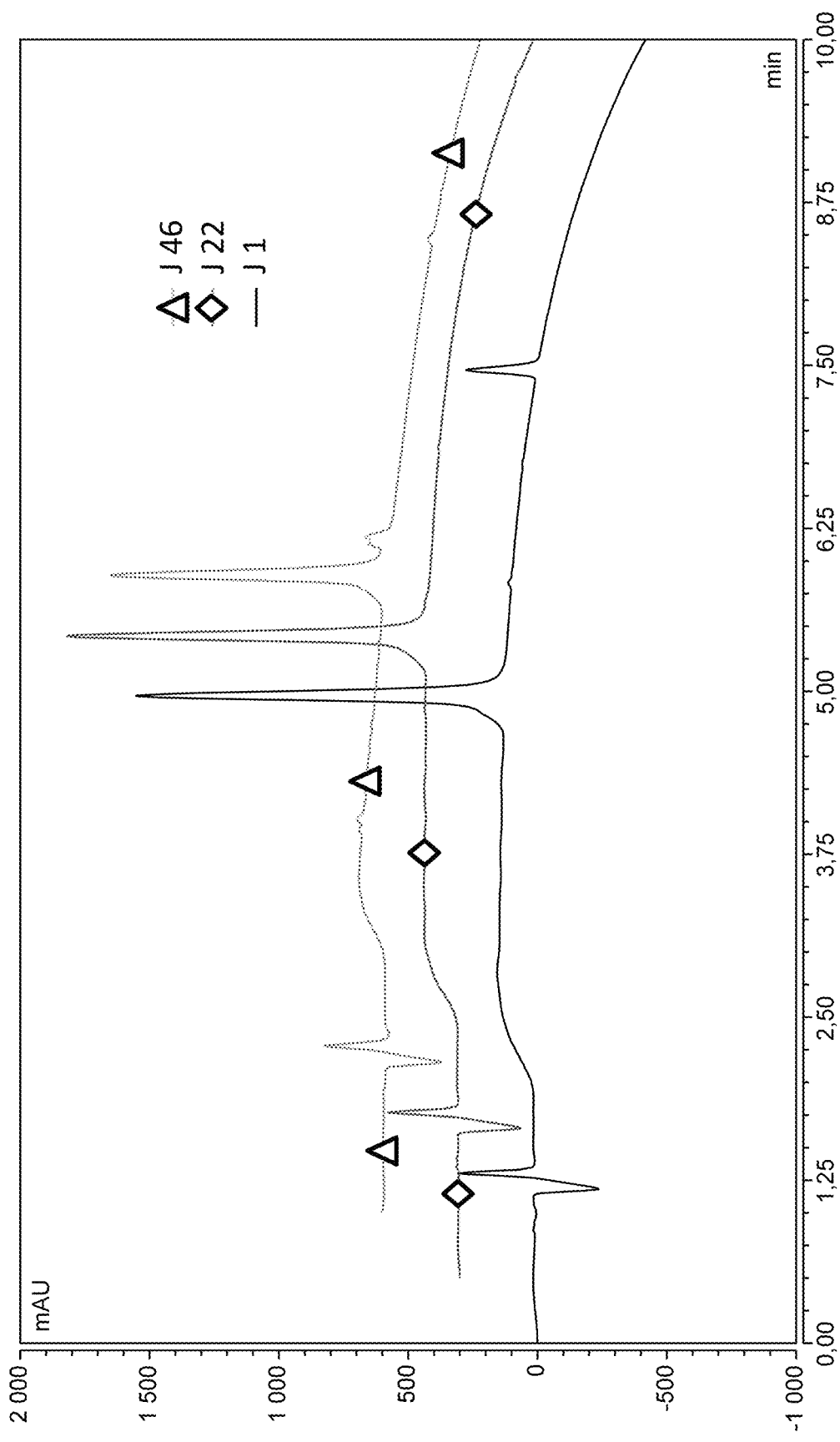
FIG. 6. Stability of peptide 4 (1 mg/mL) in water at room temperature over 46 days.
Figure 7:
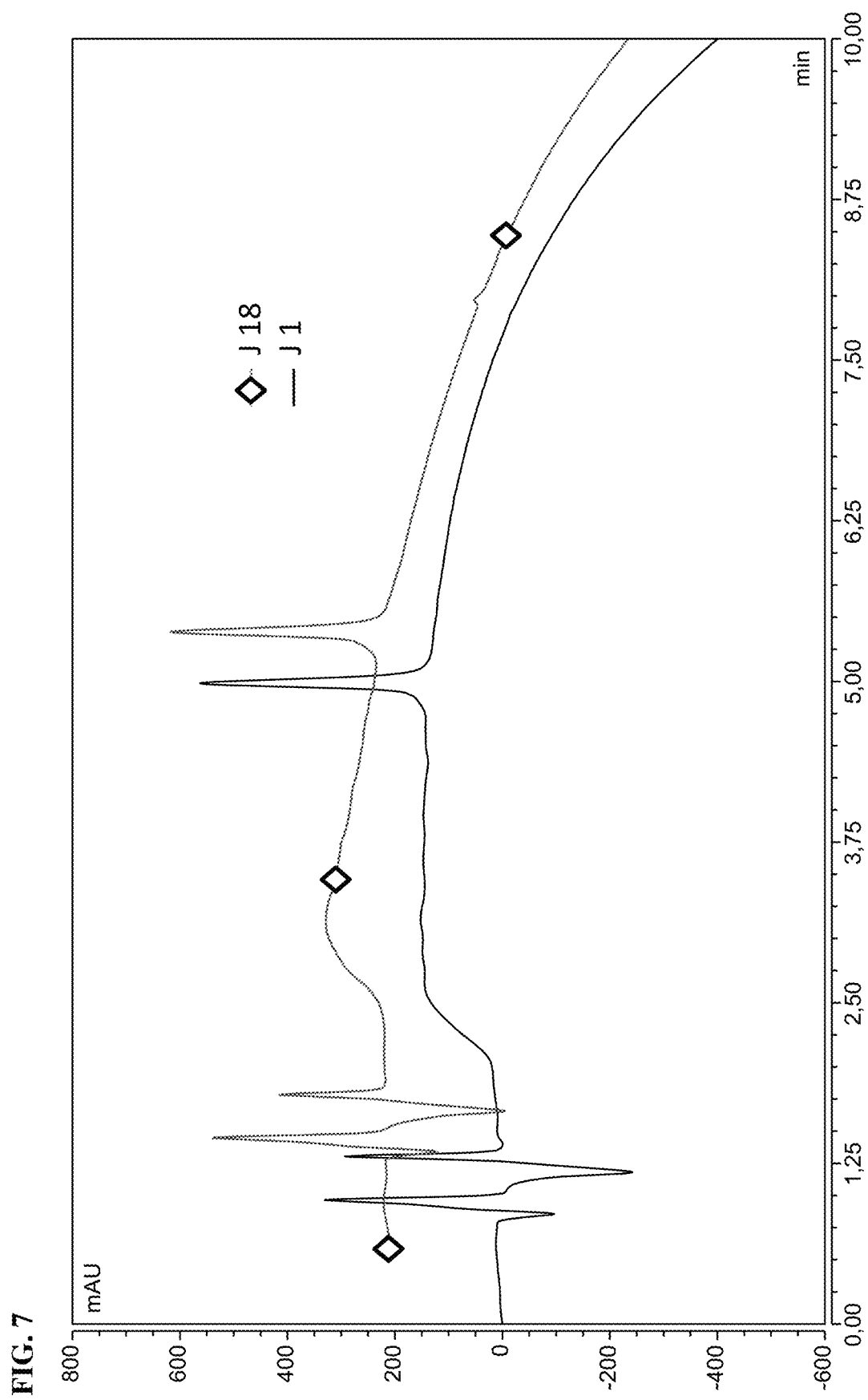
FIG. 7. Stability of peptide 4 (1 mg/mL) in physiological serum at room temperature over 18 days.
Figure 8:
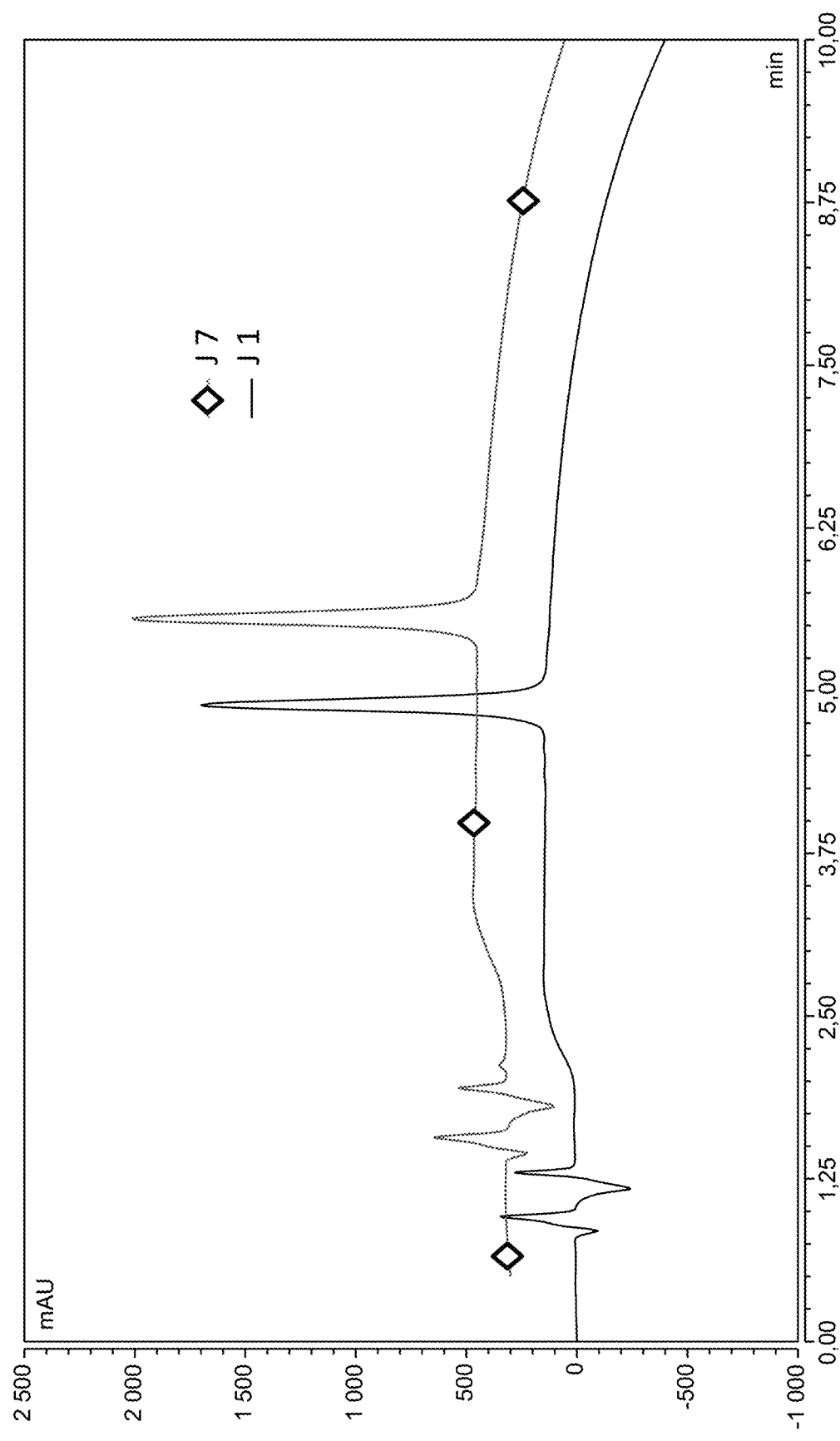
FIG. 8. Stability of peptide 5 (1 mg/mL) in physiological serum at 4° C. over 7 days.
Figure 9:
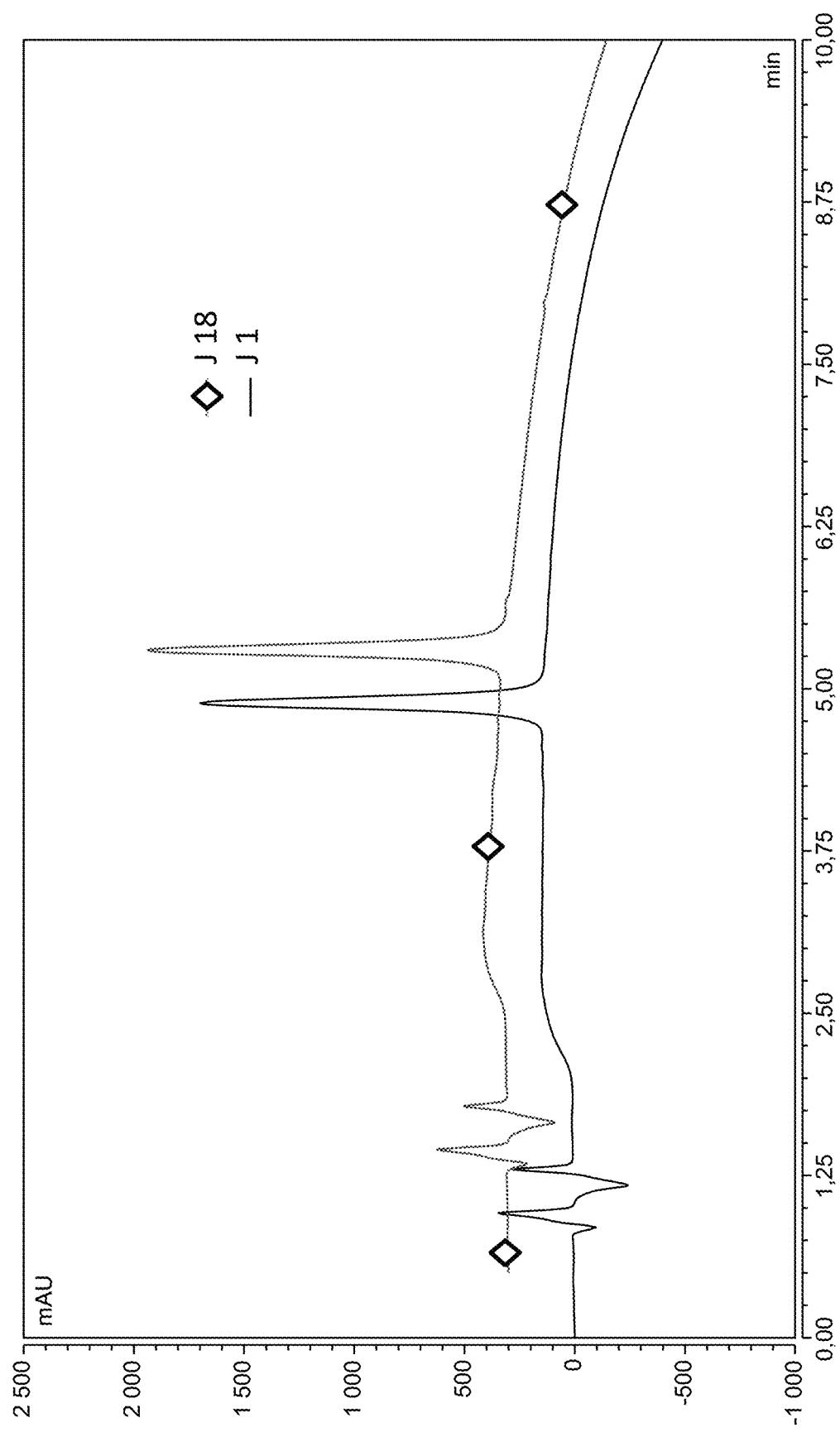
FIG. 9. Stability of peptide 5 (1 mg/mL) in physiological serum at room temperature over 18 days.
Figure 10:
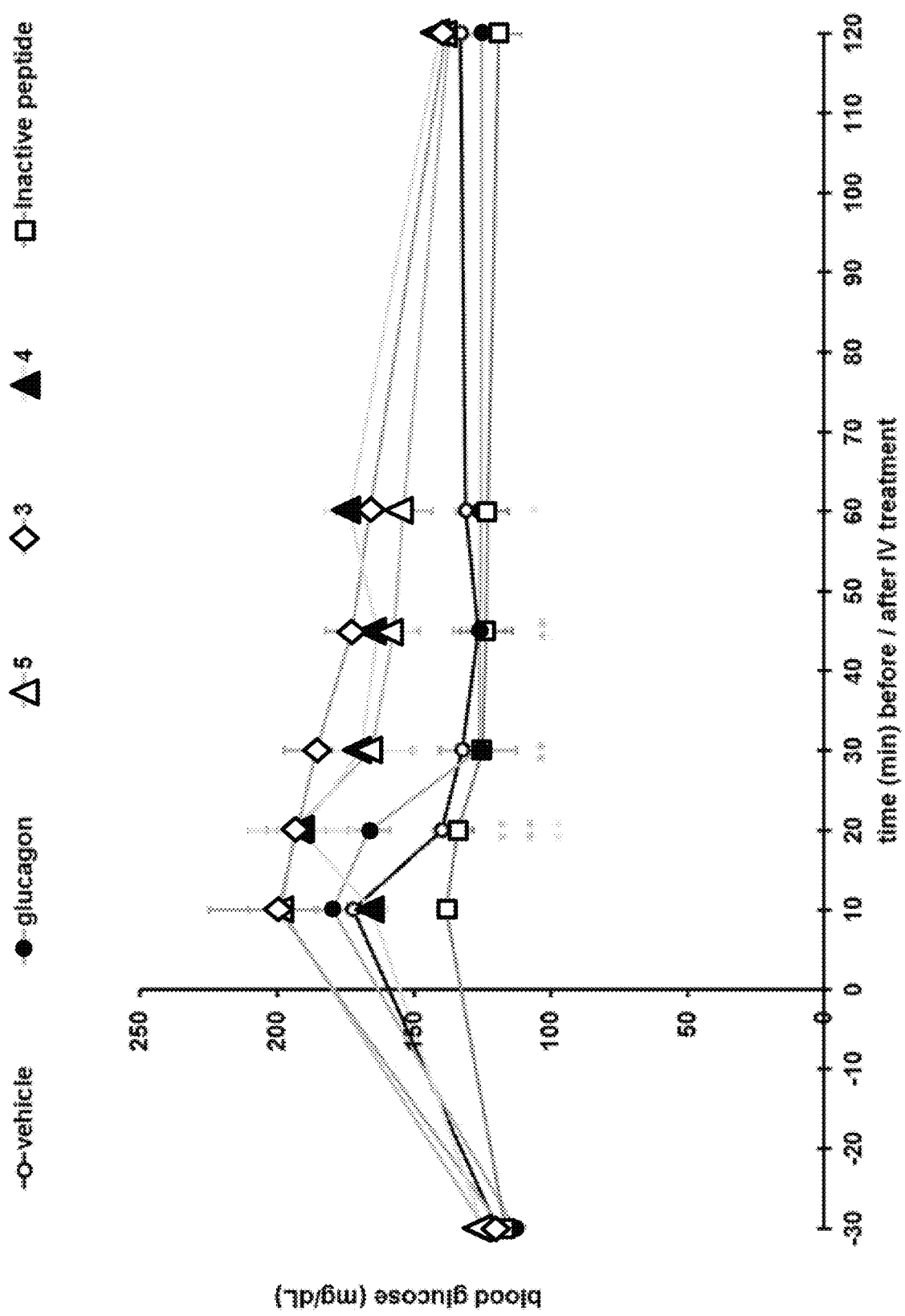
FIG. 10. Blood glucose measurement (mg/dl) 30 min before dosing then at t=10 minutes, 20 minutes, 30 minutes, 45 minutes, 60 minutes, and 120 minutes after injection, * $p<0.05$; ** $p<0.01$: two way anova with Bonferroni posttests.
Figure 11B:
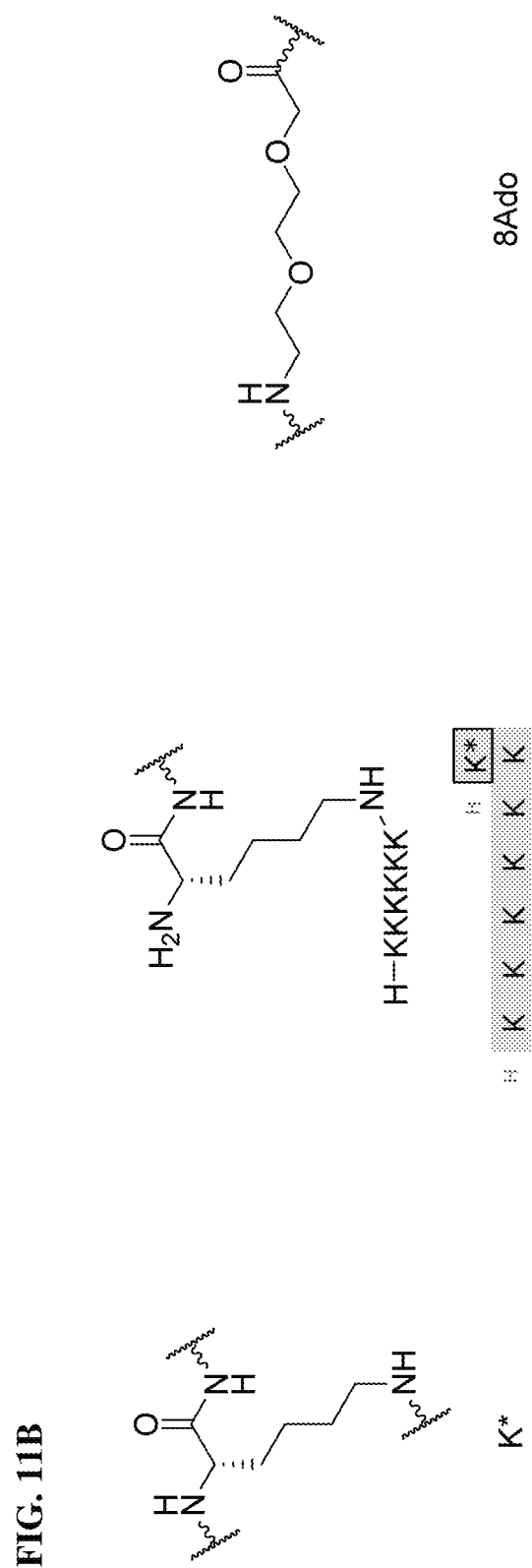

The following is a detailed description of the invention provided to aid those skilled in the art in practicing the present invention. Those of ordinary skill in the art may make modifications and variations in the embodiments described herein without departing from the spirit or scope of the present invention. Although any methods and materials similar or equivalent to those described herein can also be used in the practice or testing of the present invention, the preferred methods and materials are now described. Unless otherwise defined, all technical and scientific terms used herein have the same meaning as commonly understood by one of ordinary skill in the art to which this invention belongs. The terminology used in the present disclosure is for describing particular embodiments only and is not intended to be limiting of the invention. All publications, patent applications, patents, figures and other references mentioned herein are expressly incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure. The upper and lower limits of these smaller ranges which may independently be included in the smaller ranges is also encompassed within the present disclosure, subject to any specifically excluded limit in the stated range. Where the stated range includes one or both of the limits, ranges excluding either both of those included limits are also included in the present disclosure.

As used herein, the following terms may have meanings ascribed to them below, unless specified otherwise. However, it should be understood that other meanings that are known or understood by those having ordinary skill in the art to which the present disclosure belongs are also possible, and within the scope of the present disclosure.

It must be noted that as used herein and in the appended claims, the singular forms "a", "and", and "the" include plural references (i.e., refer to one or to more than one or at least one) to the grammatical object of the article. By way of example, "an element" means one element or more than one element.

The term "about" as it is used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or", as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, e.g. an agent that stimulates glycogenolysis, stimulates gluconeogenesis, and/or inhibiting glycogenesis. In particularly preferred aspects, the co-administration of compounds results in synergistic activity and/or therapy, including anti-hypoclycemic activity.

The term "compound", "peptide", and "peptidomimetic", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder.

The term "derivatives" can mean, but is in no way limited to, chemical compositions, for example, nucleic acids, nucleotides, polypeptides or amino acids, formed from the native compounds either directly, by modification, or by partial substitution. The term "analogs" can mean, but is in no way limited to, chemical compositions, for example, nucleic acids, nucleotides, polypeptides or amino acids that have a structure similar to, but not identical to, the native compound.

The term "effective amount/dose," "pharmaceutically effective amount/dose," "pharmaceutically effective amount/dose" or "therapeutically effective amount/dose" can mean, but is in no way limited to, that amount/dose of the active pharmaceutical ingredient sufficient to prevent, inhibit the occurrence, ameliorate, delay or treat (alleviate a symptom to some extent, preferably all) at least one symptom of a condition, disorder or disease state. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. For any compound used in the method of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "pharmacological composition," "therapeutic composition," "therapeutic formulation" or "pharmaceutically acceptable formulation" can mean, but is in no way limited to, a composition or formulation that allows for the effective distribution of an agent provided by the present disclosure, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "local administration" refers to a route of administration in which the agent is delivered to a site that is apposite or proximal, e.g., within about 10 cm, to the site of the lesion or disease.

The term "conservative mutations" refers to the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

By "homology" or "identity" is meant the nucleotide sequence of two or more nucleic acid molecules or two or more nucleic acid or amino acid sequences is partially or completely identical. In certain embodiments the homologous nucleic acid or amino acid sequence has 30%, 40%, 50%, 60%, 70%, 80%, 90%, or 95% sequence similarity or identity to the amino acid sequence of SEQ ID NO:1 or SEQ ID NO:2, respectively.

"Homologs" can be naturally occurring, or created by artificial synthesis of one or more nucleic acids (or amino acids resulting therefrom) having related sequences, or by modification of one or more nucleic acid (or amino acids that result therefrom) to produce related nucleic acids. Nucleic acids (and thus the resultant amino acid sequence) are homologous when they are derived, naturally or artificially, from a common ancestor sequence (e.g., orthologs or paralogs). If the homology between two nucleic acids is not expressly described, homology can be inferred by a nucleic acid comparison between two or more sequences (including the amino acid sequences). If the sequences demonstrate some degree of sequence similarity, for example, greater than about 30% at the primary amino acid structure level, it is concluded that they share a common ancestor. For purposes of the present disclosure, nucleic acid sequences are homologous if the sequences are sufficiently similar to allow recombination and/or hybridization under low stringency conditions. In addition, polypeptides are regarded as homologous if their nucleic acid sequences are sufficiently similar to allow recombination or hybridization under low stringency conditions, and optionally they demonstrate similar activity as the parent peptide, and optionally they can be recognized by (i.e., cross-react with) an antibody specific for an epitope contained within the amino acid sequence of the patent peptide, e.g., at least one of SEQ ID NO: 1 or SEQ ID NO: 2.

The term "cell" can mean, but is in no way limited to, it's usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "host cell" can mean, but is in no way limited to, a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "therapeutically effective amount or dose" includes a dose of a drug that is capable of achieving a therapeutic effect in a subject in need thereof. For example, a therapeutically effective amount of a drug can be the amount that is capable of preventing or relieving one or more symptoms associated with a disease or disorder, e.g., tissue injury or muscle-related disease or disorder. The exact amount can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A kit is any manufacture (e.g. a package or container) comprising at least one pro-drug peptide of the present disclosure or pharmaceutical composition of the present disclosure. The manufacture may be promoted, distributed, or sold as a unit for performing the methods of the present disclosure. In addition, the kits of the present disclosure may preferably contain instructions which describe a suitable administration method. Such kits can be conveniently used, e.g., in clinical settings, to treat or ameliorate patients exhibiting symptoms of disease or disorder (such as, a hypoglycemia or hypoglycemia relates disease or disorder).

All publications, patent applications, patents, and other references mentioned herein are incorporated by reference in their entirety. In the case of conflict, the present specification, including definitions, will control. In addition, the materials, methods, and examples are illustrative only and not intended to be limiting.

The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991).

The present description provides therapeutic compositions and methods of using the same that are based on the surprising and unexpected discovery that the chemically modified peptides or peptidomimetics as described herein have improved one or more biological properties. In particular, the pro-drug peptide of the present disclosure includes improvement in at least one biological property (such as, a biological property whose improvement enhances its therapeutic effect) relative to a parent peptide or peptidomimetic (i.e., the unmodified peptide). The modified peptides (i.e., the pro-drug peptides) of the present disclosure include a pro-drug portion that is cleaved in vivo, after administration, to release the parent peptide or peptidomimetic.

Without being limited to any particular theory, it is hypothesized that that the parent peptide or peptidomimetic is released from the pro-drug form via dipeptidyl peptidase-4 (DPP4), which also known as adenosine deaminase complexing protein 2 or CD26 (cluster of differentiation 26). That is, I tis believed that DDP4, which is a serine exopeptidase expressed on the surface of most cell types and that cleaves X-proline dipeptides from the N-terminus of polypeptides, cleaves the pro-drug portion in vivo to release the patent peptide or peptidomimetic. However, it is possible that other enzyme or enzymes may be involved in or facilitate, alone or in combination with DDP4, in the release of the parent peptide or peptidomimetic from the pro-drug form.

Pharmacological peptides or peptidomimetics display a number of advantageous properties that makes them excellent therapeutics, notably for autoimmune diseases. In addition to their synthesis and production that can be highly optimized, and in some cases remarkably simple in comparison to some biologics, and automatable, peptides or peptidomimetics selected as active components of pharmaceutical compositions are characterized by their stability and robustness, easy handling, the relatively low doses that have to be administrated to patients and their cost, which remains reasonable with regard to most biologics. Short peptides are not immunogenic per se, which is another considerable advantage for treating patients with chronic autoimmune diseases (Schall and Muller, 2014).

The present description provides therapeutic compositions and methods of using the same that are based on the surprising and unexpected discovery that chemically modified peptides or peptidomimetics as described herein create pro-drugs with improved biological properties that enhance the therapeutic effect of the parent peptide or peptidomimetic. In an aspect, the present disclosure provides a pro-drug peptide or a salt thereof (e.g., a pharmaceutical salt thereof) having improvement for at least one biological property relative to a parent peptide or peptidomimetic, wherein the biological property is selected from the group consisting of therapeutic index, stability, solubility, toxicity, adsorption, and pre-systemic metabolism, the pro-drug peptide comprising the following structure:

$Z_n$-pep, wherein: pep is the parent peptide or peptidomimetic; Z is a pro-drug portion, e.g., an amino acid sequence of n amino acids, wherein Z (pro-drug portion) is cleaved in vivo releasing pep; and n is an integer of 2 amino acids (e.g., 2, 3, 4, 5, 6, 7, 8, 9, or 10 or more).

The pro-drug portion (Z) can have the following structure: (Glu-Pro)$_m$ or (Lys-Pro)$_X$, wherein X is an integer ≥1 (e.g., 1, 2, 3, 4, 5, 6, 7, 8, 9, or 10 or more). For Example, Z can be Glu-Pro, Lys-Pro, Glu-Pro-Glu-Pro (SEQ ID NO: 30), Lys-Pro-Lys-Pro (SEQ ID NO: 11), Glu-Pro-Glu-Pro-Glu-Pro (SEQ ID NO: 31), and Lys-Pro-Lys-Pro-Lys-Pro (SEQ ID NO: 12). In other embodiments, the Z comprises two amino acids, and the first amino acid is functionalized with a soluble compound as described herein. In any embodiment described herein, at least the first amino acid (e.g., Lys) of the pro-drug portion (e.g., the first amino acid, the third amino acid, the fifth amino acid, the seventh amino acid, or a combination thereof, such as the first and third amino acid (e.g., first and second Lys); the first and fifth amino acid (e.g., first and third Lys); the first, third, and fifth amino acid (e.g., first, second, and third Lys; etc.) can be functionalized with a soluble compound. In particular embodiments, at least one (e.g., at least two, at least three, or at least four) Lys of Z are functionalized with a soluble compound as described herein.

The soluble compound may be aqueously soluble. For example, the pro-drug portion may be functionalized with a soluble compound comprising: 12-aminododecanoic acid (Ado), Ado-Ado-(Lys)$_m$, 8-amino-3,6-dioxaoctanoic acid (8Ado), 8Ado-8Ado-(Lys)$_m$, (Lys)$_m$ (e.g., [Lys]$_6$; SEQ ID NO: 13), or (Pro-Lys)$_m$ (e.g., [Pro-Lys]$_3$, SEQ ID NO: 29), wherein m is an integer from 0-10. In some embodiments, at least two Lys of Z (e.g., two, three, or four) are functionalized with a soluble compound, which may comprise: Ado, Ado-Ado-(Lys)$_m$, 8Ado, 8Ado-8Ado-(Lys)$_m$, (Lys)$_m$ (e.g., [Lys]$_6$; SEQ ID NO: 13), or (Pro-Lys)$_m$ (e.g., [Pro-Lys]$_3$, SEQ ID NO: 29), wherein m is an integer from 0-10 (e.g., 1, 2, 3, 4, 5, 6, 7, 8, 9, or 10).

The peptide may be amine modified at the c-terminus or the c-terminus of the peptide may be amidated.

The parent peptide or peptidomimetic can be any peptide or peptidomimetic one wishes to improve at least one biological property that enhances the therapeutic effect of the peptide or peptidomimetic. For example, the parent peptide or peptidomimetic may have an amino acid sequence that is at least 60% identical (e.g., at least 65%, 70%, 75%, 80%, 85%, 90%, 92.5%, 95%, 97.5%, 98%, 99%, or 100% identical) to glucagon. In a particular embodiments, the parent peptide or peptidomimetic has an amino acid sequence that is at least 60% identical (e.g., at least 65%, 70%, 75%, 80%, 85%, 90%, 92.5%, 95%, 97.5%, 98%, 99%, or 100% identical) to a sequence selected from the group consisting of SEQ ID NO: 1 (HSQGTFTSDYS-KYLDSRRAQDFVQWLMNT) and SEQ ID NO: 2 (HSQGTFTSDYSKYLDSRRAQDFVQWLLNT).

According to another aspect, a pharmaceutical composition is provided that comprises at least one pro-drug peptide of the present disclosure, and a pharmaceutically acceptable excipient or carrier. In certain additional aspects, the description provides therapeutic compositions comprising at least one pro-drug peptide of the present disclosure, and at least one additional bioactive agent. For example, when the parent peptide is glucagon or a peptidomimetic thereof, the additional bioactive agent can be any agent that stimulates glycogenolysis, stimulates gluconeogenesis, and/or inhibiting glycogenesis. In certain embodiments, the composition further comprises an excipient (e.g., a pharmaceutically acceptable excipient) or carrier (e.g., pharmaceutically acceptable carrier) as described herein.

According to yet another aspect, the present disclosure provides a method of treating or preventing hypoglycemia or a hypoglycemia related disorder or disease. The method comprises: administering an effective amount of the pro-drug peptide of the present disclosure or the pharmaceutical composition of the present disclosure, wherein the pro-drug peptide comprises a parent peptide or peptidomimetic that has an amino acid sequence that has at least 60% identity (e.g., at least 65%, 70%, 75%, 80%, 85%, 90%, 92.5%, 95%, 97.5%, 98%, 99%, or 100% identical) with glycogen. For example, the peptide or peptidomimetic may comprise an amino acid sequence that has at least 60% identity (e.g., at least 65%, 70%, 75%, 80%, 85%, 90%, 92.5%, 95%, 97.5%, 98%, 99%, or 100% identical) with the amino acid sequence of SEQ ID NO: 1 or SEQ ID NO: 2, and the pro-drug is effective at treating or preventing hypoglycemia or the hypoglycemia related disorder or disease.

According to a further aspect, the present disclosure provides a method of preparing a pro-drug peptide or salt thereof (e.g., a pharmaceutical salt thereof) having improved biological property or properties (e.g., at least one biological property selected from the group consisting of therapeutic index, stability, solubility, toxicity, adsorption, and pre-systemic metabolism) relative to a parent peptide or peptidomimetic. The method comprises: adding a pro-drug portion to the parent peptide or peptidomimetic (e.g., synthesizing the prodrug peptide by solid-phase synthesis or liquid-phase synthesis, wherein the pro-drug portion is located at the amino-terminus or the carboxyl-terminus of the parent peptide or peptidomimetic), wherein the pro-drug portion comprises ≥2 amino acids that are cleaved in vivo releasing the peptide or peptidomimetic.

In some embodiments, the pro-drug portion has the following structure: (Glu-Pro)$_m$ or (Lys-Pro)$_X$, wherein X is an integer ≥1 (e.g., X is 1, 2, 3, 4, 5, 6, 7, 8, 9, or 10 or more). For example, the pro-drug portion may be selected from the group consisting of EP, KP, EPEP, KPKP, EPEPEP, and KPKPKP.

In certain embodiments, at least the first Lys of the pro-drug portion is functionalized with a soluble compound or moiety. In additional embodiments, at least two Lys of the pro-drug portion are functionalized with a soluble compound or moiety. In particular embodiments, the pro-drug portion comprises two amino acids, and the first amino acid is functionalized with a soluble compound or moiety. The soluble compound or moiety may be hydrophilic or soluble in aqueous solution.

In any embodiment described herein, the first amino acid or the first Lys of the pro-drug portion may be functionalized with a soluble compound or moiety comprising: 12-aminododecanoic acid (Ado), Ado-Ado-(Lys)$_m$, 8-amino-3,6-dioxaoctanoic acid (8Ado), 8Ado-8Ado-(Lys)$_m$, (Lys)$_m$, or (Pro-Lys)$_m$. wherein m is an integer from 0-10 (e.g., 1, 2, 3, 4, 5, 6, 7, 8, 9, or 10). For example, at least two Lys of the pro-drug portion may be functionalized with a soluble compound comprising: Ado, Ado-Ado-(Lys)$_m$, 8Ado, 8Ado-8Ado-(Lys)$_m$, (Lys)$_m$, or (Pro-Lys)$_m$, wherein m is an integer from 0-10 (e.g., 1, 2, 3, 4, 5, 6, 7, 8, 9, or 10).

One skilled in the art will appreciate that the parent peptide or peptidomimetic may be any peptide or peptidomemtic that has therapeutic activity/effect. That is, the pro-drug portion (Z) of the present disclosure may be utilized on the amino-terminus or carboxyl-terminus of any peptide or peptidomimetic that is to be used therapeutically thereby improving at least one biological property of the peptide or peptidomimetic selected from the group consisting of therapeutic index, stability, solubility, toxicity, adsorption, and pre-systemic metabolism.

For example, the parent peptide or peptidomimetic may have an amino acid sequence that is at least 85% identical (e.g., about 85%, about 86%, about 87%, about 88%, about 89%, about 90%, about 91%, about 92%, about 93%, about 94%, about 95%, about 96%, about 97%, about 98%, about 99%, or about 100%) to a sequence selected from the group consisting of SEQ ID NO: 1 (HSQGTFTSDYSKYLDSRRAQDFVQWLMNT) and SEQ ID NO: 2 (HSQGTFTSDYSKYLDSRRAQDFVQWLLNT).

The method may further comprise amidating the c-terminus of the peptide or modifying the c-terminus of the protein with an amine.

In any of the aspects or embodiments described herein, the peptide(s) provided by the present disclosure can be present in a form of a salt known to a person skilled in the art, such as, e.g., sodium salts, ammonium salts, calcium salts, magnesium salts, potassium salts, acetate salts, carbonate salts, citrate salts, chloride salts, sulphate salts, amino chlorhydate salts, borhydrate salts, benzensulphonate salts, phosphate salts, dihydrogenophosphate salts, succinate salts, citrate salts, tartrate salts, lactate salts, mandelate salts, methane sulfonate salts (mesylate) or p-toluene sulfonate salts (tosylate). This list is provided by way of example and is not meant to be limiting on the present invention. For example, the skilled person can easily determine, according to his knowledge, the appropriate salt.

Chemical synthesis may be performed by any method one skilled in the art would appreciate is effective at synthesizing the pro-drug peptides described herein. For example, the pro-drug peptide may be polymerized by adding the required amino acids or molecules. A method is disclosed in the example section.

Pharmaceutical Compositions

In another aspect the present description provides compositions comprising an effective amount of one or more of the peptides as described herein, and an excipient or carrier. Thus, in additional embodiments, the description also provides pharmaceutical compositions comprising at least one pro-drug peptide as described herein, or a combination product as described above, further including a pharmaceutically acceptable carrier.

The pro-drug peptides (also referred to herein as "active compounds") as described herein can be incorporated into pharmaceutical compositions suitable for administration. Such compositions typically comprise peptide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds (e.g., additional bioactive agent) can also be incorporated into the compositions.

The description provides methods for preparing pharmaceutical compositions. Such methods comprise formulating a pharmaceutically acceptable carrier with at least one pro-drug peptide as described herein. Such compositions can further include additional active agents as described above. Thus, the invention further includes methods for preparing a pharmaceutical composition by formulating a pharmaceutically acceptable carrier with at least one pro-drug peptide (e.g., 1, 2, 3, 4, or 5) as described herein, and one or more additional active compounds (e.g., 1, 2, 3, 4, or 5).

A pharmaceutical composition of the invention is formulated to be compatible with its intended route of administration. Examples of routes of administration include parenteral, e.g., intravenous, intradermal, subcutaneous, oral, nasal (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol; antioxidants such as ascorbic acid or sodium bisulfate; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, chlorobutanol, phenol, ascorbic acid, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a pro-drug peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In certain embodiments of the methods provided herein, the method includes the step of administering a dosage from about 100 ng to about 5 mg of a therapeutic or pharmaceutical composition as described herein. In certain embodiments, e.g., in human, the pharmaceutical composition as described herein may contain mannitol as carrier, and the composition is administered from 10 µg to 500 µg, preferably 200 µg, in a single administration.

In certain additional aspects, the dosage regimen can be reproduced from 1 to 3 times/week, every week to every four week for as long as needed with therapeutic windows and thus for several years. In a preferred embodiment, the dosage regimen is once every 4 weeks of treatment but can be repeated twice a year for several years. An example of administration is: one injection of 200 µg of peptide, every 4 weeks, for 12 weeks (i.e. 3 injections separated from each other by 4 weeks). The treatment can be prolonged by administration every 6 months.

Preferred pharmaceutically acceptable carriers can comprise, for example, xanthan gum, locust bean gum, galactose, other saccharides, oligosaccharides and/or polysaccharides, starch, starch fragments, dextrins, British gum and mixtures thereof. Advantageously, the pharmaceutically acceptable carrier is of natural origin. The pharmaceutically acceptable carrier can be, or can further comprise, an inert saccharide diluent selected from a monosaccharide or disaccharide. Advantageous saccharide is mannitol.

Advantageously, the invention relates to a pharmaceutical composition as defined above, which is in the form of a liposome, or nano particles, or in the form of a solution. An advantageous solution is a solution comprising from 1 to 15%, in particular about 10% of mannitol. The solution should be iso-osmolar.

The invention also relates to a drug comprising a combination product as defined above, for a simultaneous, separate or sequential use.

Therapeutic Methods

In an additional aspect, the present description provides methods for treating, preventing, and/or ameliorating the symptoms of hypoglycemia or a hypoglycemia-related disease or disorder. The method comprising administering an effective amount of the pro-drug peptides of the present disclosure or the pharmaceutical or therapeutic composition of the present disclosure to a subject in need thereof, wherein the composition is effective for treating, preventing and/or ameliorating at least one symptom of hypoglycemia or a hypoglycemia-related disease or disorder. In certain embodiments, the disease or disorder is insulin-induced hypoglycemia.

The description also provides a pro-drug peptide comprising a peptide or peptidomimetic as described herein and a prodrug portion as described herein for its use as drug, in particular for the treatment of hypoglycemia or a hypoglycemia-related disease or disorder.

One skilled in the art will appreciate that there are numerous ways in which to prepare the pro-drug peptide or peptidomimetic of the present disclosure. For example, one could utilize standard Fmoc/Boc protected solid phase peptide synthesis. As such, when the amine on the side chain of a lysine is functionalize, one can either switch the Fmoc/Boc protecting groups of the amines of the N-terminal lysine if it is the last amino acid, or if using an Alloc lysine, if this lysine is not the last one and a Boc on the N-terminal of the last amino acid. The Alloc at the end of the sequence would then be removed with Pd(o) and the amine functionalized.

EXAMPLES

Example 1

General Procedure for Peptide Synthesis.

The synthesis of peptides 1-9, which respectively correspond to SEQ ID NOs: 2-5, 8-10, 6 and 7, was conducted on automated peptide synthesizer LibertyBlue from CEM Company using Fmoc solid phase strategy with PyBop and DIEA as coupling reagents according to previously reported procedures. Merrifield, R. B. *J. Am. Chem. Soc.* 1963, 85, 2149-2154; Palasek S. A., Cox Z. J., Collins J. M. *J. Pept. Sci.* 2007; 13, 143-148; Douat-Casassus C, Pulka K, Claudon P, Guichard G, *Org. Lett.* 2012, 14, 3130-3133.

Solubility Analysis of Exemplary Peptides.

A solution of 3 mg/mL of peptide or peptidomimetic (glucagon or analog thereof) was prepared in a 0.01M HCl solution. Then 0.1 mL of the stock solution was diluted to 1 mL with HCl (0.01M) and the UV absorbance was measured (to 280 nm) with nanodrop UV spectrometer (NanoDrop 1000 from Thermo Fischer Company). The pH of the remaining stock solution was adjusted to pH 7 using $Na_2HPO_4$ (0.1M) and the solution was allowed to stand overnight at 4° C. Then the solution was centrifuged three times (5 min, 4000 $min^{-1}$), 0.1 mL of the supernatant was removed and diluted to 1 mL with HCl solution (0.01M). The final UV absorbance was measured.

The solubility was assessed by the following calculation:

(Final Absorbance/Initial Absorbance)×3 mg/mL=Solubility (mg/mL).

TABLE 1 solubility and stabilities of peptides 1 to 7

| Compound | Solubility in Water (mg/ml) |
|---|---|
| 1 | 0.24 |
| 2 | 0.35 |
| 3 | 1.2 |
| 4 | 1.74 |
| 5 | 1.78 |
| 6 | 0.53 |
| 7 | 1.06 |

Stability Analysis of Exemplary Peptides.

A solution of 1 mg/mL of peptide or peptidomimetic (glucagon or analog thereof) was prepared in water or physiological serum and stored at room temperature or at 4° C. The samples were analyzed by high-performance liquid chromatography (HPLC) with 10 to 100% $CH_3CN$ (+0.1% trifluoroacetic acid (TFA) v/v) in water (+0.1% TFA v/v) in 10 minutes as gradient. The HPLC column (EC 100/4 NUCLEODUR 100-3 C18ec) was purchased to Macherey-Nagel Company.

Peptides 3, 4, and 5 demonstrated good stability at room temperature for extended periods of time. See FIGS. 5-7, and 9 in water, PBS, and physiological serum.

In Vivo Analysis of Exemplary Glucagon-Based Peptides.

The 18 animals (rats, males, 8-week old) were housed in ventilated and enriched housing cages (310×125×127 $mm^3$) throughout the experimental phase. They were housed in groups of 3 animals during the study, on a normal 12 hours light cycle (at 08:00 pm lights off), 22±2° C. and 50±10% relative humidity. They were acclimated for 5 days with standard diet and tap water. Then, after 3 hours fasting, the animals were treated with glucagon or analogs 3, 4 and 5 (10 nM/kg) via i.v. administration. Blood glucose was measured before dosing and at 10 minutes, 20 minutes, 30 minutes, 45 minutes, 60 minutes, and 120 minutes.

The Exemplary peptides demonstrated better ability to raise blood glucose over the course of treatment, relative to the glucagon control, as well as the inactive peptide and vehicle control.

Example 2

Detailed Procedures for Peptide Synthesis.

A1: Rink amide (≈200 mg, loading 0.5 mmol/g) or Sieber resin (≈160 mg, loading 0.62 mmol/g) was swelled in dimethyl formaldehyde (DMF; 3 mL) for 30 minutes. Peptide synthesis was then conducted with an automated peptide synthesizer (LibertyBlue from CEM Company) using Fmoc solid phase strategy with PyBop (5 eq. relative to the resin loading) and N, N-diisopropylethylamine (DIEA; 10 eq. relative to the resin loading) as coupling reagents according to previously reported procedures (Merrifield, R. B. *J. Am. Chem. Soc.* 1963, 85, 2149-2154; Palasek S. A., Cox Z. J., Collins J. M. *J. Pept. Sci.* 2007; 13, 143-148).

A2: Wang resin (≈220 mg, loading 0.4 mmol/g) was swelled in DMF (3 mL) for 30 minutes. First amino-acid (5 eq.) was dissolved in dry dichloromethane (DCM; 3 mL) under inert atmosphere. N, N'-dicyclohexylcarbodiimide (DCC; 2.5 eq.) was added and the mixture was stirred 20 minutes at 0° C. before DCM concentration and DMF addition. The mixture was loaded on the swollen Wang resin with a small amount of 4-dimethylaminopyridine (DMAP). The resin was shacked for 2 hours at room temperature then filtrated and washed three times with DMF, DCM and MeOH. Then the peptide was synthesized according to procedure A1 or A2.

B: Alloc deprotection: resin was swollen in DCM for 30 minutes then $Pd(Ph_3)_4$ (0.25 eq.) and phenylsilane (10 eq.) were added. The mixture was stirred at room temperature for 45 minutes then the resin is filtrated and wash 3 times with DCM.

Cleavage Procedures:

C1: After completion of the synthesis, the resin was transferred into a syringe with a frit, and washed three times with DMF, three times with $CH_2Cl_2$ and three times with $Et_2O$. Cleavage from the resin was performed using 88% TFA with 2% triisopropylsilane 5% phenol and 5% water (3 mL). After 2 hours the resin was filtered and discarded. Diethyl ether was added to precipitate the oligomer and the solid was triturated and filtrated.

C2: After completion of the synthesis, the resin was transferred into a syringe with a frit, and washed three times with DMF, three times with $CH_2Cl_2$ and three times with $Et_2O$. Cleavage from the resin was performed using 88% TFA with 2.5% triisopropylsilane and 2.5% water (3 mL). After 2 hours the resin was filtered and discarded. Diethyl ether was added to precipitate the oligomer and the solid was triturated and filtrated.

General Procedure for Purification.

All the peptides were purified by semi preparative HPLC on a Dionex U3000SD using a Macherey-Nagel Nucleodur C18ec column (10×250 mm, 5 μm) at a flow rate of 4 mL/min with UV detection at 200 nm. The mobile phase was composed of 0.1% (v/v) TFA-H$_2$O (Solvent A) and 0.1% (v/v) TFA-CH$_3$CN (solvent B).

General Procedure for Analysis.

Peptides 10-25, which respectfully correspond to SEQ ID NOs:1 and 14-28, were analyzed by analytical RP-HPLC on a Dionex U3000SD using a Macherey-Nagel Nucleodur C18ec column (4×100 mm, 3 μm) at a flow rate of 1 mL/min with UV detection at 200 nm. The mobile phase was composed of 0.1% (v/v) TFA-H$_2$O (Solvent A) and 0.1% (v/v) TFA-CH$_3$CN (solvent B). Liquid chromatography-mass spectrometry (LC-MS) analyses were carried out on a ultra-high performance liquid chromatography (UHPLC; Agilent 1290 Infinity) coupled to an electrospray ionization time-of-flight (ESI-TOF) mass spectrometer (Agilent 6230 ESI).

Solubility Assay.

A solution of the compound (e.g., glucagon or analogues thereof) was prepared in a 0.01M HCl solution. Then 0.1 mL of the stock solution was diluted to 1 mL with HCl (0.01M) and the UV absorbance was measured (to 280 nm) with NanoDrop UV spectrometer (NanoDrop 1000 from Thermo Fischer Company). The pH of the remaining stock solution was adjusted to pH 7 using Na$_2$HPO$_4$ (0.1M) and the solution was allowed to stand overnight at 4° C. Then the solution was centrifuged three times (5 min, 4000 min$^{-1}$), 0.1 mL of the supernatant was removed and diluted to 1 mL with HCl solution (0.01M). The final UV absorbance was measured. The solubility was accessible by the following formula:

(Final Absorbance/Initial Absorbance)×100=Percent Soluble

The percent solubility of glucagon and exemplary peptides is shown in Table 2. As can be seen by the data of Table 2, the exemplary glucagon analogues have greater solubility as compared to glucagon.

TABLE 2

Solubility of Glucagon and analogues thereof in PBS buffer (0.1M) at pH 7.4

| Compound | Solubility at 1 mg/mL (%) | Solubility at 25 mg/mL (%) |
|---|---|---|
| 10 | 15 | |
| 11 | 17 | |
| 12 | 20 | |
| 13 | 56 | |
| 14 | 77 | |
| 16 | 80 | |
| 17 | 82 | |
| 18 | 18 | |
| 19 | 92 | 88 |
| 21 | | 92 |
| 22 | 34 | |
| 23 | 79 | |
| 25 | 75 | 92 |

Stability Assay.

A solution of 1 mg/mL of peptide or peptidomimetic (glucagon or analog thereof) was prepared in a NaCl 0.9% aqueous solution and stored at room temperature, or 4° C., or 37° C. and or 50° C. The samples were analyzed by RP-HPLC on a Dionex U3000SD using a Macherey-Nagel Nucleodur C18ec column (4×100 mm, 3 μm) at a flow rate of 1 mL/min with UV detection at 200 nm. The mobile phase was composed of 0.1% (v/v) TFA-H$_2$O (Solvent A) and 0.1% (v/v) TFA-CH$_3$CN (Solvent B). The percent of exemplary peptide or glucagon remaining after incubation at varying temperatures and times is shown in Table 3.

TABLE 3

Percentage of peptide remaining in an aqueous solution of NaCl 0.9% at different temperatures after different times (T0 = 100%)

| Compound | T° C. | 1 week | 1 month | 5 months |
|---|---|---|---|---|
| 10 | RT | 95 | 85 | 0 |
| 10 | 4° C. | 91 | 86 | 0 |
| 13 | RT | 97 | 95 | 84 |
| 13 | 4° C. | 98 | 98 | 93 |
| 14 | RT | 99 | 97 | 87 |
| 14 | 4° C. | 99 | 99 | 97 |
| 16 | RT | 95 | 94 | 80 |
| 16 | 4° C. | 97 | 95 | 90 |
| 17 | RT | 97 | 95 | 86 |
| 17 | 4° C. | 96 | 96 | 91 |
| 19 | RT | 100 | 97 | 89 |
| 19 | 4° C. | 100 | 100 | 95 |
| 19 | 37° C. | 95 | 86 | — |
| 19 | 50° C. | 79 | 65 | — |
| 19 | 70° C. | 16 | 0 | — |
| 21 | RT | 94 | — | — |
| 21 | 37° C. | 88 | 69 | — |
| 21 | 50° C. | 81 | 58 | — |
| 21 | 70° C. | 24 | — | — |
| 24 | RT | 97 | 94 | 81 |
| 24 | 4° C. | 97 | 97 | 92 |
| 24 | 37° C. | 89 | 78 | — |
| 24 | 50° C. | 84 | 67 | — |
| 25 | RT | 98 | 98 | 86 |
| 25 | 4° C. | 100 | 100 | 93 |
| 25 | 37° C. | 86 | 71 | — |
| 25 | 50° C. | 77 | 53 | — |

Rat Studies.

Figure 12:
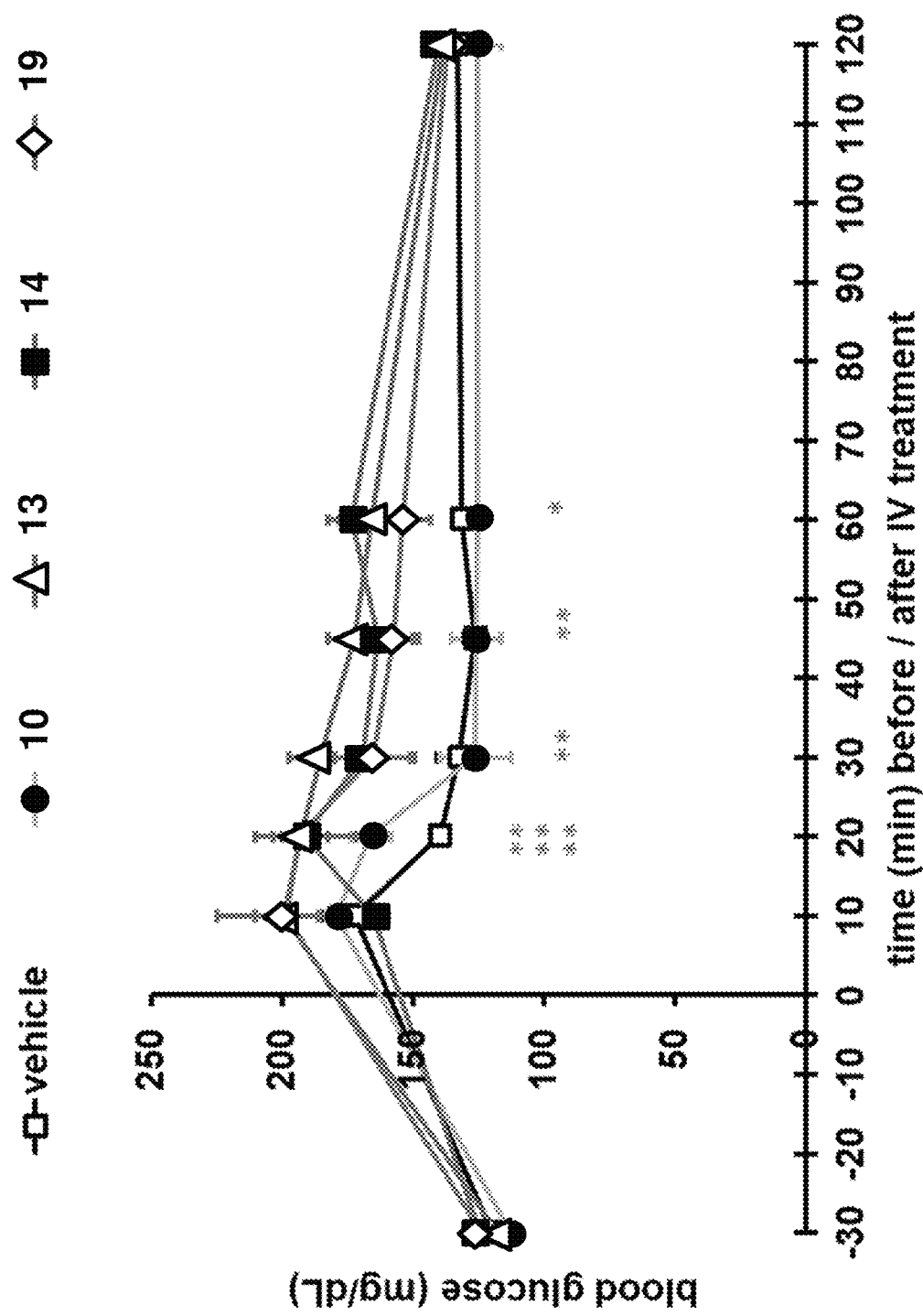
FIG. 12. Blood glucose measurement (mg/dl) 30 minutes before dosing Wistar rats with vehicle and compound 10, 13, 14 and 19 at t=10, 20, 30, 45, 60 and 120 minutes after injection (n=6), * $p<0.05$; ** $p<0.01$: two way anova with Bonferroni post tests.
Figure 13:
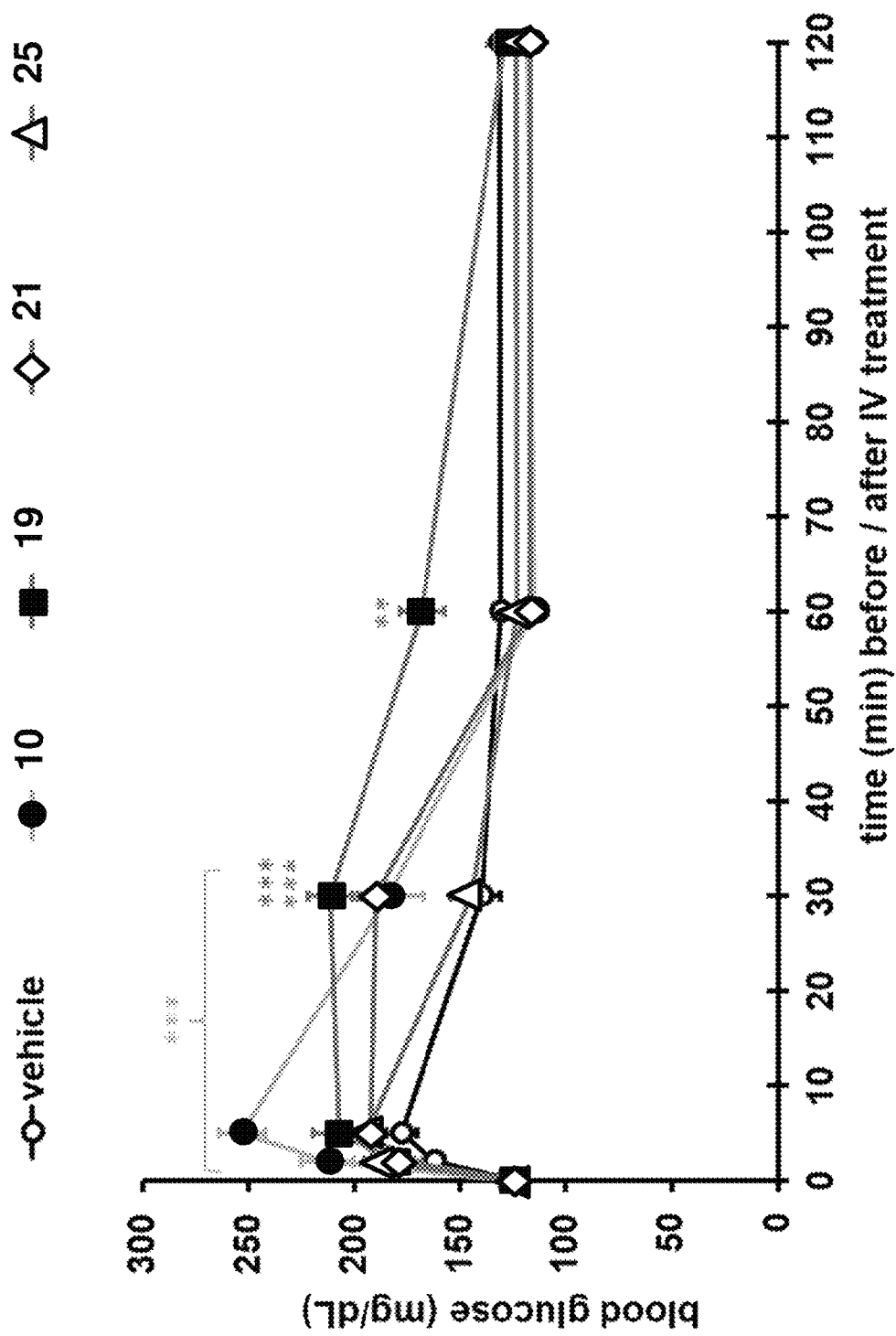
FIG. 13. Blood glucose measurement (mg/dl) before and after dosing Wistar rats with vehicle and compound 10, 19, 21, and 25 at t=2, 5, 30, 60 and 120 minutes after injection (n=3), * $p<0.05$;  $p<0.01$; * $p<0.001$: two way anova with Bonferroni post tests.
Figure 14A:
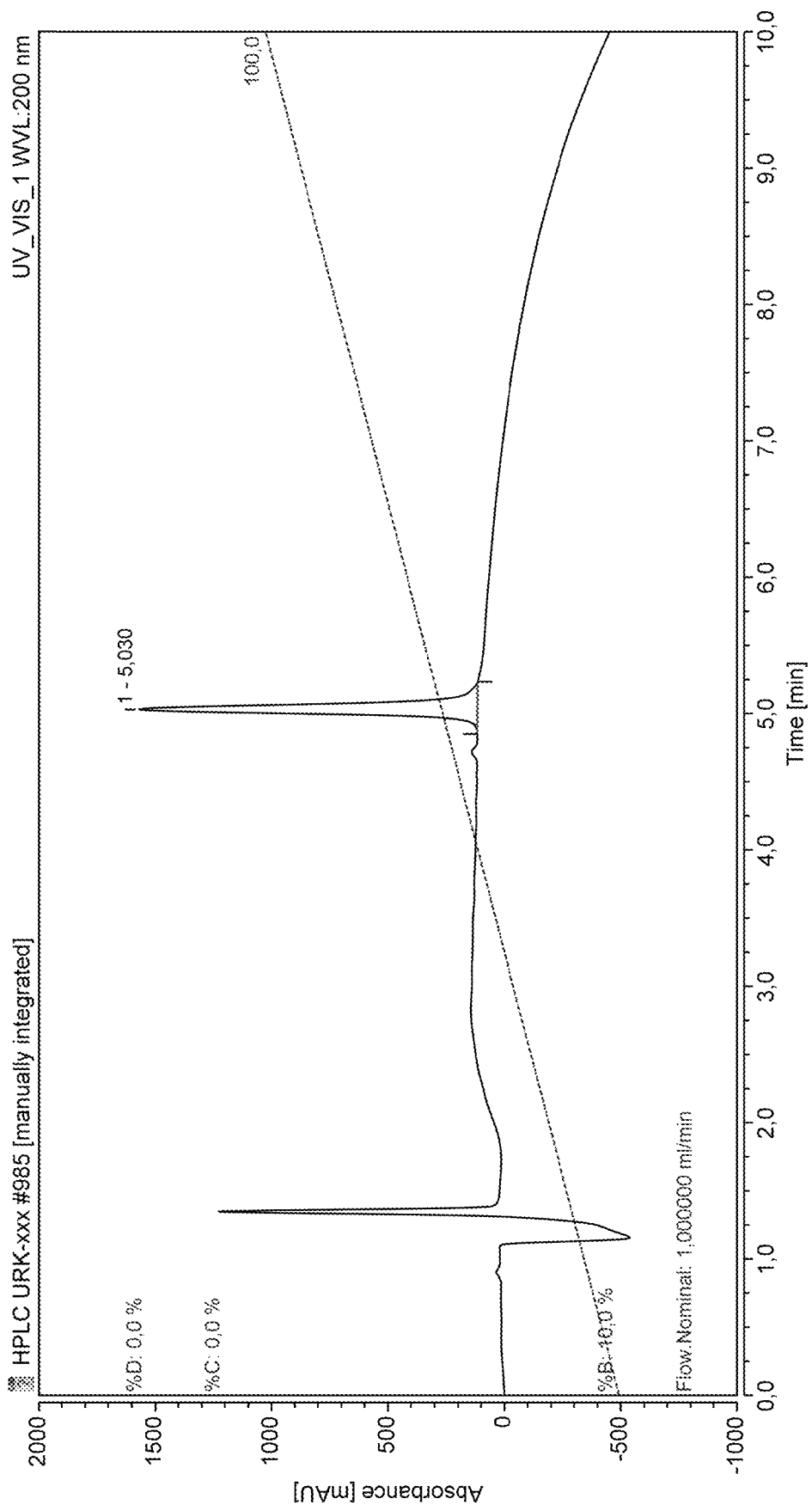
FIG. 14A and FIG. 14B. (A) High-performance liquid chromatography (HPLC) profile of peptide 10 (10-100%; $CH_3CN$ 0.1% trifluoroacetic acid (TFA) in $H_2O$ 0.1% TFA, 10 min, C18). (B) liquid chromatography-mass spectrometry (LC-MS) spectrum of peptide 10.
Figure 14B:
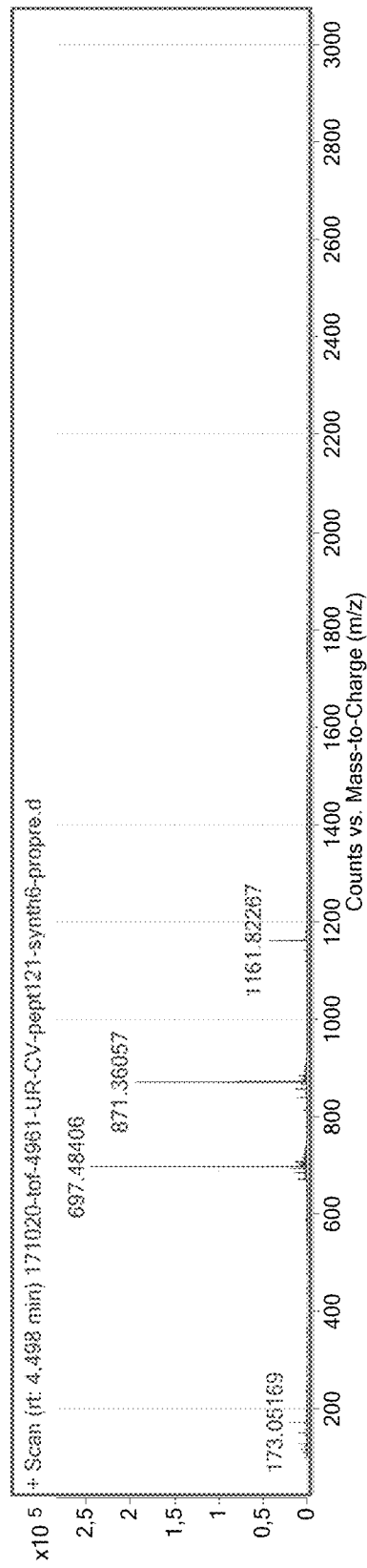
Figure 15A:
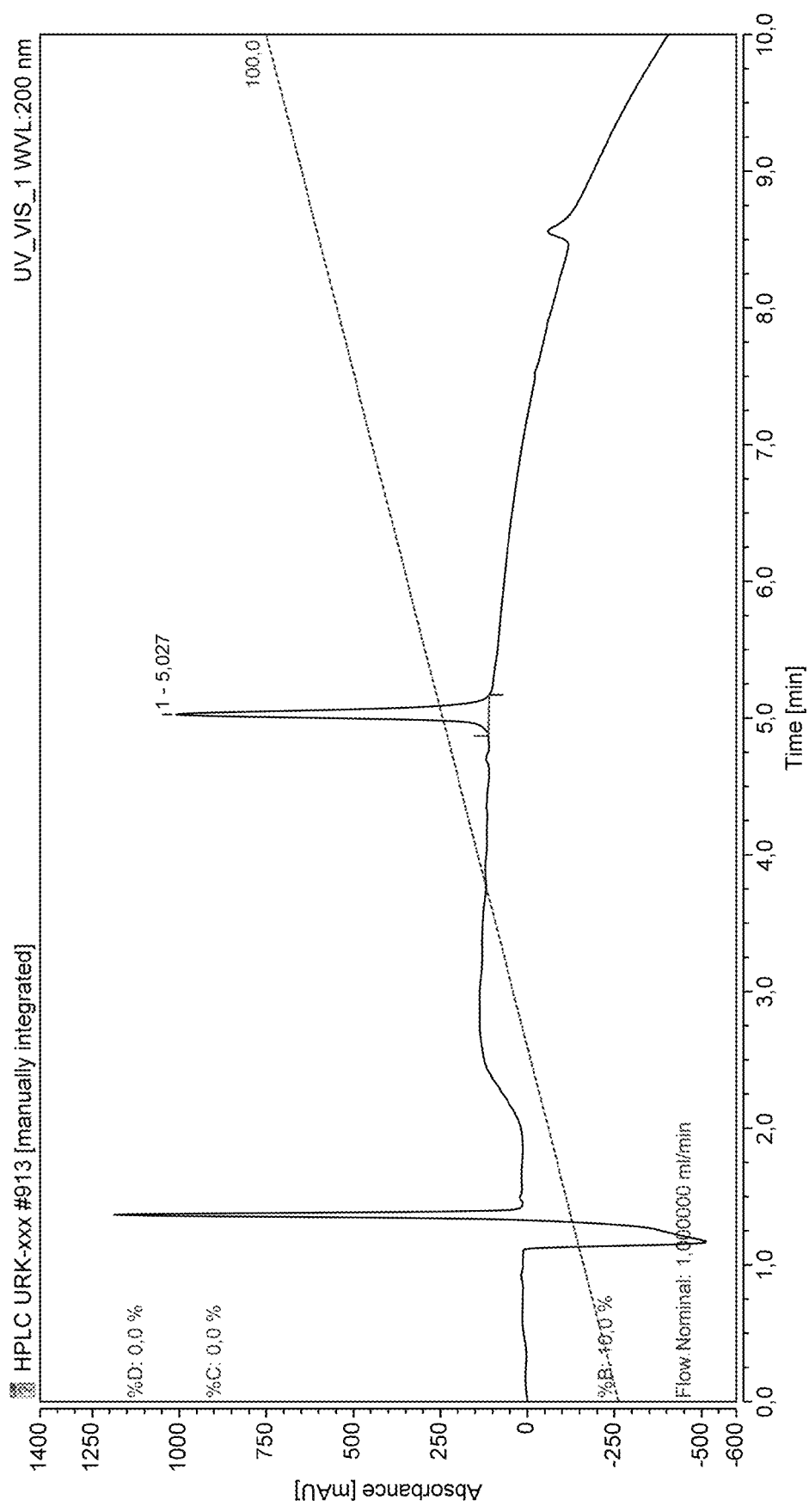
FIG. 15A and FIG. 15B. (A) HPLC profile of peptide 11 (10-100%; $CH_3CN$ 0.1% TFA in $H_2O$ 0.1% TFA, 10 min, C18). (B) LC-MS spectrum of peptide 11.
Figure 15B:
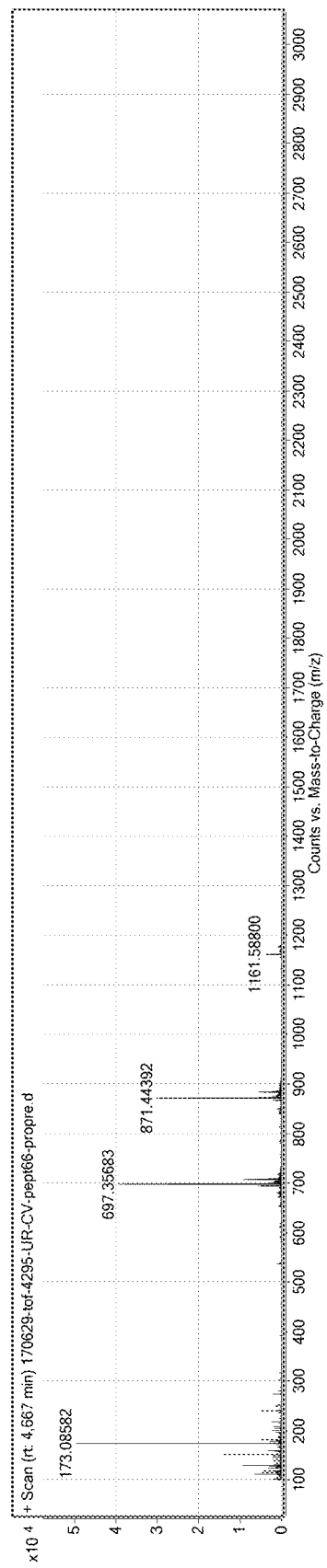
Figure 16A:
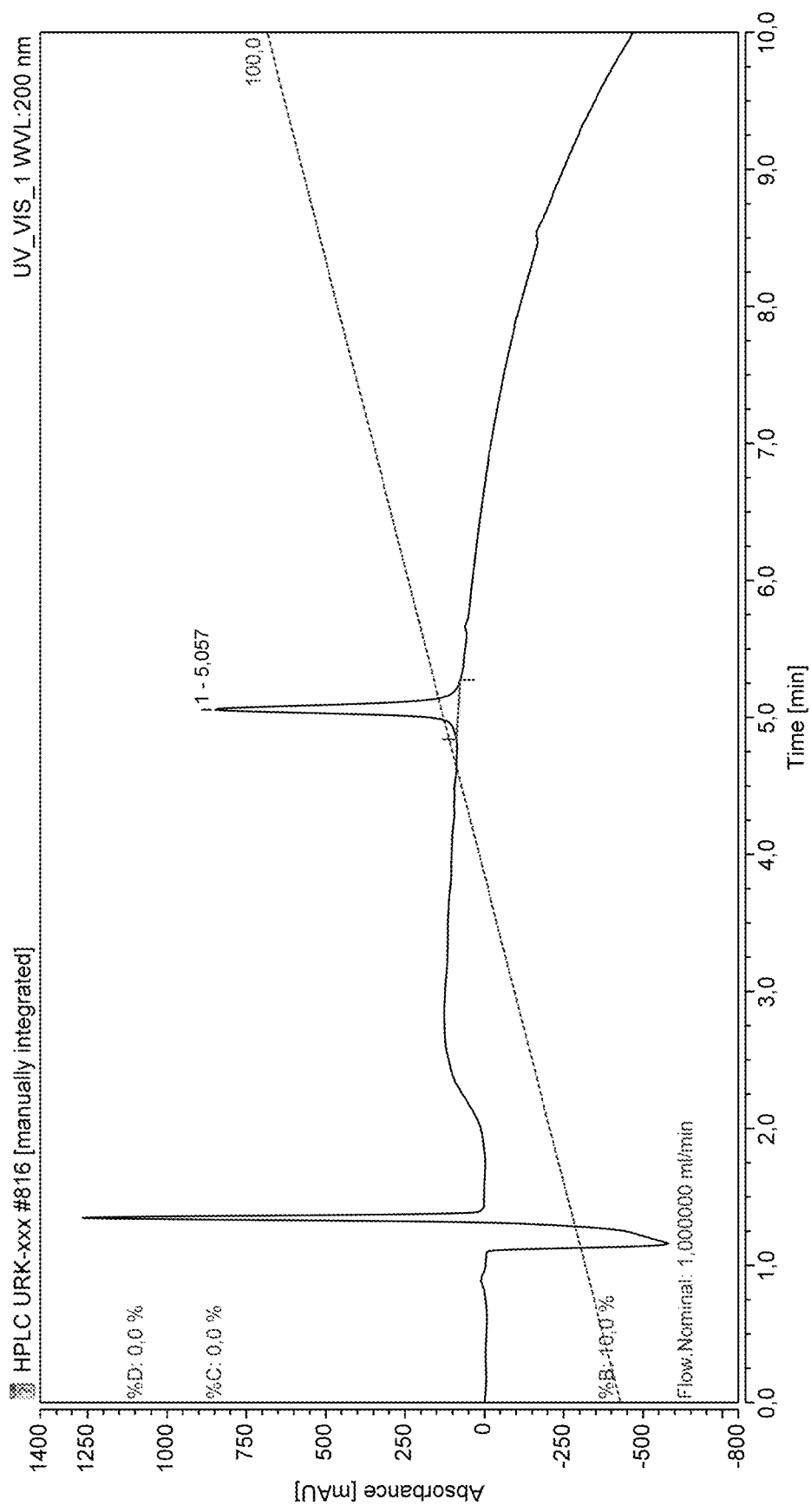
FIG. 16A and FIG. 16B. (A) HPLC profile of peptide 12 (10-100%; $CH_3CN$ 0.1% TFA in $H_2O$ 0.1% TFA, 10 min, C18). (B) LC-MS spectrum of peptide 12.
Figure 16B:
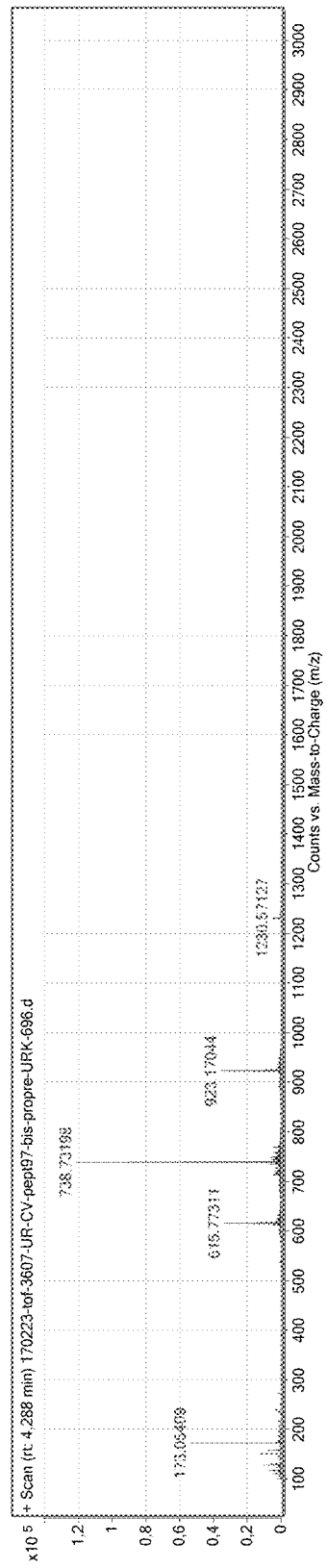
Figure 17A:
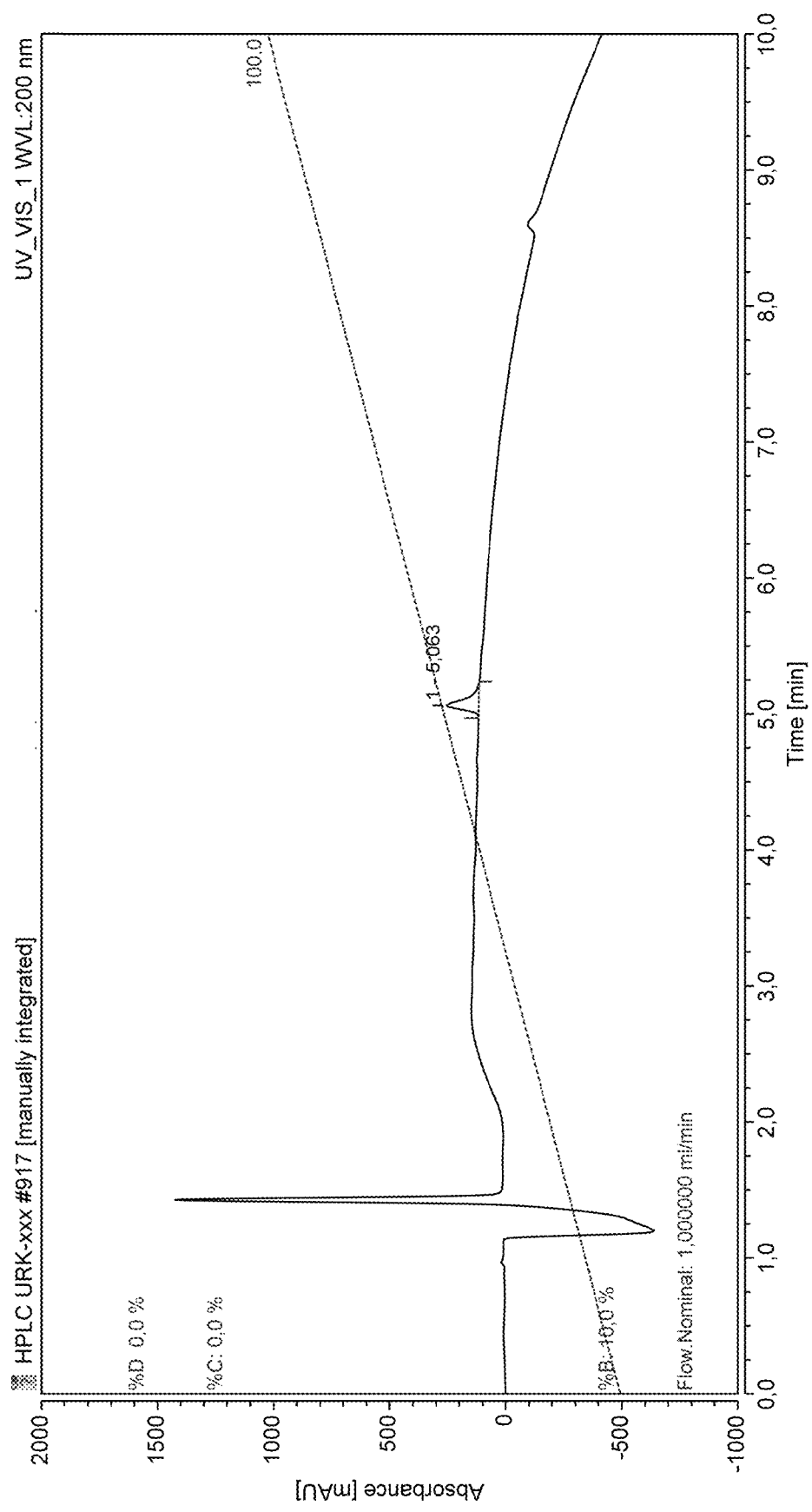
FIG. 17A and FIG. 17B. (A) HPLC profile of peptide 13 (10-100%; $CH_3CN$ 0.1% TFA in $H_2O$ 0.1% TFA, 10 min, C18). (B) LC-MS spectrum of peptide 13.
Figure 17B:
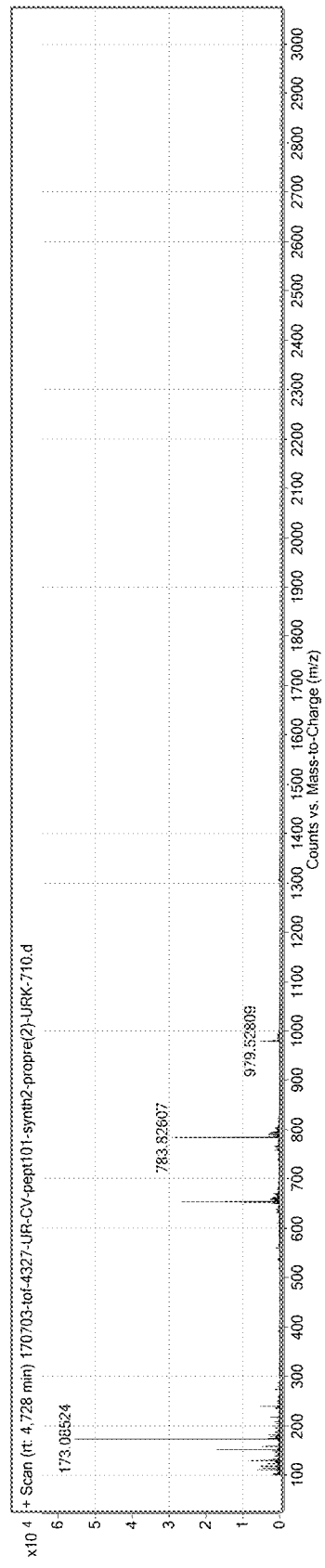
Figure 18A:
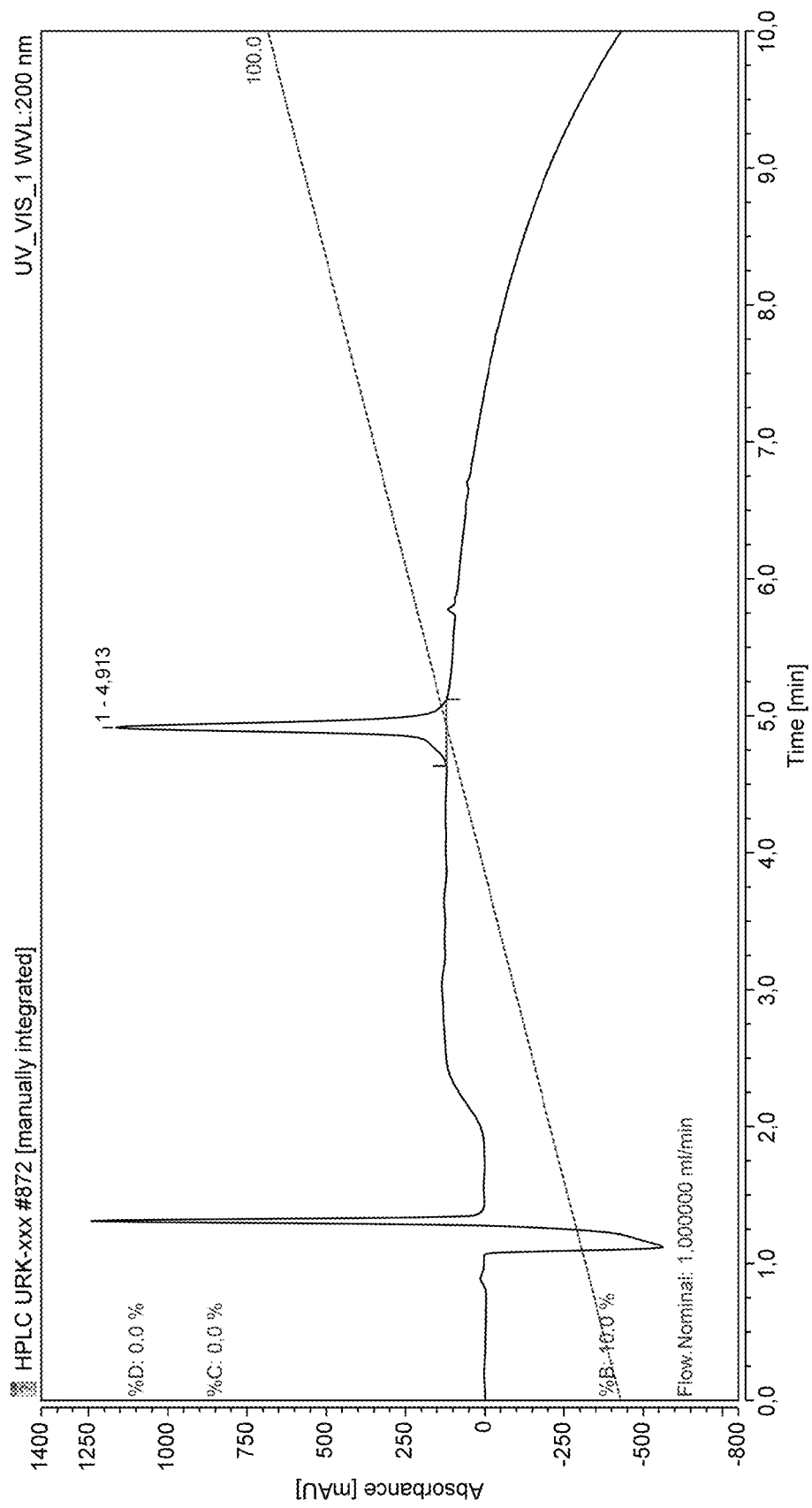
FIG. 18A and FIG. 18B. (A) HPLC profile of peptide 14 (10-100%; $CH_3CN$ 0.1% TFA in $H_2O$ 0.1% TFA, 10 min, C18). (B) LC-MS spectrum of peptide 14.
Figure 18B:
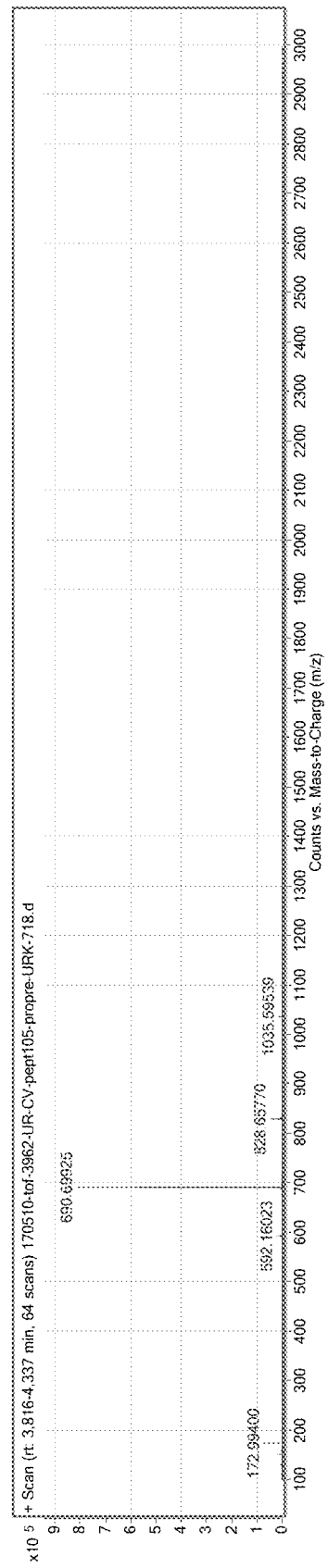
Figure 19A:
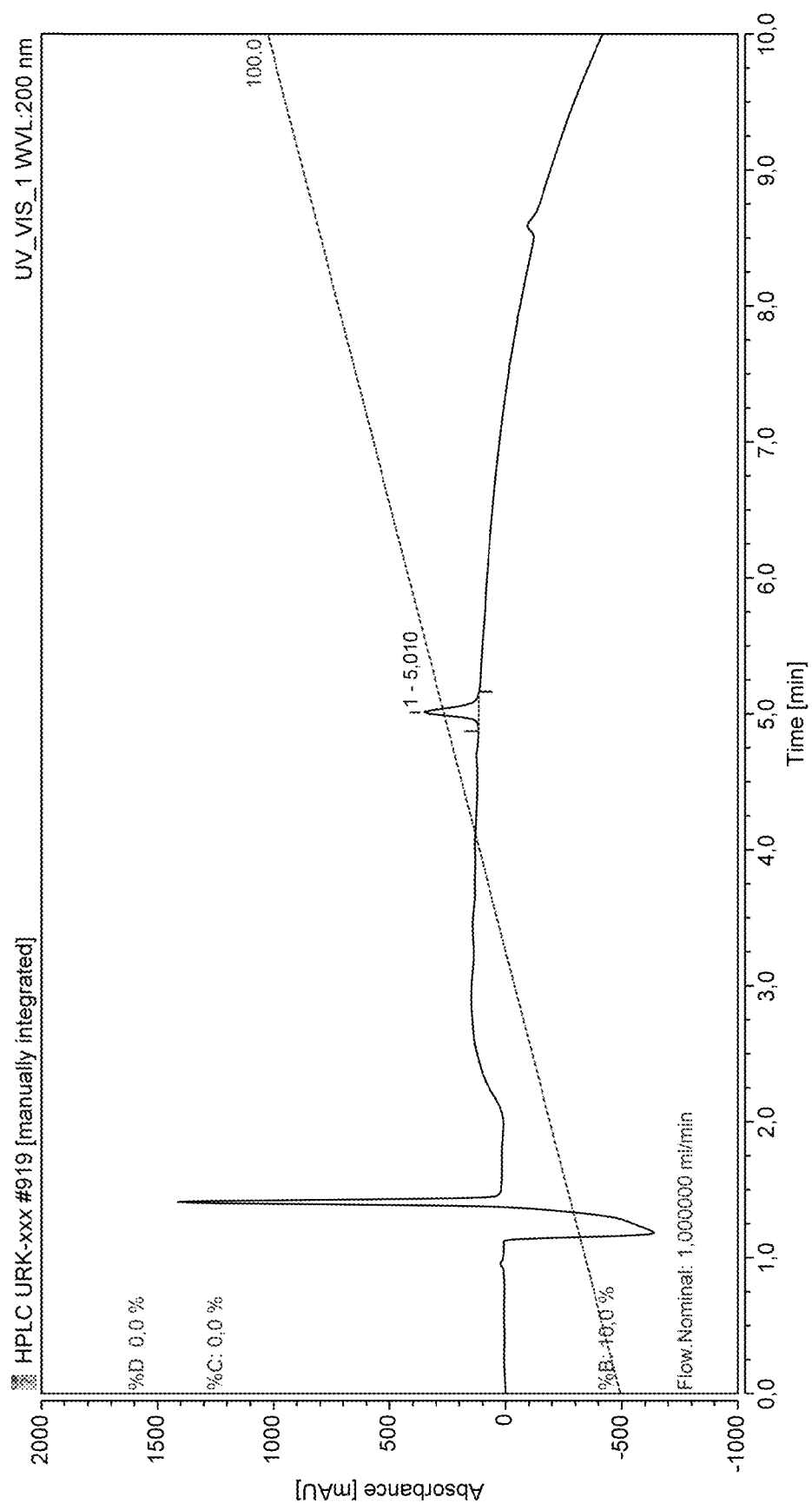
FIG. 19A and FIG. 19B. (A) HPLC profile of peptide 15 (10-100%; $CH_3CN$ 0.1% TFA in $H_2O$ 0.1% TFA, 10 min, C18). (B) LC-MS spectrum of peptide 15.
Figure 19B:
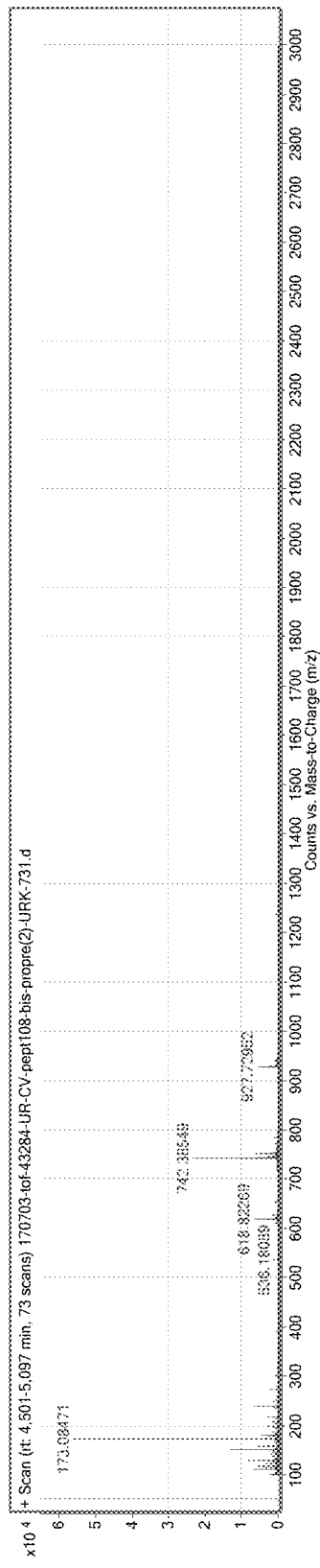
Figure 20A:
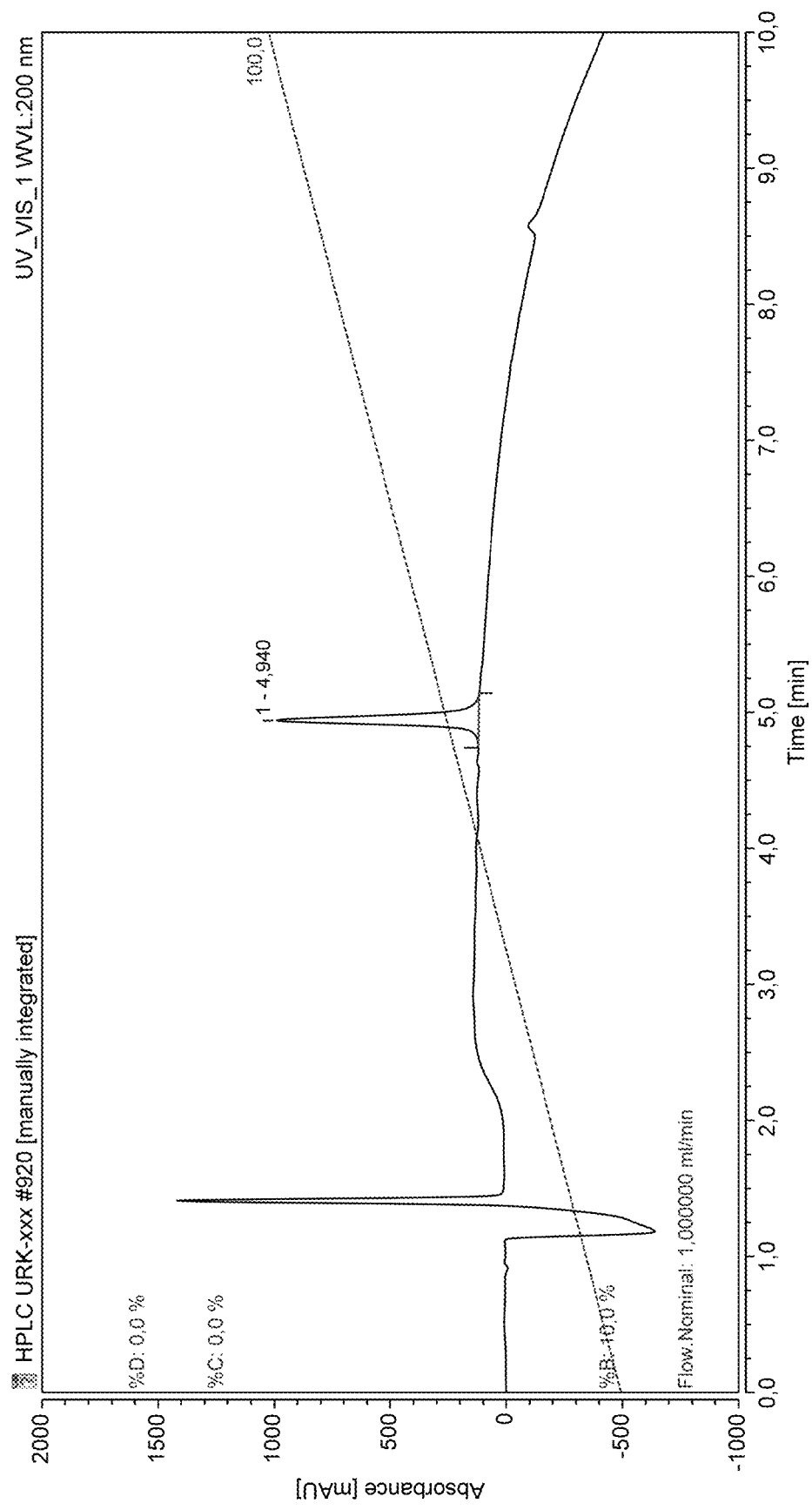
FIG. 20A and FIG. 20B. (A) HPLC profile of peptide 16 (10-100%; $CH_3CN$ 0.1% TFA in $H_2O$ 0.1% TFA, 10 min, C18). (B) LC-MS spectrum of peptide 16.
Figure 20B:
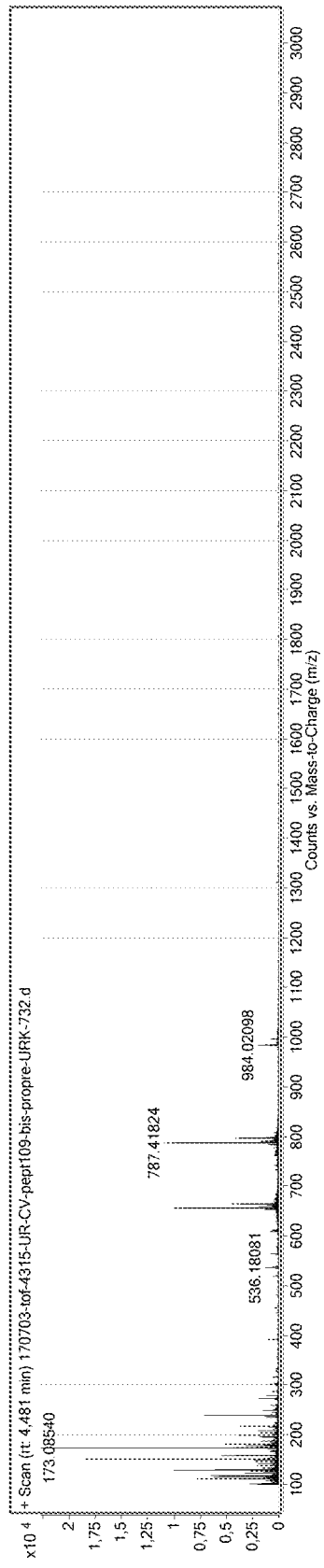
Figure 21A:
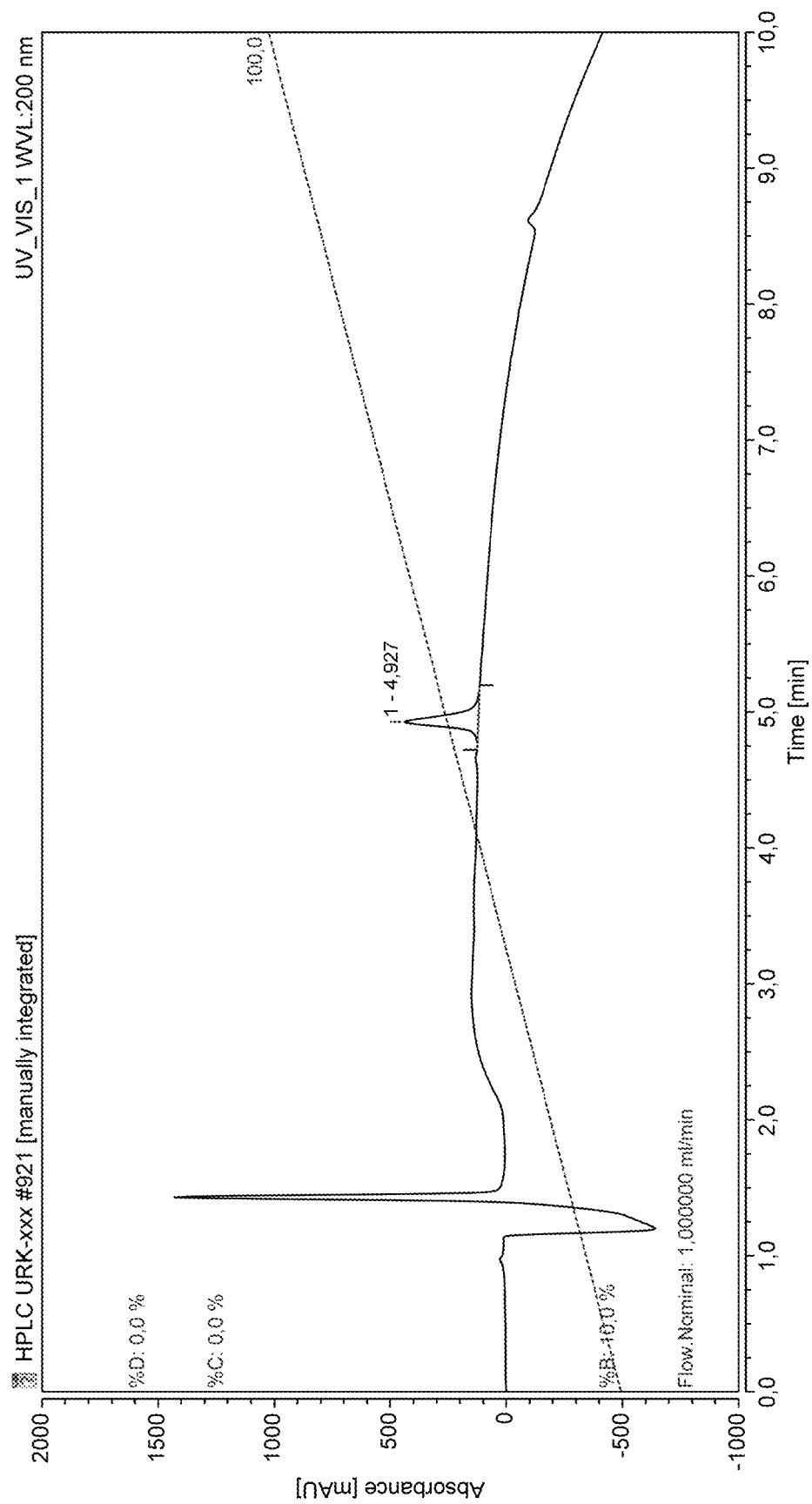
FIG. 21A and FIG. 21B. (A) HPLC profile of peptide 17 (10-100%; $CH_3CN$ 0.1% TFA in $H_2O$ 0.1% TFA, 10 min, C18). (B) LC-MS spectrum of peptide 17.
Figure 21B:
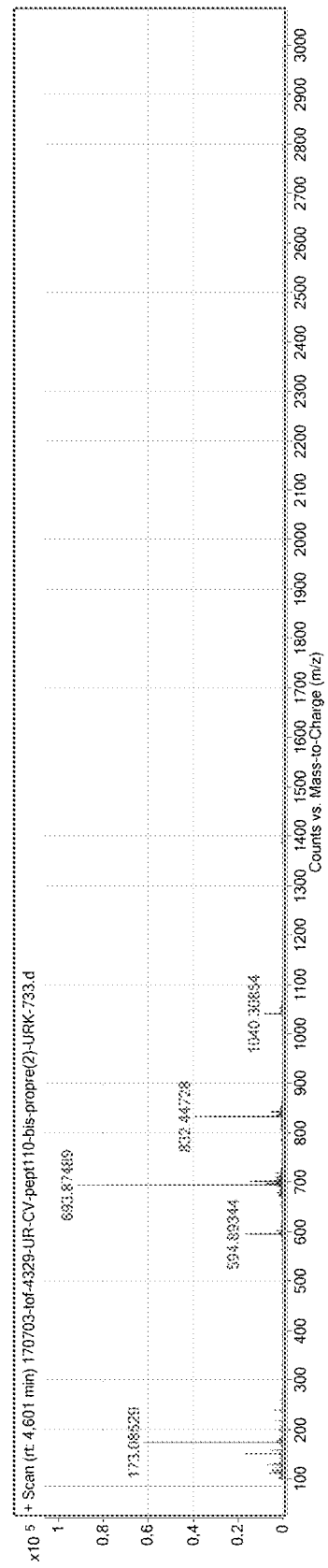
Figure 22A:
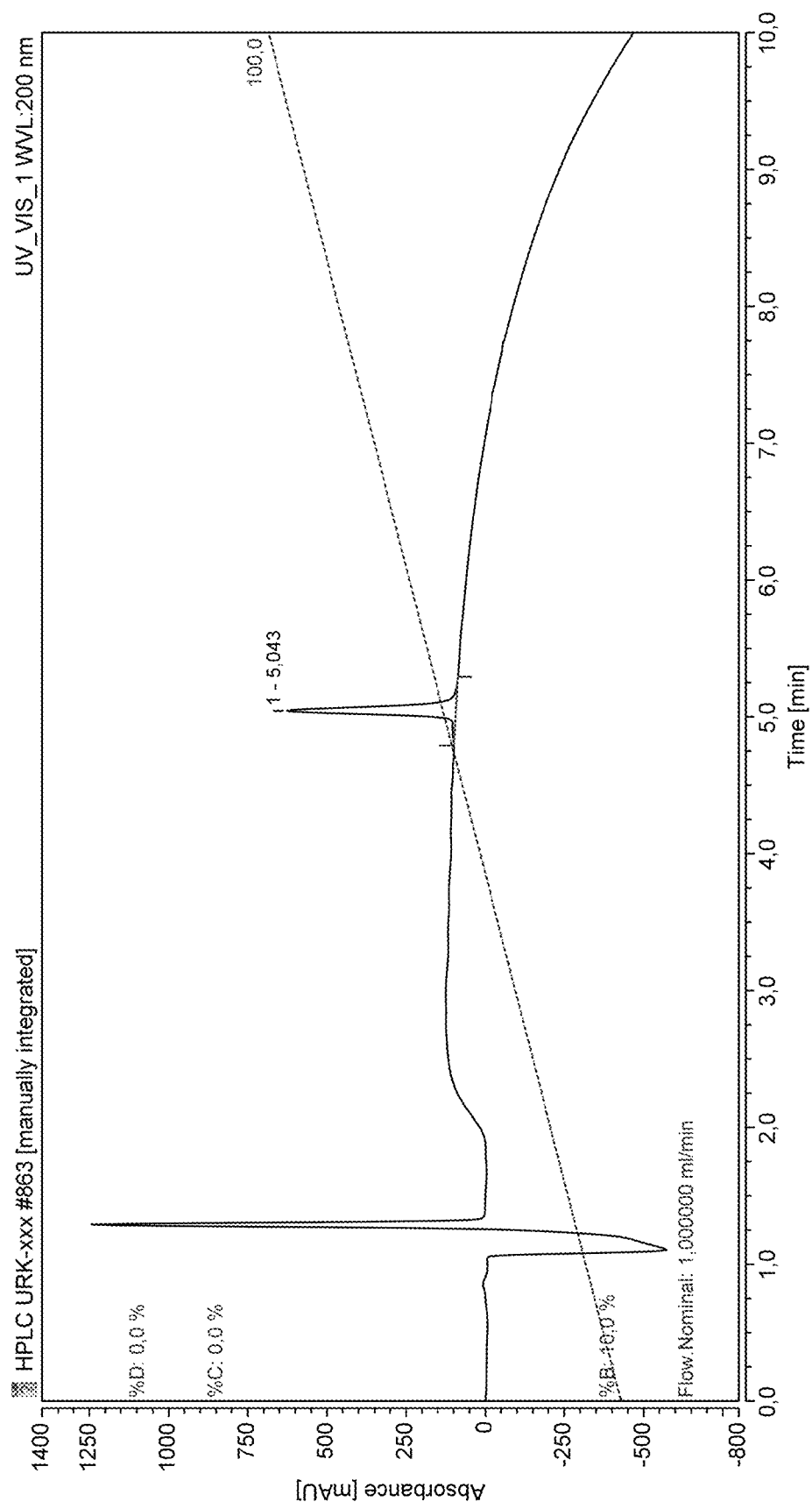
FIG. 22A and FIG. 22B. (A) HPLC profile of peptide 18 (10-100%; $CH_3CN$ 0.1% TFA in $H_2O$ 0.1% TFA, 10 min, C18). (B) LC-MS spectrum of peptide 18.
Figure 22B:
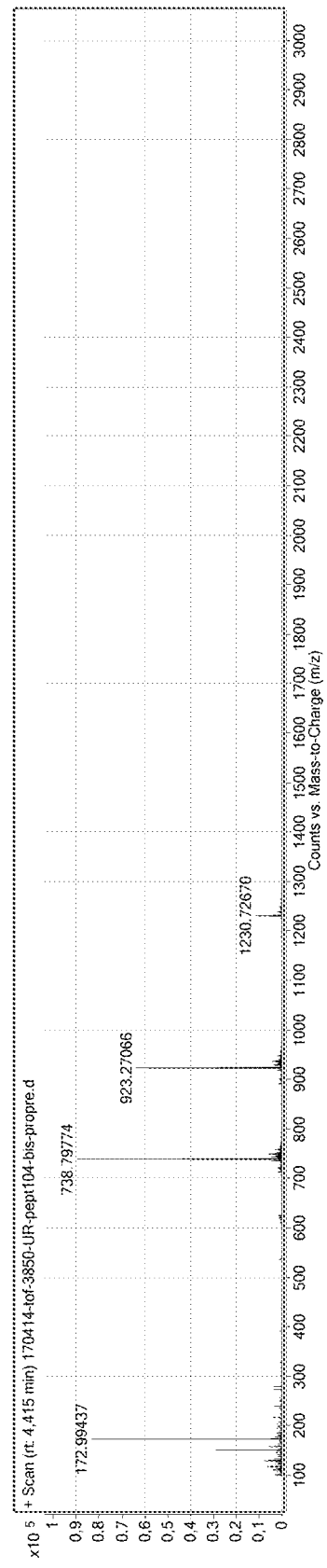
Figure 23A:
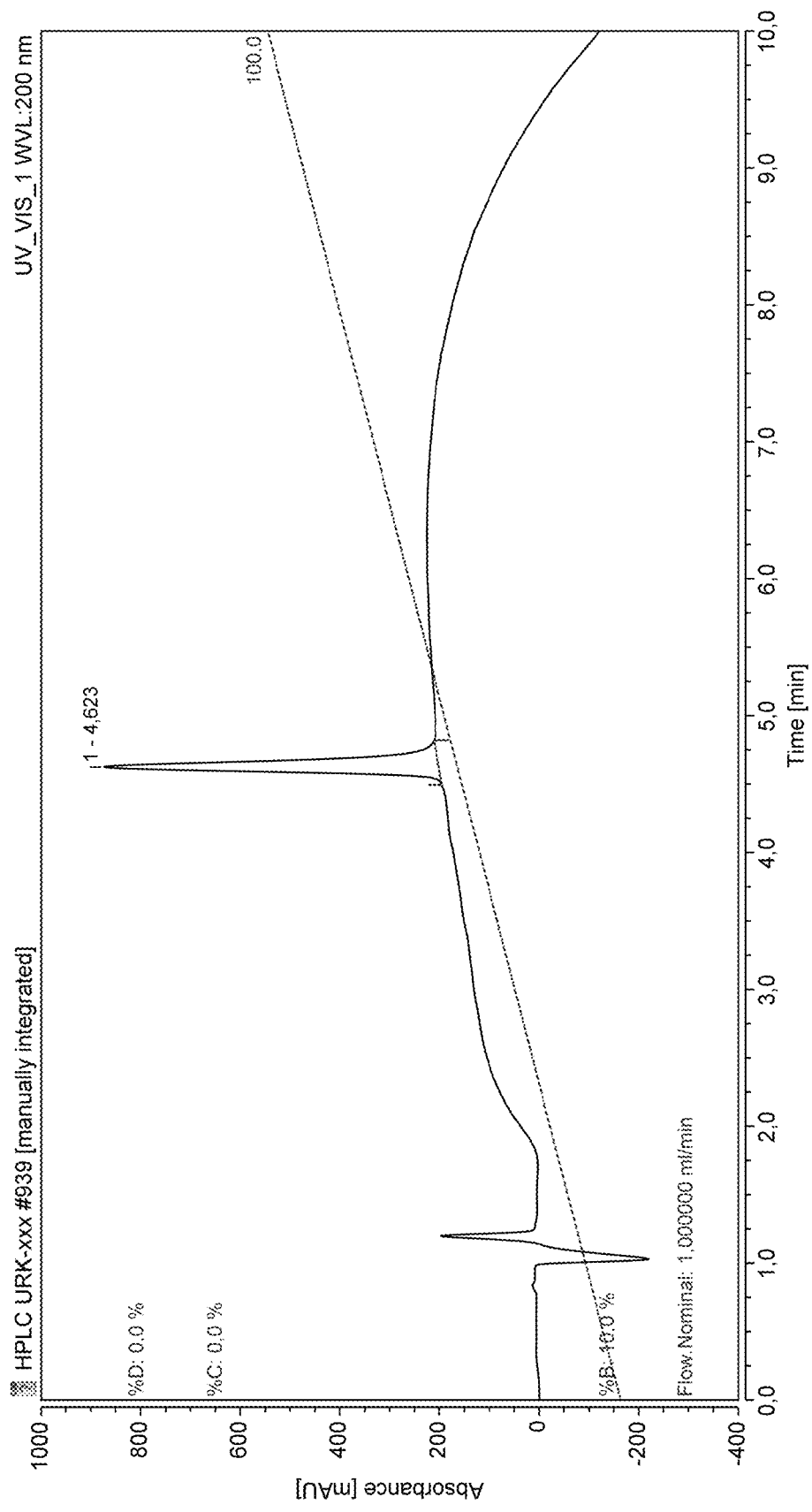
FIG. 23A and FIG. 23B. (A) HPLC profile of peptide 19 (10-100%; $CH_3CN$ 0.1% TFA in $H_2O$ 0.1% TFA, 10 min, C18). (B) LC-MS spectrum of peptide 19.
Figure 23B:
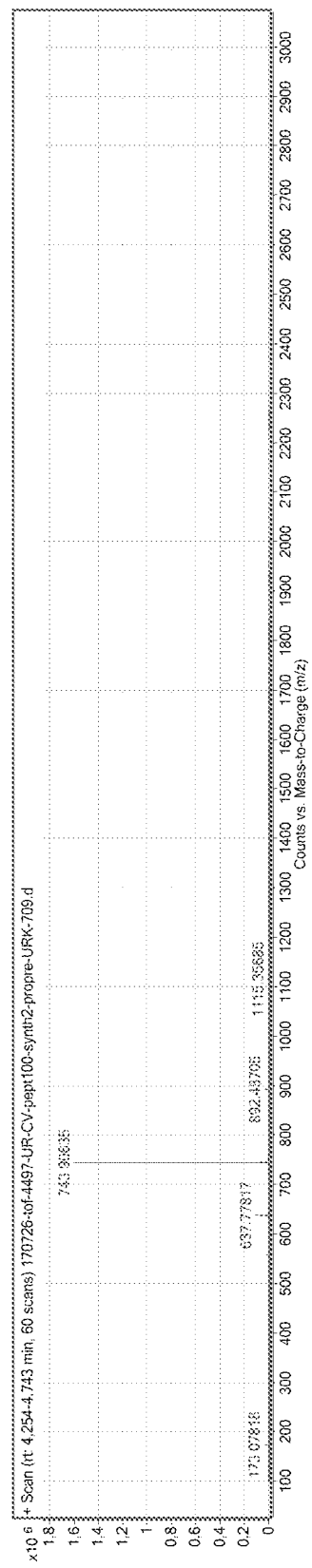
Figure 24A:
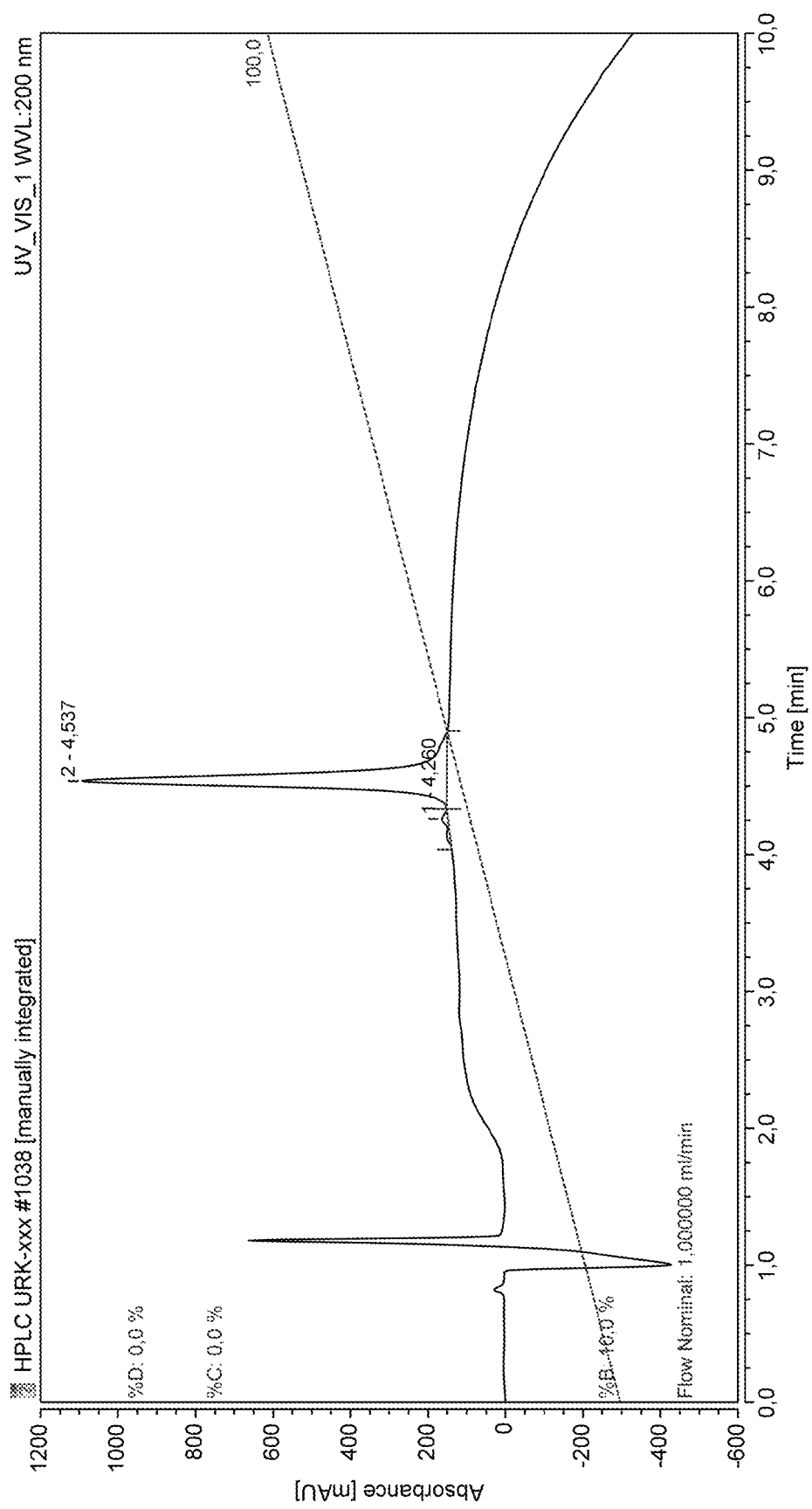
FIG. 24A and FIG. 24B. (A) HPLC profile of peptide 20 (10-100%; $CH_3CN$ 0.1% TFA in $H_2O$ 0.1% TFA, 10 min, C18). (B) LC-MS spectrum of peptide 20.
Figure 24B:
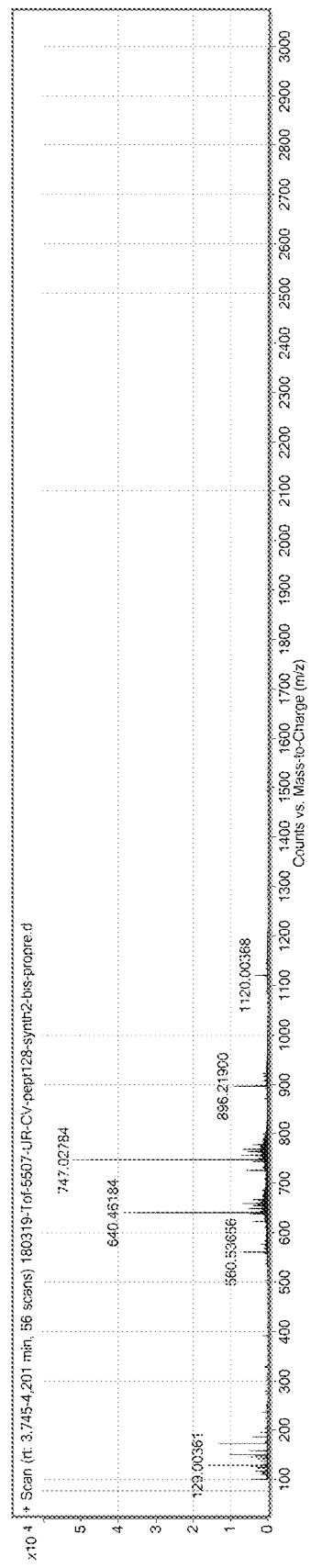
Figure 25A:
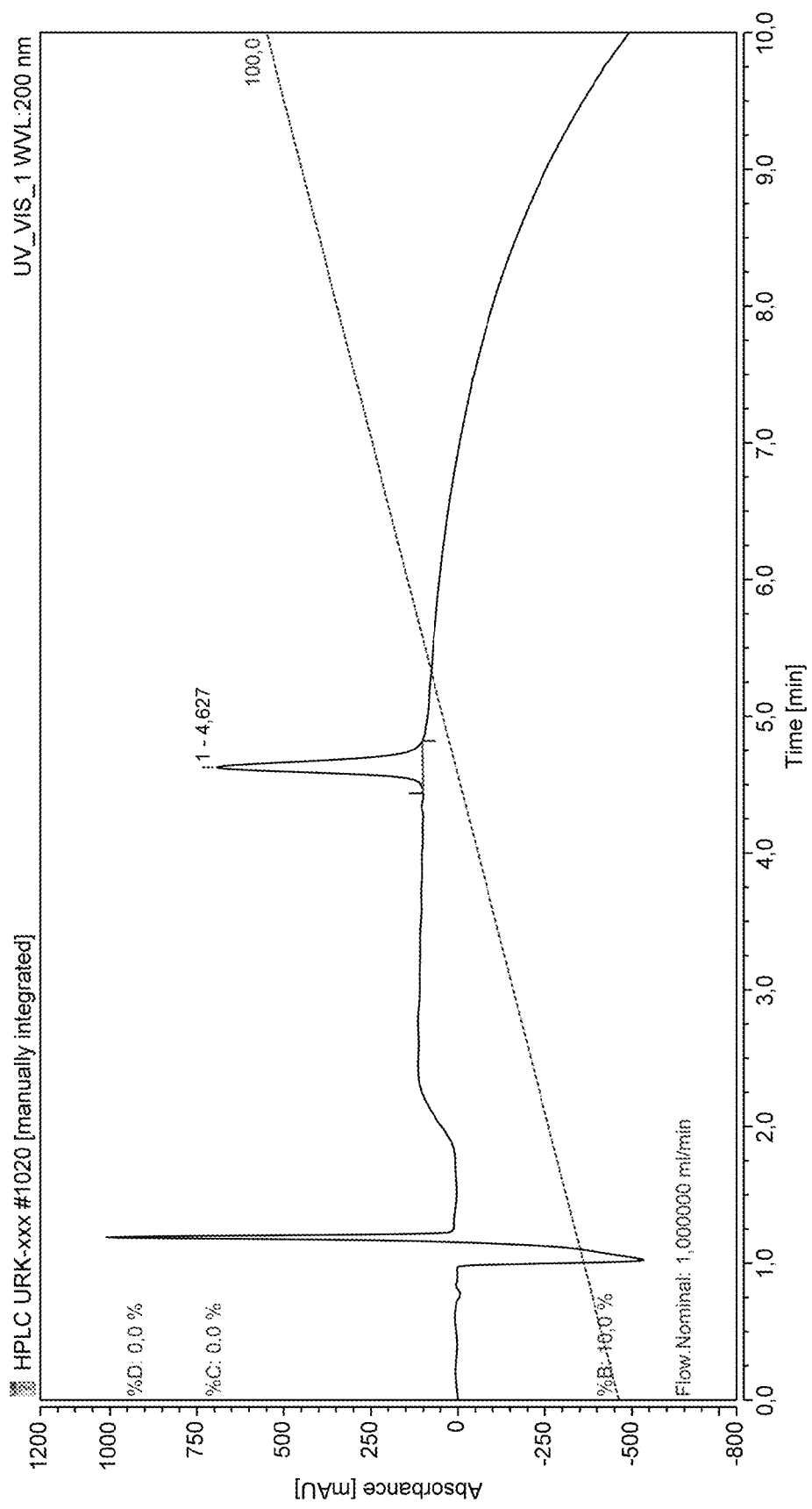
FIG. 25A and FIG. 25B. (A) HPLC profile of peptide 21 (10-100%; $CH_3CN$ 0.1% TFA in $H_2O$ 0.1% TFA, 10 min, C18). (B) LC-MS spectrum of peptide 21.
Figure 25B:
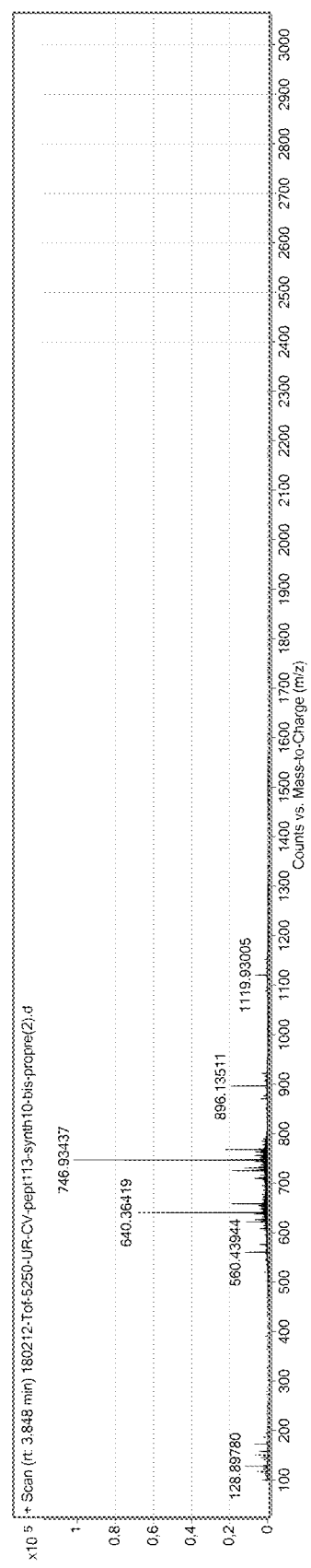
Figure 26A:
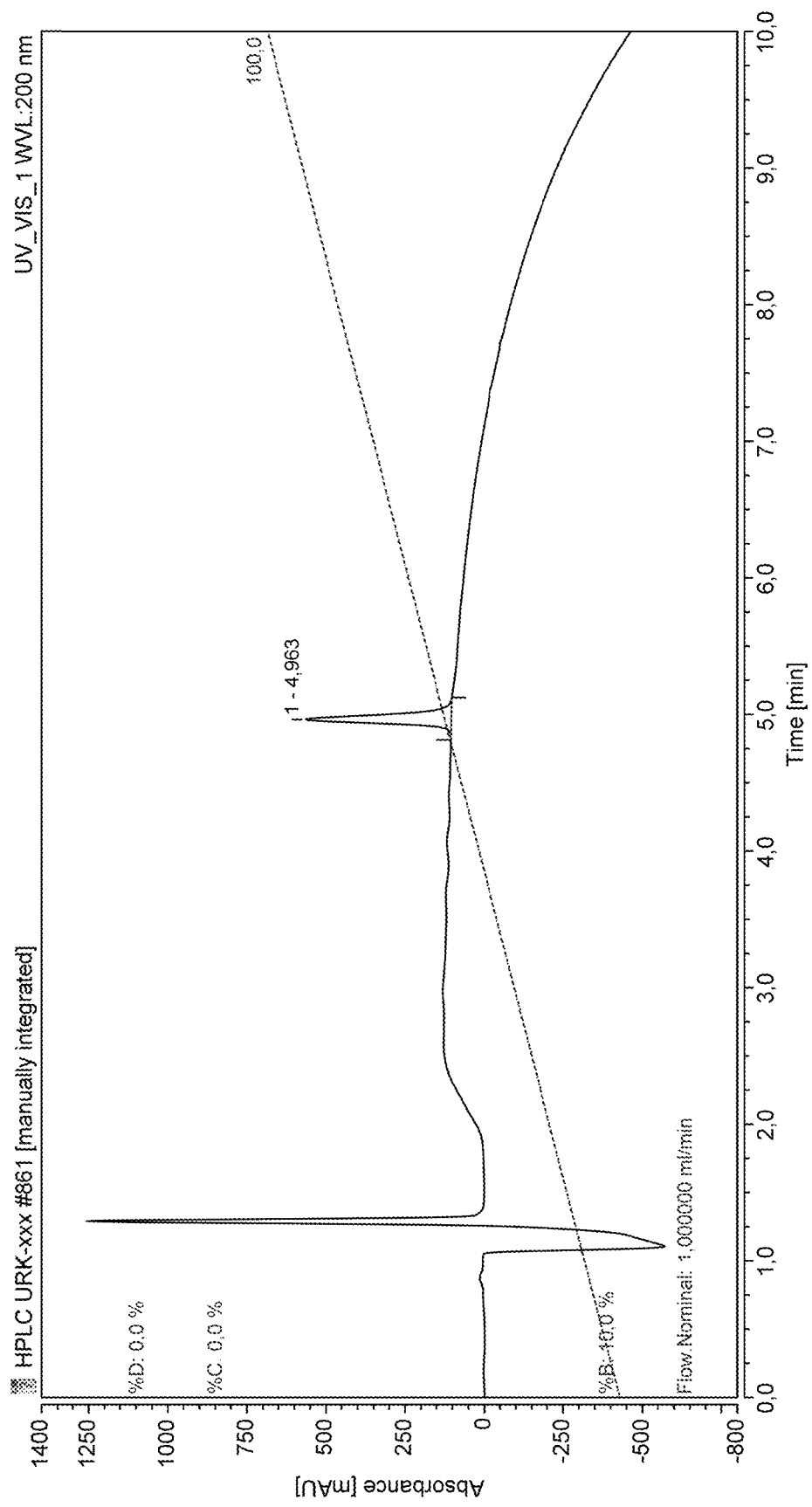
FIG. 26A and FIG. 26B. (A) HPLC profile of peptide 22 (10-100%; $CH_3CN$ 0.1% TFA in $H_2O$ 0.1% TFA, 10 min, C18). (B) LC-MS spectrum of peptide 22.
Figure 26B:
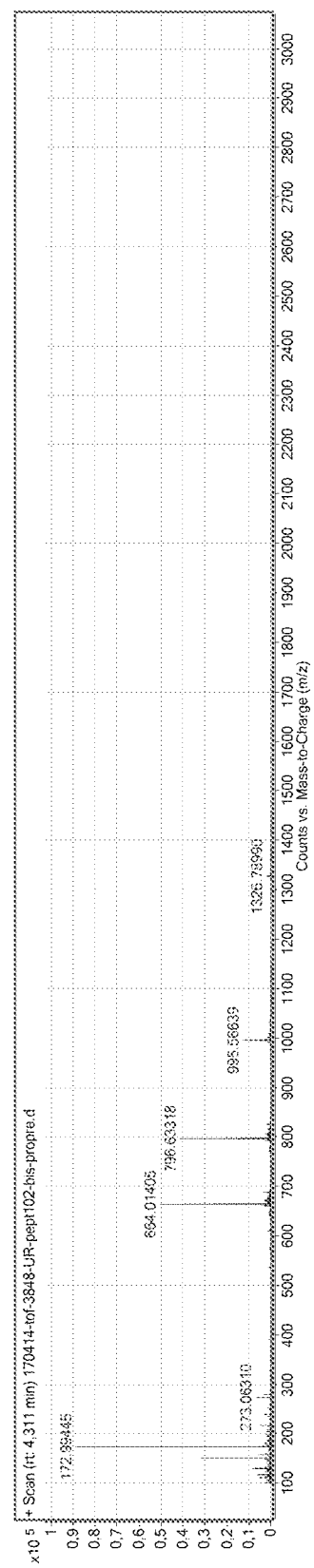
Figure 27A:
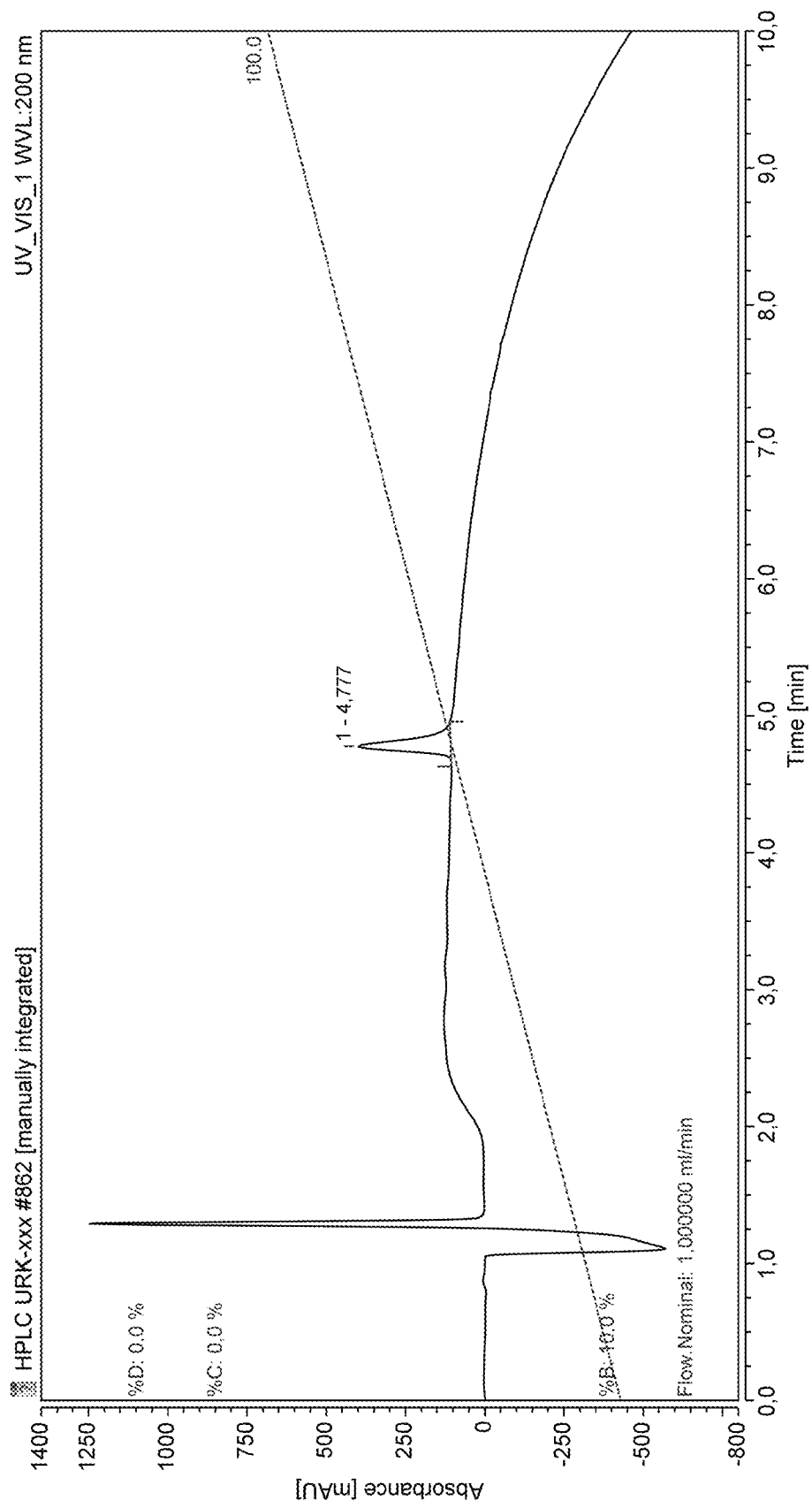
FIG. 27A and FIG. 27B. (A) HPLC profile of peptide 23 (10-100%; $CH_3CN$ 0.1% TFA in $H_2O$ 0.1% TFA, 10 min, C18). (B) LC-MS spectrum of peptide 23.
Figure 27B:
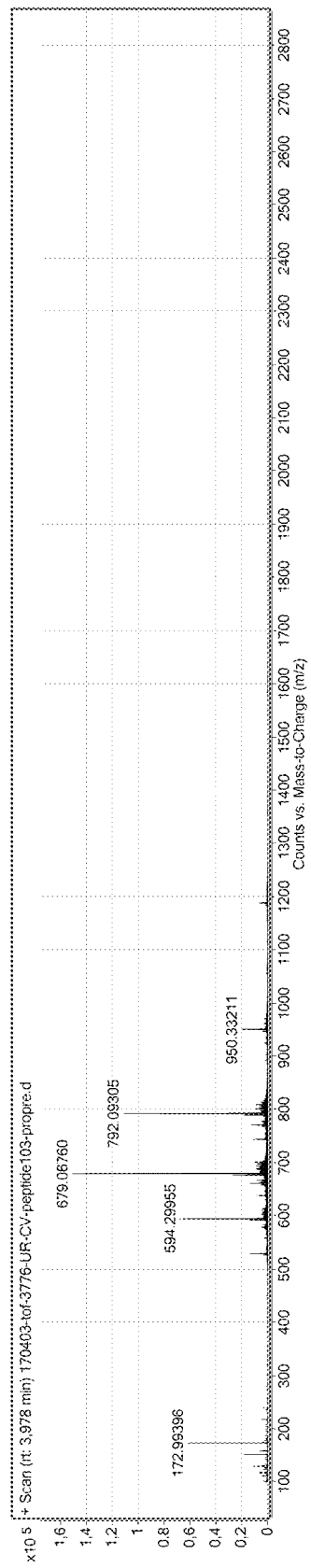
Figure 28A:
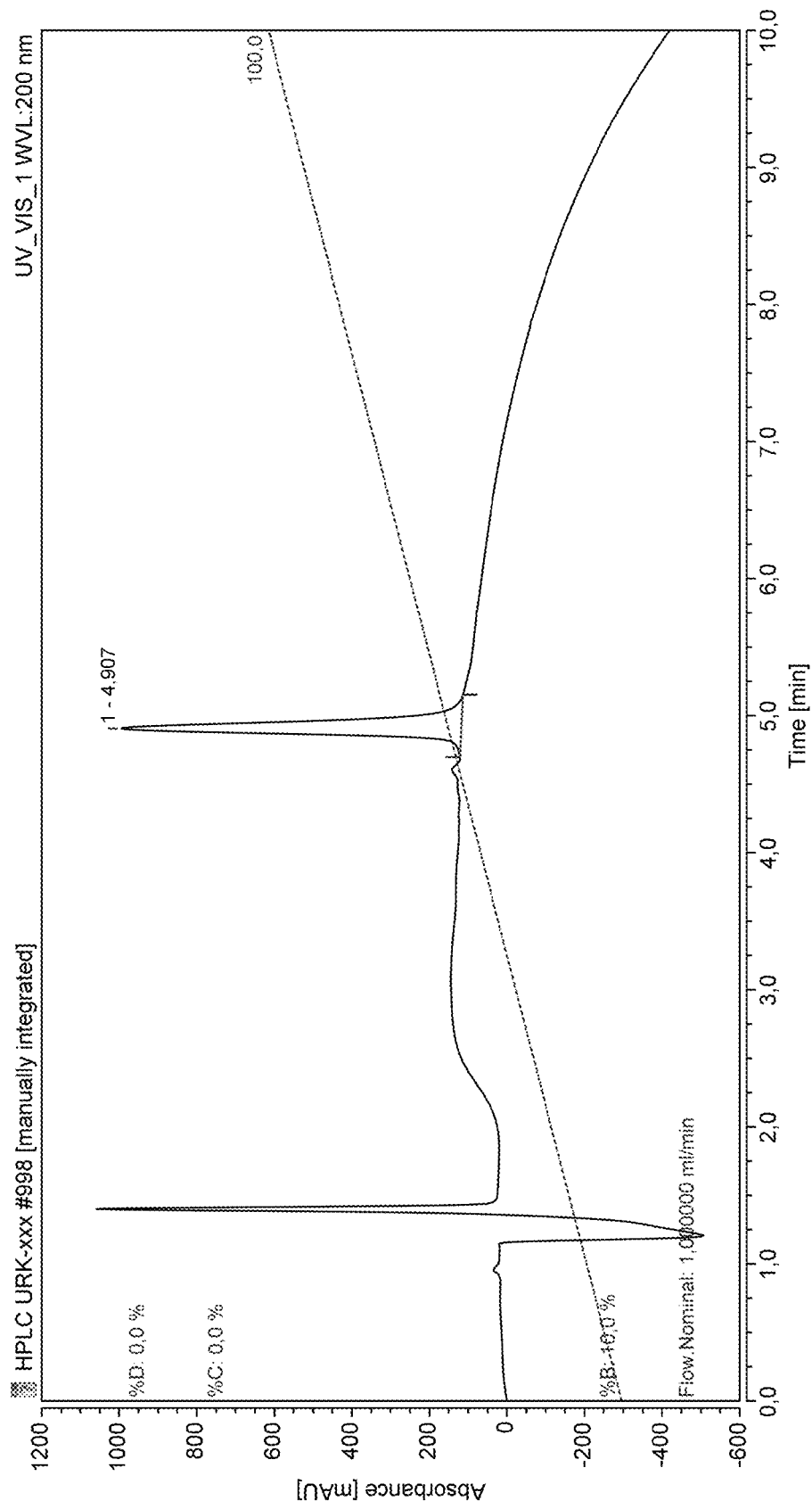
FIG. 28A and FIG. 28B. (A) HPLC profile of peptide 24 (10-100%; $CH_3CN$ 0.1% TFA in $H_2O$ 0.1% TFA, 10 min, C18). (B) LC-MS spectrum of peptide 24.
Figure 28B:
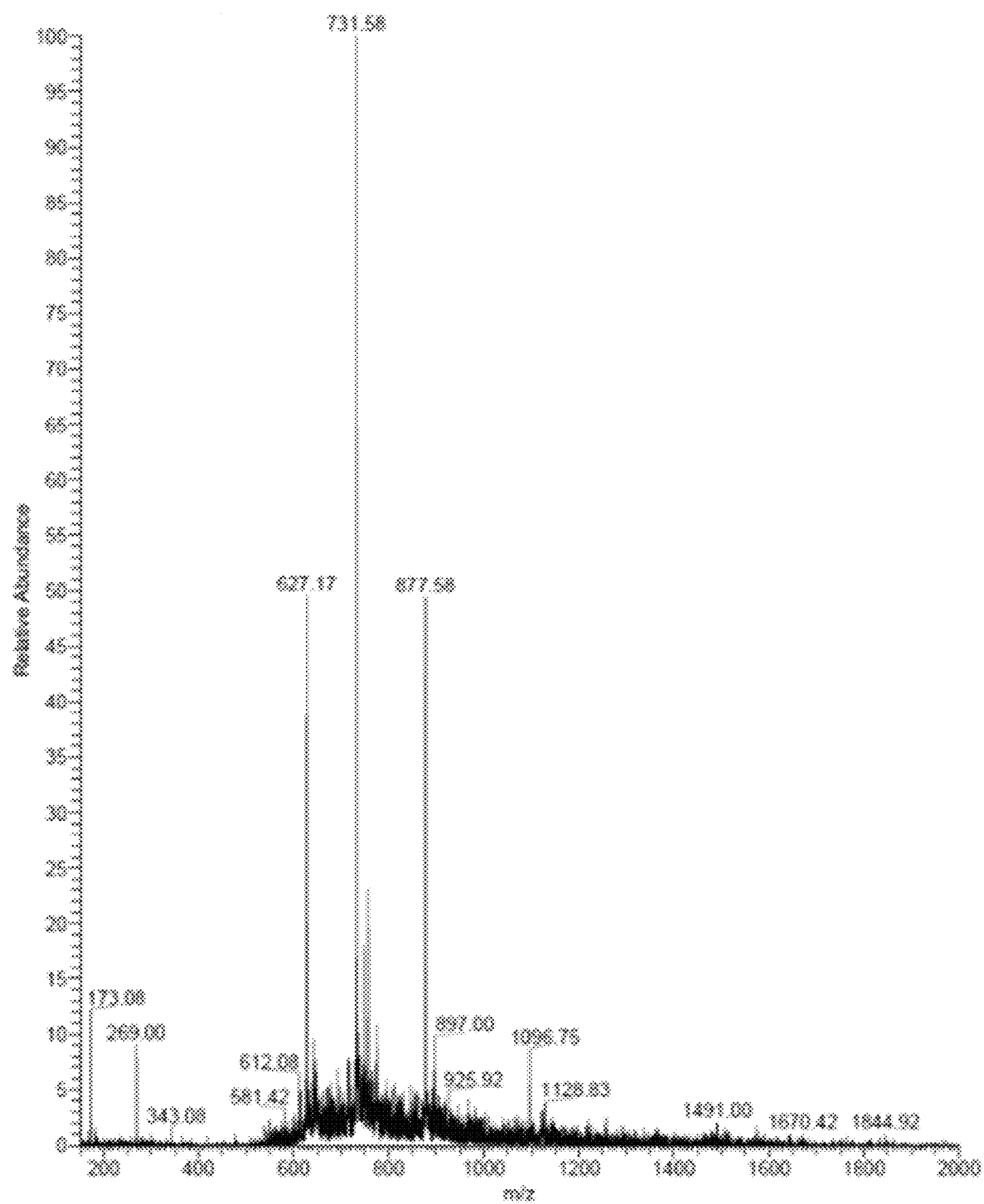
Figure 29A:
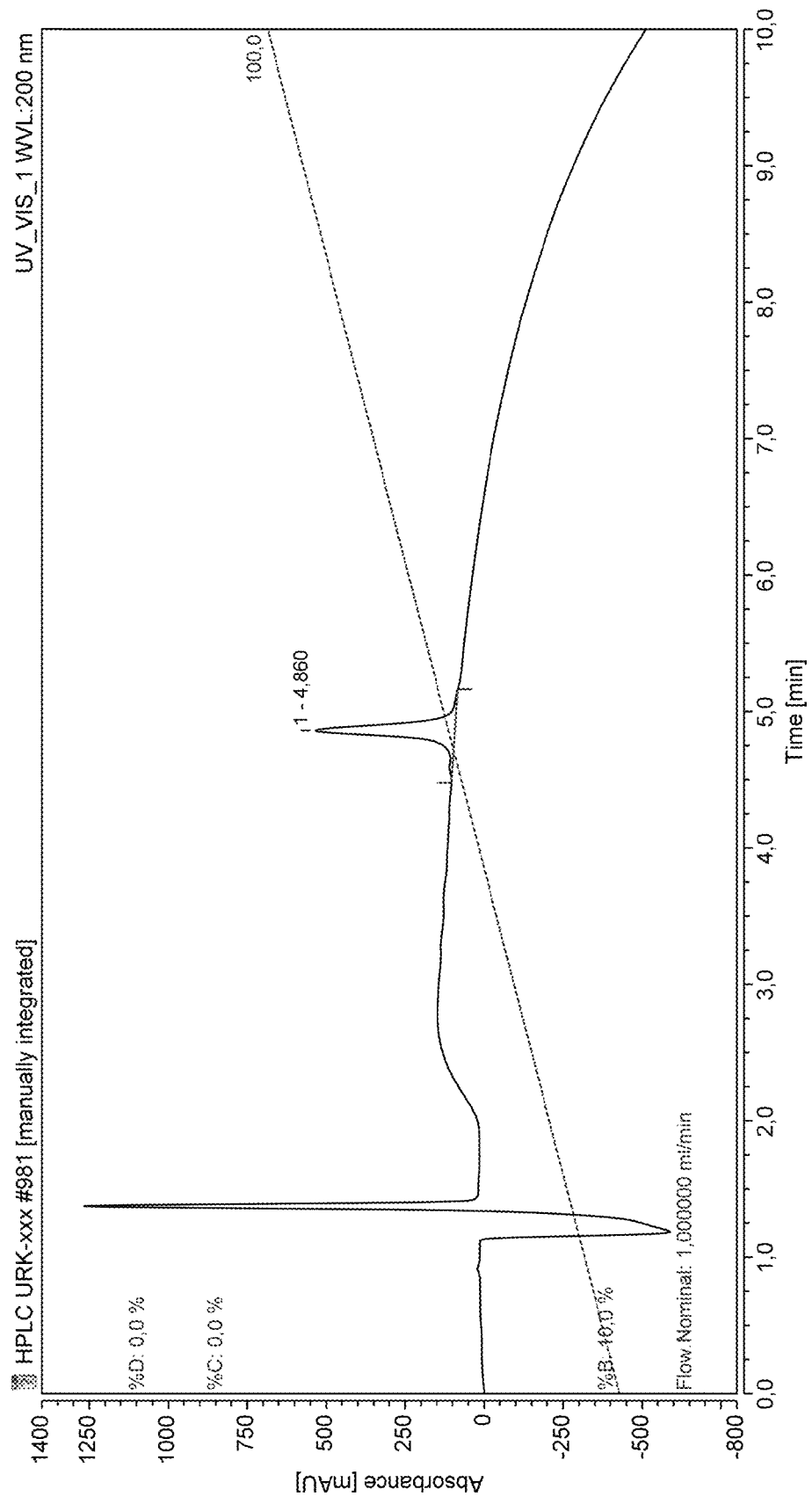
FIG. 29A and FIG. 29B. (A) HPLC profile of peptide 25 (10-100%; $CH_3CN$ 0.1% TFA in $H_2O$ 0.1% TFA, 10 min, C18). (B) LC-MS spectrum of peptide 25.
Figure 29B:
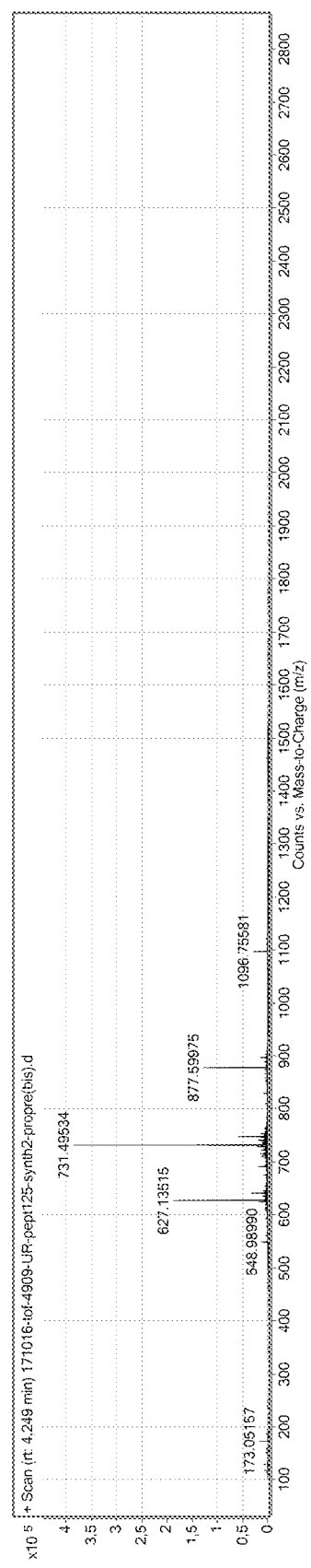

The rats (Wistar Rat, males, 8-week old, n=6 or 3) were housed in ventilated and enriched housing cages (310×125×127 mm$^3$) throughout the experimental phase. They were housed in groups of 3 animals during the study, on a normal 12 hours light cycle (lights off at 08:00 PM), 22±2° C. and 50±10% relative humidity. The rates were acclimated for 5 days with standard diet and tap water. Then, after 3 hours fasting, they were treated with glucagon (10) or analogs 13, 14, 19, 21, and 25 (10 nM/kg) via i.v. route. Blood glucose was measured before dosing and after at different time, as shown in FIGS. 12 and 13. As shown in FIGS. 12 and 13, the glucagon analogs provided greater glycogen breakdown, compared to glucagon, as demonstrated by the increased blood glucose levels in the rats.

Peptide Characterization.

```
Peptide 10:
HSQGTFTSDYSKYLDSRRAQDFVQWLMNT-OH
```

Peptide 10 was synthesized using the general procedure A2 starting from Wang resin (196 mg, 0.1 mmol) and cleaved using procedure C2. The final product 10 was purified by semi-preparative HPLC. 1.88 mg was obtained (yield 0.54%). HPLC: R$_t$=5.03 min (10-100%; CH$_3$CN 0.1% TFA in H$_2$O 0.1% TFA, 10 min, C18); LC-MS (m/z 3482.40): 697.48 [M+5H]$^{5+}$, 871.36 [M+4H]$^{4+}$, 1161.82 [M+3H]$^{3+}$.

```
Peptide 11:
HSQGTFTSDYSKYLDSRRAQDFVQWLMNT-NH$_2$
```

Peptide 11 was synthesized using the general procedure A1 starting from Sieber resin (160 mg, 0.1 mmol) and cleaved using procedure C2. The final product 11 was purified by semi-preparative HPLC. 1.59 mg was obtained (yield 0.45%). HPLC: $R_t$=5.03 min (10-100%; $CH_3CN$ 0.1% TFA in $H_2O$ 0.1% TFA, 10 min, C18); LC-MS (m/z 3481.75): 697.35 $[M+5H]^{5+}$, 871.44 $[M+4H]^{4+}$, 1161.59 $[M+3H]^{3+}$.

Peptide 12:
KPHSQGTFTSDYSKYLDSRRAQDFVQWLLNT-NH2

Peptide 12 was synthesized using the general procedure A1 starting from Sieber resin (160 mg, 0.1 mmol) and cleaved using procedure C1. The final product 12 was purified by semi-preparative HPLC. 9.26 mg was obtained (yield 2.50%). HPLC: $R_t$=5.06 min (10-100%; $CH_3CN$ 0.1% TFA in $H_2O$ 0.1% TFA, 10 min, C18); LC-MS (m/z 3688.65): 615.77 $[M+6H]^{6+}$ 738.73 $[M+5H]^{5+}$, 923.17 $[M+4H]^{4+}$, 1230.57 $[M+3H]^{3+}$.

Peptide 13:
KPKPHSQGTFTSDYSKYLDSRRAQDFVQWLLNT-NH2

Peptide 13 was synthesized using the general procedure A1 starting from Sieber resin (160 mg, 0.1 mmol) and cleaved using procedure C1. The final product 13 was purified by semi-preparative HPLC. 16.0 mg was obtained (yield 4.1%). HPLC: $R_t$=5.06 min (10-100%; $CH_3CN$ 0.1% TFA in $H_2O$ 0.1% TFA, 10 min, C18); LC-MS (m/z 3914.15): 653.36 $[M+6H]^{6+}$ 783.83 $[M+5H]^{5+}$, 979.53 $[M+4H]^{4+}$.

Peptide 14:
KPKPKPHSQGTFTSDYSKYLDSRRAQDFVQWLLNT-NH2

Peptide 14 was synthesized using the general procedure A1 starting from Sieber resin (160 mg, 0.1 mmol) and cleaved using procedure C1. The final product 14 was purified by semi-preparative HPLC. 8.0 mg was obtained (yield 1.9%). HPLC: $R_t$=4.91 min (10-100%; $CH_3CN$ 0.1% TFA in $H_2O$ 0.1% TFA, 10 min, C18); LC-MS (m/z 4138.20): 592.16 $[M+7H]^{7+}$ 690.7 $[M+6H]^{6+}$ 828.66 $[M+5H]^{5+}$, 1035.60 $[M+4H]^{4+}$.

Peptide 15:
KPHSQGTFTSDYSKYLDSRRAQDFVQWLMNT-NH2

Peptide 15 was synthesized using the general procedure A1 starting from Sieber resin (160 mg, 0.1 mmol) and cleaved using procedure C2. The final product 15 was purified by semi-preparative HPLC. 2.86 mg was obtained (yield 0.77%). HPLC: $R_t$=5.01 min (10-100%; $CH_3CN$ 0.1% TFA in $H_2O$ 0.1% TFA, 10 min, C18); LC-MS (m/z 3706.93): 618.82 $[M+6H]^{6+}$ 742.39 $[M+5H]^{5+}$, 927.73 $[M+4H]^{4+}$.

Peptide 16:
KPKPHSQGTFTSDYSKYLDSRRAQDFVQWLMNT-NH2

Peptide 16 was synthesized using the general procedure A1 starting from Sieber resin (160 mg, 0.1 mmol) and cleaved using procedure C2. The final product 16 was purified by semi-preparative HPLC. 6.48 mg was obtained (yield 1.6%). HPLC: $R_t$=4.94 min (10-100%; $CH_3CN$ 0.1% TFA in $H_2O$ 0.1% TFA, 10 min, C18); LC-MS (m/z 3932.1): 656.35 $[M+6H]^{6+}$ 787.42 $[M+5H]^{5+}$, 984.02 $[M+4H]^{4+}$.

Peptide 17:
KPKPKPHSQGTFTSDYSKYLDSRRAQDFVQWLMNT-NH2

Peptide 17 was synthesized using the general procedure A1 starting from Sieber resin (160 mg, 0.1 mmol) and cleaved using procedure C2. The final product 17 was purified by semi-preparative HPLC. 7.99 mg was obtained (yield 1.9%). HPLC: $R_t$=4.93 min (10-100%; $CH_3CN$ 0.1% TFA in $H_2O$ 0.1% TFA, 10 min, C18); LC-MS (m/z 4157.22): 594.89 $[M+7H]^{7+}$ 693.87 $[M+6H]^{6+}$ 832.45 $[M+5H]^{5+}$, 1040.31 $[M+4H]^{4+}$.

Peptide 18:
EPHSQGTFTSDYSKYLDSRRAQDFVQWLLNT-NH2

Peptide 18 was synthesized using the general procedure A1 starting from Sieber resin (160 mg, 0.1 mmol) and cleaved using procedure C1. The final product 18 was purified by semi-preparative HPLC. 8.07 mg was obtained (yield 2.2%). HPLC: $R_t$=5.04 min (10-100%; $CH_3CN$ 0.1% TFA in $H_2O$ 0.1% TFA, 10 min, C18); LC-MS (m/z 3689.19): 738.8 $[M+5H]^{5+}$, 923.27 $[M+4H]^{4+}$, 1230.73 $[M+3H]^{3+}$.

Peptide 19:
K*PHSQGTFTSDYSKYLDSRRAQDFVQWLLNT-NH2, wherein K* is a lysine modified with KKKKKK Peptide 19 was synthesized using the general procedure A1 starting from Sieber resin (160 mg, 0.1 mmol) and cleaved using procedure C1. The final product 19 was purified by semi-preparative HPLC. 17.15 mg was obtained (yield 3.8%). HPLC: $R_t$=4.62 min (10-100%; $CH_3CN$ 0.1% TFA in $H_2O$ 0.1% TFA, 10 min, C18); LC-MS (m/z 4457.46): 637.78 $[M+7H]^{7+}$, 743.91 $[M+6H]^{6+}$, 892.49 $[M+5H]^{5+}$, 1115.36 $[M+4H]^{4+}$.

Peptide 20:
K*PHSQGTFTSDYSKYLDSRRAQDFVQWLMNT-NH2, wherein K* is a lysine modified with KKKKKK Peptide 20 was synthesized using the general procedure A1 starting from Rink resin (227 mg, 0.1 mmol) and cleaved using procedure C2. The final product 20 was purified by semi-preparative HPLC. 1.9 mg was obtained (yield 0.4%). HPLC: $R_t$=4.54 min (10-100%; $CH_3CN$ 0.1% TFA in $H_2O$ 0.1% TFA, 10 min, C18); LC-MS (m/z 4476.18): 560.54 $[M+8H]^{8+}$, 640.46 $[M+7H]^{7+}$, 747.03 $[M+6H]^{6+}$, 896.22 $[M+5H]^{5+}$, 1120.00 $[M+4H]^{4+}$.

Peptide 21:
K*PHSQGTFTSDYSKYLDSRRAQDFVQWLMNT-OH, wherein K* is a lysine modified with KKKKKK Peptide 21 was synthesized using the general procedure A2 starting from Wang resin (227 mg, 0.1 mmol) cleaved using procedure C2. The final product 21 was purified by semi-preparative HPLC. 28.11 mg was obtained (yield 6.3%). HPLC: $R_t$=4.63 min (10-100%; $CH_3CN$ 0.1% TFA in $H_2O$ 0.1% TFA, 640.36 [M+7H]$^{7+}$, 746.93 [M+6H]$^{6+}$, 896.14 [M+5H]$^{5+}$, 1119.93 [M+4H]$^{4+}$

```
Peptide 22:
K*PHSQGTFTSDYSKYLDSRRAQDFVQWLLNT-NH₂,
``` wherein K* is a lysine modified with 8Ado8Ado

Peptide 22 was synthesized using the general procedure A1 starting from Sieber resin (227 mg, 0.1 mmol) cleaved using procedure C1. The final product 22 was purified by semi-preparative HPLC. 1.9 mg was obtained (yield 0.4%). HPLC: $R_t$=4.96 min (10-100%; CH$_3$CN 0.1% TFA in H$_2$O 0.1% TFA, 10 min, C18); LC-MS (m/z 3978.06): 644.01 [M+6H]$^{6+}$, 796.63 [M+5H]$^{5+}$, 995.57 [M+4H]$^{4+}$, 1326.79 [M+3H]$^{3+}$.

```
Peptide 23:
K*PHSQGTFTSDYSKYLDSRRAQDFVQWLLNT-NH₂,
``` wherein K* is a lysine modified with KKKKKK8Ado8Ado

Peptide 23 was synthesized using the general procedure A1 starting from Sieber resin (227 mg, 0.1 mmol) and cleaved using procedure C1. The final product 23 was purified by semi-preparative HPLC. 11.99 mg was obtained (yield 2.5%). HPLC: $R_t$=4.78 min (10-100%; CH$_3$CN 0.1% TFA in H$_2$O 0.1% TFA, 10 min, C18); LC-MS (m/z 4748.44): 594.30 [M+8H]$^{8+}$, 679.07 [M+7H]$^{7+}$, 792.09 [M+5H]$^{5+}$, 950.3 [M+4H]$^{4+}$.

```
Peptide 24:
K*PHSQGTFTSDYSKYLDSRRAQDFVQWLMNT-NH₂,
``` wherein K* is a lysine modified with KPKPKP

Peptide 24 was synthesized using the general procedure A1 starting from Rink resin (227 mg, 0.1 mmol) and cleaved using procedure C2. The final product 24 was purified by semi-preparative HPLC. 5.0 mg was obtained (yield 1.1%). HPLC: $R_t$=4.91 min (10-100%; CH$_3$CN 0.1% TFA in H$_2$O 0.1% TFA, 10 min, C18); LC-MS (m/z 4382.98): 627.17 [M+7H]$^{7+}$, 731.58 [M+6H]$^{6+}$, 877.58 [M+5H]$^{5+}$, 1096.75 [M+4H]$^{4+}$.

```
Peptide 25:
K*PHSQGTFTSDYSKYLDSRRAQDFVQWLMNT-OH,
``` wherein K* is a lysine modified with KPKPKP.

Peptide 25 was synthesized using the general procedure A2 starting from Wang resin (216 mg, 0.1 mmol) and cleaved using procedure C2. The final product 25 was purified by semi-preparative HPLC. 7.02 mg was obtained (yield 1.6%). HPLC: $R_t$=4.86 min (10-100%; CH$_3$CN 0.1% TFA in H$_2$O 0.1% TFA, 10 min, C18); LC-MS (m/z 4383.96): 627.14 [M+7H]$^{7+}$, 731.50 [M+6H]$^{6+}$, 877.60 [M+5H]$^{5+}$, 1096.76 [M+4H]$^{4+}$.

Specific Embodiments

According to an aspect, the present disclosure provides a pro-drug peptide or salt thereof having improvement for at least one biological property relative to a parent peptide or peptidomimetic, wherein the biological property is selected from the group consisting of therapeutic index, stability, solubility, toxicity, adsorption, and pre-systemic metabolism, the pro-drug peptide comprising the following structure: $Z_n$-pep, wherein: pep is the parent peptide or peptidomimetic; Z is a sequence of n amino acids, wherein Z is cleaved in vivo releasing pep, and n is an integer ≥2 (e.g., 2, 3, 4, 5, 6, 7, 8, 9, or 10 or more).

In any aspect or embodiment described herein, the Z has the following structure: (Glu-Pro)$_m$ or (Lys-Pro)$_X$, wherein X is an integer ≥1 (e.g., 1, 2, 3, 4, 5, 6, 7, 8, 9, or 10 or more).

In any aspect or embodiment described herein, the Z is selected from the group consisting of EP, KP, EPEP, KPKP, EPEPEP, and KPKPKP.

In any aspect or embodiment described herein, at least the first Lys of Z is functionalized with a soluble compound.

In any aspect or embodiment described herein, at least two Lys of Z are functionalized with the soluble compound.

In any aspect or embodiment described herein, the Z comprises two amino acids, and the first amino acid is functionalized with a soluble compound.

In any aspect or embodiment described herein, the soluble compound is aqueously soluble.

In any aspect or embodiment described herein, the first amino acid of Z is functionalized with a soluble compound or moiety comprising: 12-aminododecanoic acid (Ado), Ado-Ado-(Lys)$_m$, 8-amino-3,6-dioxaoctanoic acid (8Ado), 8Ado-8Ado-(Lys)$_m$, (Lys)$_m$, or (Pro-Lys)$_m$, wherein m is an integer from 0-10.

In any aspect or embodiment described herein, at least two Lys of Z are functionalized with a soluble compound or moiety comprising: Ado, Ado-Ado-(Lys)$_m$, 8Ado, 8Ado-8Ado-(Lys)$_m$, (Lys)$_m$, or (Pro-Lys)$_m$, wherein m is an integer from 0-10.

In any aspect or embodiment described herein, the c-terminus of the peptide is amine modified or amidated.

In any aspect or embodiment described herein, the parent peptide or peptidomimetic has an amino acid sequence that is at least 85% identical to a sequence selected from the group consisting of SEQ ID NO: 1 (HSQGTFTSDYSKY-LDSRRAQDFVQWLMNT) and SEQ ID NO: 2 (HSQGTFTSDYSKYLDSRRAQDFVQWLLNT).

According to another aspect, the present disclosure provides a pharmaceutical composition comprising: an effective amount of the pro-drug of the present disclosure, and a pharmaceutically acceptable excipient or carrier.

According to yet another aspect, the present disclosure provides a method of treating or preventing hypoglycemia or a hypoglycemia related disorder or disease, the method comprising: administering an effective amount of the pro-drug peptide of the present disclosure or the pharmaceutical composition of the present disclosure, wherein the pro-drug peptide is effective at treating or preventing hypoglycemia or the hypoglycemia related disorder or disease.

According to a further aspect, the present disclosure provides a method of preparing a pro-drug peptide or salt thereof having improvement for at least one biological property relative to a parent peptide or peptidomimetic, wherein the biological property is selected from the group consisting of therapeutic index, stability, solubility, toxicity, adsorption, and pre-systemic metabolism. The method comprising: adding a pro-drug portion to the parent peptide or peptidomimetic, wherein the pro-drug portion comprises ≥2 amino acids that are cleaved in vivo releasing the peptide or peptidomimetic.

In any aspect or embodiment described herein, the pro-drug portion has the following structure: (Glu-Pro)$_m$ or (Lys-Pro)$_X$, wherein X is ≥1 (e.g., 1, 2, 3, 4, 5, 6, 7, 8, 9, or 10 or more).

In any aspect or embodiment described herein, the pro-drug portion is selected from the group consisting of EP, KP, EPEP, KPKP, EPEPEP, and KPKPKP.

In any aspect or embodiment described herein, at least the first Lys of the pro-drug portion is functionalized with a soluble compound or moiety.

In any aspect or embodiment described herein, at least two Lys of the pro-drug portion are functionalized with the soluble compound or moiety.

In any aspect or embodiment described herein, the pro-drug portion comprises two amino acids, and the first amino acid is functionalized with the soluble compound or moiety.

In any aspect or embodiment described herein, the soluble compound is hydrophilic (i.e., soluble in aqueous solution).

In any aspect or embodiment described herein, the first amino acid of the pro-drug portion is functionalized with a soluble compound or moiety comprising: 12-aminododecanoic acid (Ado), Ado-Ado-(Lys)$_m$, 8-amino-3,6-dioxaoctanoic acid (8Ado), 8Ado-8Ado-(Lys)$_m$, (Lys)$_m$, or (Pro-Lys)$_m$, wherein m is an integer from 0-10.

In any aspect or embodiment described herein, at least two Lys of the pro-drug portion is functionalized with a soluble compound or moiety comprising: Ado, Ado-Ado-(Lys)$_m$, 8Ado, 8Ado-8Ado-(Lys)$_m$, (Lys)$_m$, or (Pro-Lys)$_m$, wherein m is an integer from 0-10.

In any aspect or embodiment described herein, the c-terminus of the peptide is amine modified or amidated.

In any aspect or embodiment described herein, the parent peptide or peptidomimetic has an amino acid sequence that is at least 85% identical to a sequence selected from the group consisting of SEQ ID NO: 1 (HSQGTFTSDYSKYLDSRRAQDFVQWLMNT) and SEQ ID NO: 2 (HSQGTFTSDYSKYLDSRRAQDFVQWLLNT).

In any aspect or embodiment describe herein, the peptide or peptidomimetic includes or is a peptide selected from SEQ ID NO: 3-10 and 11-25.

In any aspect or embodiment described herein, the peptide or peptidomimetic includes or is elected from 2-9 and 11-25.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A pro-drug peptide or salt thereof having improvement for at least one biological property relative to a parent peptide or peptidomimetic, wherein the biological property is selected from the group consisting of therapeutic index, stability, solubility, toxicity, adsorption, and pre-systemic metabolism, the pro-drug peptide comprising the following structure:

$Z_n$-pep, wherein:
pep is the parent peptide or peptidomimetic that is glucagon or an analog thereof; and
Z is attached to the n-terminus of pep and is cleaved in vivo releasing pep, wherein Z has the structure (Glu-Pro)$_X$ or (Lys-Pro)$_X$, and X is an integer ≥1.

2. The pro-drug peptide of claim 1, wherein the Z has the structure (Lys-Pro)$_X$.

3. The pro-drug peptide of claim 1, wherein the Z is selected from the group consisting of EP, KP, EPEP, KPKP, EPEPEP, and KPKPKP.

4. The pro-drug peptide of claim 2, wherein at least the first Lys of Z is functionalized with a soluble compound or moiety.

5. The pro-drug peptide of claim 2, wherein at least two Lys of Z are functionalized with the soluble compound or moiety.

6. The pro-drug peptide of claim 1, wherein the Z comprises two amino acids, and the first amino acid is functionalized with a soluble compound or moiety.

7. The pro-drug peptide of claim 4, wherein the soluble compound or moiety is hydrophilic.

8. The pro-drug peptide of claim 1, wherein the first amino acid of Z is functionalized with a soluble compound or moiety comprising: 12-aminododecanoic acid (Ado), Ado-Ado, Ado-Ado-(Lys)$_m$, 8-amino-3,6-dioxaoctanoic acid (8Ado), 8Ado-8Ado, 8Ado-8Ado-(Lys)$_m$, (Lys)$_m$-8Ado-8Ado, (Lys)$_m$, or (Lys-Pro)$_m$, wherein m is an integer from 1-10.

9. The pro-drug peptide of claim 1, wherein at least two Lys of Z are functionalized with a soluble compound or moiety comprising: Ado, Ado-Ado, Ado-Ado-(Lys)$_m$, 8Ado, 8Ado-8Ado, 8Ado-8Ado-(Lys)$_m$, (Lys)$_m$-8Ado-8Ado, (Lys)$_m$, or (Lys-Pro)$_m$, wherein m is an integer from 1-10.

10. The pro-drug peptide of claim 1, wherein the c-terminus of the peptide is amine modified.

11. The pro-drug peptide of claim 1, wherein the parent peptide or peptidomimetic has an amino acid sequence that is at least 85% identical to a sequence selected from the group consisting of SEQ ID NO: 1 (HSQGTFTSDYSKY-LDSRRAQDFVQWLMNT) and SEQ ID NO: 2 (HSQGTFTSDYSKYLDSRRAQDFVQWLLNT).

12. A pharmaceutical composition comprising: an effective amount of the pro-drug of claim 1, and a pharmaceutically acceptable excipient or carrier.

13. A method of treating or preventing hypoglycemia or a hypoglycemia related disorder or disease, the method comprising: administering an effective amount of the pharmaceutical composition of claim 12, wherein the pro-drug peptide is effective at treating or preventing hypoglycemia or the hypoglycemia related disorder or disease.

14. A method of preparing a pro-drug peptide or salt thereof having improvement for at least one biological property relative to a parent peptide or peptidomimetic, wherein the biological property is selected from the group consisting of therapeutic index, stability, solubility, toxicity, adsorption, and pre-systemic metabolism, the method comprising:
adding a pro-drug portion to the parent peptide or peptidomimetic,
wherein:
the pro-drug portion is cleaved in vivo releasing the peptide or peptidomimetic;
the pro-drug portion has the structure (Glu-Pro)$_X$ or (Lys-Pro)$_X$;
X is an integer ≥1; and
the parent peptide or peptidomimetic is glucagon or an analog thereof.

15. The method of claim 14, wherein:
the pro-drug portion has the structure (Lys-Pro)$_X$;
the pro-drug portion is selected from the group consisting of EP, KP, EPEP, KPKP, EPEPEP, and KPKPKP;
the first amino acid of the pro-drug portion is functionalized with a soluble compound or moiety comprising: 12-aminododecanoic acid (Ado), Ado-Ado, Ado-Ado- (Lys)$_m$, 8-amino-3,6-dioxaoctanoic acid (8Ado), 8Ado-8Ado, 8Ado-8Ado-(Lys)$_m$, (Lys)$_m$-8Ado-8Ado, (Lys)$_m$, or (Lys-Pro)$_m$, wherein m is an integer from 1-10;

the parent peptide or peptidomimetic has an amino acid sequence that is at least 85% identical to a sequence selected from the group consisting of SEQ ID NO: 1 (HSQGTFTSDYSKYLDSRRAQDFVQWLMNT) and SEQ ID NO: 2 (HSQGTFTSDYSKYLDSR-RAQDFVQWLLNT);

the method further comprises amidating the c-terminus of the peptide or modifying the c-terminus of the protein with an amine; or a combination thereof.

16. The method of claim 14, wherein at least the first Lys of the pro-drug portion is functionalized with a soluble compound or moiety.

17. The method of claim 14, wherein at least two Lys of the pro-drug portion are functionalized with the soluble compound or moiety.

18. The method of claim 14, wherein the pro-drug portion comprises two amino acids, and the first amino acid is functionalized with a soluble compound or moiety.

19. The method of claim 16, wherein the soluble compound or moiety is aqueously soluble.

20. The method of claim 15, wherein at least two Lys of the pro-drug portion is functionalized with a soluble compound or moiety comprising: Ado, Ado-Ado, Ado-Ado-(Lys)$_m$, 8Ado, 8Ado-8Ado, 8Ado-8Ado-(Lys)$_m$, (Lys)$_m$-8Ado-8Ado, (Lys)$_m$, or (Lys-Pro)$_m$, wherein m is an integer from 1-10.

21. The pro-drug peptide of claim 1, wherein the Z is KP.

22. The pro-drug peptide of claim 21, wherein the Lys of Z is functionalized with a soluble compound or moiety via an epsilon-N linkage.

23. The pro-drug peptide of claim 22, wherein the soluble compound or moiety comprises: 12-aminododecanoic acid (Ado), Ado-Ado, Ado-Ado-(Lys)$_m$, 8-amino-3,6-dioxaoctanoic acid (8Ado), 8Ado-8Ado, 8Ado-8Ado-(Lys)$_m$, (Lys)$_m$-8Ado-8Ado, (Lys)$_m$, or (Lys-Pro)$_m$, wherein m is an integer from 1-10.

24. The pro-drug peptide of claim 22, wherein the soluble compound or moiety is KP.

25. The pro-drug peptide of claim 1, wherein the parent peptide or peptidomimetic has an amino acid sequence that is at least 85% identical to the sequence of SEQ ID NO: 2 (HSQGTFTSDYSKYLDSRRAQDFVQWLMNT).

26. The pro-drug peptide of claim 25, wherein Z is KP.

27. The pro-drug peptide of claim 26, wherein the lysine of Z is functionalized with a soluble compound or moiety via an epsilon-N linkage.

28. The pro-drug peptide of claim 27, wherein the soluble compound or moiety is (Lys-Pro)$_m$, wherein m is 3.

29. The pro-drug peptide of claim 1, wherein:

the prodrug has the structure:
K*PHSQGTFTSDYSKYLDSRRAQDFVQWLMNT KPKPKP; and

K* is represented by the structure:

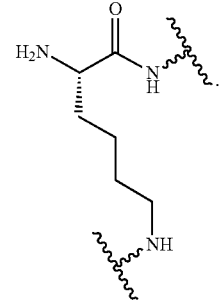

\* \* \* \* \*

SEQUENCE LISTING

```
<160> NUMBER OF SEQ ID NOS: 31

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Thr
            20                  25
```

```
<210> SEQ ID NO 3
<211> LENGTH: 31
<212> TYPE: PRT
<213> ORGANISM: Artificial Sequence
<220> FEATURE:
<223> OTHER INFORMATION: Synthetic

<400> SEQUENCE: 3

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 4
<211> LENGTH: 33
<212> TYPE: PRT
<213> ORGANISM: Artificial Sequence
<220> FEATURE:
<223> OTHER INFORMATION: Synthetic

<400> SEQUENCE: 4

Lys Pro Lys Pro His Ser Gln Gly Thr Phe Thr Ser Asp Tyr Ser Lys
1               5                   10                  15

Tyr Leu Asp Ser Arg Arg Ala Gln Asp Phe Val Gln Trp Leu Leu Asn
            20                  25                  30

Thr

<210> SEQ ID NO 5
<211> LENGTH: 35
<212> TYPE: PRT
<213> ORGANISM: Artificial Sequence
<220> FEATURE:
<223> OTHER INFORMATION: Synthetic

<400> SEQUENCE: 5

Lys Pro Lys Pro Lys Pro His Ser Gln Gly Thr Phe Thr Ser Asp Tyr
1               5                   10                  15

Ser Lys Tyr Leu Asp Ser Arg Arg Ala Gln Asp Phe Val Gln Trp Leu
            20                  25                  30

Leu Asn Thr
        35

<210> SEQ ID NO 6
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with 12-aminododecanoic acid -
      12-aminododecanoic acid

<400> SEQUENCE: 6

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 7
<211> LENGTH: 31
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with 12-aminododecanoic acid -
      12-aminododecanoic acid - Lys - Lys - Lys - Lys - Lys - Lys

<400> SEQUENCE: 7

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with Lys Lys Lys Lys Lys Lys

<400> SEQUENCE: 8

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with 8-amino-3,6-dioxaoctanoic
      acid - 8-amino-3,6-dioxaoctanoic acid

<400> SEQUENCE: 9

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with 8-amino-3,6-dioxaoctanoic
      acid - 8-amino-3,6-dioxaoctanoic acid - Lys - Lys - Lys - Lys -
      Lys - Lys

<400> SEQUENCE: 10

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30
```

```
<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Lys Pro Lys Pro
1

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Lys Pro Lys Pro Lys Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Lys Lys Lys Lys Lys Lys
1               5

<210> SEQ ID NO 14
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (29)..(29)
<223> OTHER INFORMATION: C-terminus is amine modified

<400> SEQUENCE: 14

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 15
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: C-terminus is amine modified

<400> SEQUENCE: 15

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30
```

```
<210> SEQ ID NO 16
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: C-terminus is amine modified
<222> LOCATION: (33)..(33)
<220> FEATURE:
<221> NAME/KEY: MISC_FEATURE
<222> LOCATION: (33)..(33)
<223> OTHER INFORMATION: C-terminus is amind modified

<400> SEQUENCE: 16

Lys Pro Lys Pro His Ser Gln Gly Thr Phe Thr Ser Asp Tyr Ser Lys
1               5                   10                  15

Tyr Leu Asp Ser Arg Arg Ala Gln Asp Phe Val Gln Trp Leu Leu Asn
            20                  25                  30

Thr

<210> SEQ ID NO 17
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (35)..(35)
<223> OTHER INFORMATION: C-terminus us amind modified

<400> SEQUENCE: 17

Lys Pro Lys Pro Lys Pro His Ser Gln Gly Thr Phe Thr Ser Asp Tyr
1               5                   10                  15

Ser Lys Tyr Leu Asp Ser Arg Arg Ala Gln Asp Phe Val Gln Trp Leu
            20                  25                  30

Leu Asn Thr
        35

<210> SEQ ID NO 18
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: C-terminus is amine modified

<400> SEQUENCE: 18

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: C-terminus is amine modified
```

```
<400> SEQUENCE: 19

Lys Pro Lys Pro His Ser Gln Gly Thr Phe Thr Ser Asp Tyr Ser Lys
1               5                   10                  15

Tyr Leu Asp Ser Arg Arg Ala Gln Asp Phe Val Gln Trp Leu Met Asn
            20                  25                  30

Thr

<210> SEQ ID NO 20
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (35)..(35)
<223> OTHER INFORMATION: C-terminus is amine modified

<400> SEQUENCE: 20

Lys Pro Lys Pro Lys Pro His Ser Gln Gly Thr Phe Thr Ser Asp Tyr
1               5                   10                  15

Ser Lys Tyr Leu Asp Ser Arg Arg Ala Gln Asp Phe Val Gln Trp Leu
            20                  25                  30

Met Asn Thr
        35

<210> SEQ ID NO 21
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: C-terminus is amine modified

<400> SEQUENCE: 21

Glu Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with Lys Lys Lys Lys Lys Lys
<220> FEATURE:
<221> NAME/KEY: MISC_FEATURE
<222> LOCATION: (31)..(31)
<223> OTHER INFORMATION: C-terminus is amine modified

<400> SEQUENCE: 22

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30
```

```
<210> SEQ ID NO 23
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with Lys Lys Lys Lys Lys Lys
<220> FEATURE:
<221> NAME/KEY: MISC_FEATURE
<222> LOCATION: (31)..(31)
<223> OTHER INFORMATION: C-terminus is amine modified

<400> SEQUENCE: 23

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with Lys Lys Lys Lys Lys Lys

<400> SEQUENCE: 24

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with 8-amino-3,6-dioxaoctanoic
      acid - 8-amino-3,6-dioxaoctanoic acid
<220> FEATURE:
<221> NAME/KEY: MISC_FEATURE
<222> LOCATION: (31)..(31)
<223> OTHER INFORMATION: C-terminus is amine modified

<400> SEQUENCE: 25

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: Functionalized with 8-amino-3,6-dioxaoctanoic
      acid - 8-amino-3,6-dioxaoctanoic acid - Lys - Lys - Lys - Lys -
      Lys
<220> FEATURE:
<221> NAME/KEY: MISC_FEATURE
<222> LOCATION: (31)..(31)
<223> OTHER INFORMATION: C-terminus is amine modified

<400> SEQUENCE: 26

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Leu Asn Thr
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with Pro Lys Pro Lys Pro Lys
<220> FEATURE:
<221> NAME/KEY: MISC_FEATURE
<222> LOCATION: (31)..(31)
<223> OTHER INFORMATION: C-terminus is amine modified

<400> SEQUENCE: 27

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Functionalized with Pro Lys Pro Lys Pro Lys

<400> SEQUENCE: 28

Lys Pro His Ser Gln Gly Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Pro Lys Pro Lys Pro Lys
1               5
```

```
<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Glu Pro Glu Pro
1

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

Glu Pro Glu Pro Glu Pro
1               5
```